(12) United States Patent
Panken et al.

(10) Patent No.: US 9,248,288 B2
(45) Date of Patent: *Feb. 2, 2016

(54) PATIENT DIRECTED THERAPY CONTROL

(71) Applicant: Medtronic, Inc., Minneapolis, MN (US)

(72) Inventors: Eric J. Panken, Edina, MN (US);
Timothy J. Denison, Minneapolis, MN (US); Gregory F. Molnar, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 228 days.

This patent is subject to a terminal disclaimer.

(21) Appl. No.: 13/740,860

(22) Filed: Jan. 14, 2013

(65) Prior Publication Data
US 2013/0131755 A1 May 23, 2013

Related U.S. Application Data

(63) Continuation of application No. 11/974,931, filed on Oct. 16, 2007, now Pat. No. 8,380,314.

(60) Provisional application No. 60/975,372, filed on Sep. 26, 2007.

(51) Int. Cl.
*A61N 1/36* (2006.01)
*A61B 5/00* (2006.01)
(Continued)

(52) U.S. Cl.
CPC ............ *A61N 1/3606* (2013.01); *A61B 5/7475* (2013.01); *A61M 5/14276* (2013.01);
(Continued)

(58) Field of Classification Search
CPC .................... A61N 1/3605; A61N 1/36082
USPC .................................. 600/544, 545; 607/45
See application file for complete search history.

(56) References Cited

U.S. PATENT DOCUMENTS

| 1,342,885 A | 6/1920 | Armstrong |
| 3,130,373 A | 4/1964 | Braymer |

(Continued)

FOREIGN PATENT DOCUMENTS

| CN | 2754557 Y | 2/2006 |
| CN | 101099670 | 1/2008 |

(Continued)

OTHER PUBLICATIONS

Aaron et al., "Horizons in Prosthesis Development for the Restoration of Limb Function," Journal of the American Academy of Orthopaedic Surgeons, vol. 14, No. 10, 2006, pp. S198-S204.

(Continued)

*Primary Examiner* — Carl H Layno
*Assistant Examiner* — Jennifer Ghand
(74) *Attorney, Agent, or Firm* — Shumaker & Sieffert, P.A.

(57) ABSTRACT

A patient controls the delivery of therapy through volitional inputs that are detected by a biosignal within the brain. The volitional patient input may be directed towards performing a specific physical or mental activity, such as moving a muscle or performing a mathematical calculation. In one embodiment, a biosignal detection module monitors an electroencephalogram (EEG) signal from within the brain of the patient and determines whether the EEG signal includes the biosignal. In one embodiment, the biosignal detection module analyzes one or more frequency components of the EEG signal. In this manner, the patient may adjust therapy delivery by providing a volitional input that is detected by brain signals, wherein the volitional input may not require the interaction with another device, thereby eliminating the need for an external programmer to adjust therapy delivery. Example therapies include electrical stimulation, drug delivery, and delivery of sensory cues.

26 Claims, 22 Drawing Sheets

(51) Int. Cl.
  *A61M 5/142* (2006.01)
  *A61M 5/172* (2006.01)
  *A61N 1/372* (2006.01)
  *G06F 3/01* (2006.01)
  *A61B 5/048* (2006.01)

(52) U.S. Cl.
  CPC ........... *A61M5/1723* (2013.01); *A61N 1/3605* (2013.01); *A61N 1/36014* (2013.01); *A61N 1/37252* (2013.01); *G06F 3/015* (2013.01); *A61B 5/048* (2013.01); *A61M 2210/0693* (2013.01); *A61N 1/36017* (2013.01); *A61N 1/36021* (2013.01); *A61N 1/36025* (2013.01); *A61N 1/36071* (2013.01); *A61N 1/36082* (2013.01)

(56) References Cited

U.S. PATENT DOCUMENTS

| | | | |
|---|---|---|---|
| 3,603,997 A | 9/1971 | Brouwer et al. | |
| 3,780,725 A | 12/1973 | Goldberg | |
| 4,013,068 A | 3/1977 | Settle et al. | |
| 4,138,649 A | 2/1979 | Schaffer | |
| 4,177,819 A | 12/1979 | Kofsky et al. | |
| 4,188,586 A | 2/1980 | Egami | |
| 4,279,258 A | 7/1981 | John | |
| 4,579,125 A | 4/1986 | Strobl et al. | |
| 4,610,259 A | 9/1986 | Cohen et al. | |
| 4,612,934 A | 9/1986 | Borkan | |
| 4,733,667 A | 3/1988 | Olive et al. | |
| 4,776,345 A | 10/1988 | Cohen et al. | |
| 4,933,642 A | 6/1990 | Lee | |
| 4,979,230 A | 12/1990 | Marz | |
| 5,024,221 A | 6/1991 | Morgan | |
| 5,061,593 A | 10/1991 | Yoerger et al. | |
| 5,105,167 A | 4/1992 | Peczalski | |
| 5,113,143 A | 5/1992 | Wei | |
| 5,179,947 A | 1/1993 | Meyerson et al. | |
| 5,205,285 A | 4/1993 | Baker, Jr. | |
| 5,206,602 A | 4/1993 | Baumgartner et al. | |
| 5,282,840 A | 2/1994 | Hudrlik | |
| 5,293,879 A | 3/1994 | Vonk et al. | |
| 5,299,569 A | 4/1994 | Wernicke et al. | |
| 5,311,876 A | 5/1994 | Olsen et al. | |
| 5,334,222 A | 8/1994 | Salo et al. | |
| 5,335,657 A | 8/1994 | Terry, Jr. et al. | |
| 5,458,117 A | 10/1995 | Chamoun et al. | |
| 5,477,481 A | 12/1995 | Kerth | |
| 5,489,759 A | 2/1996 | Litt et al. | |
| 5,619,536 A | 4/1997 | Gourgue | |
| 5,663,680 A | 9/1997 | Nordeng | |
| 5,725,558 A | 3/1998 | Warnke | |
| 5,769,877 A | 6/1998 | Barreras, Sr. | |
| 5,782,884 A | 7/1998 | Stotts et al. | |
| 5,833,709 A | 11/1998 | Rise et al. | |
| 5,840,040 A | 11/1998 | Altschuler et al. | |
| 5,843,139 A | 12/1998 | Goedeke et al. | |
| 5,928,272 A | 7/1999 | Adkins et al. | |
| 5,995,868 A | 11/1999 | Dorfmeister et al. | |
| 6,011,990 A | 1/2000 | Schultz et al. | |
| 6,024,700 A | 2/2000 | Nemirovski et al. | |
| 6,061,593 A | 5/2000 | Fischell et al. | |
| 6,064,257 A | 5/2000 | Sauer | |
| 6,066,163 A | 5/2000 | John | |
| 6,070,101 A | 5/2000 | Struble et al. | |
| 6,094,598 A | 7/2000 | Elsberry et al. | |
| 6,129,681 A | 10/2000 | Kuroda et al. | |
| 6,130,578 A | 10/2000 | Tang | |
| 6,157,857 A | 12/2000 | Dimpfel | |
| 6,161,042 A | 12/2000 | Hartley et al. | |
| 6,262,626 B1 | 7/2001 | Bakker et al. | |
| 6,287,263 B1 | 9/2001 | Briskin | |
| 6,315,740 B1 | 11/2001 | Singh | |
| 6,331,160 B1 | 12/2001 | Bardy | |
| 6,356,784 B1 | 3/2002 | Lozano et al. | |
| 6,360,123 B1 | 3/2002 | Kimchi et al. | |
| 6,366,813 B1 | 4/2002 | DiLorenzo | |
| 6,456,159 B1 | 9/2002 | Brewer | |
| 6,459,936 B2 | 10/2002 | Fischell et al. | |
| 6,463,328 B1 | 10/2002 | John | |
| 6,468,234 B1 | 10/2002 | Van der Loos et al. | |
| 6,522,914 B1 | 2/2003 | Huvelle et al. | |
| 6,539,261 B2 | 3/2003 | Dal Molin | |
| 6,584,351 B1 | 6/2003 | Ekwall | |
| 6,597,953 B2 | 7/2003 | Boling | |
| 6,605,038 B1 | 8/2003 | Teller et al. | |
| 6,617,838 B1 | 9/2003 | Miranda et al. | |
| 6,625,436 B1 | 9/2003 | Tolson et al. | |
| 6,658,287 B1 | 12/2003 | Litt et al. | |
| 6,667,760 B1 | 12/2003 | Limberg | |
| 6,674,322 B2 | 1/2004 | Motz | |
| 6,725,091 B2 | 4/2004 | Dal Molin | |
| 6,754,535 B2 | 6/2004 | Noren et al. | |
| 6,810,285 B2 | 10/2004 | Pless et al. | |
| 6,819,956 B2 | 11/2004 | DiLorenzo | |
| 6,839,594 B2 | 1/2005 | Cohen et al. | |
| 6,876,842 B2 | 4/2005 | Davie | |
| 6,904,321 B1 | 6/2005 | Bornzin et al. | |
| 6,914,539 B2 | 7/2005 | Hoctor et al. | |
| 6,954,524 B2 | 10/2005 | Gibson et al. | |
| 6,993,380 B1 | 1/2006 | Modarres | |
| 7,006,872 B2 | 2/2006 | Gielen et al. | |
| 7,010,347 B2 | 3/2006 | Schecter | |
| 7,098,823 B2 | 8/2006 | O'Dowd et al. | |
| 7,110,820 B2 | 9/2006 | Tcheng et al. | |
| 7,120,486 B2 | 10/2006 | Leuthardt et al. | |
| 7,142,917 B2 | 11/2006 | Fukui | |
| 7,146,208 B2 | 12/2006 | Holmstrom et al. | |
| 7,146,218 B2 | 12/2006 | Esteller et al. | |
| 7,151,961 B1 | 12/2006 | Whitehurst et al. | |
| 7,171,258 B2 | 1/2007 | Goode | |
| 7,209,788 B2 | 4/2007 | Nicolelis et al. | |
| 7,233,198 B2 | 6/2007 | Niederkorn | |
| 7,239,927 B2 | 7/2007 | Ganion | |
| 7,295,061 B1 | 11/2007 | Dasgupta | |
| 7,299,088 B1 | 11/2007 | Thakor et al. | |
| 7,376,463 B2 | 5/2008 | Salo et al. | |
| 7,385,443 B1 | 6/2008 | Denison | |
| 7,391,257 B1 | 6/2008 | Denison et al. | |
| 7,519,431 B2 | 4/2009 | Goetz et al. | |
| 7,595,648 B2 | 9/2009 | Ungaretti et al. | |
| 7,622,988 B2 | 11/2009 | Denison et al. | |
| 7,671,672 B2 | 3/2010 | McConnell | |
| 7,684,867 B2 | 3/2010 | Jaax et al. | |
| 7,769,464 B2 | 8/2010 | Gerber et al. | |
| 7,813,802 B2 | 10/2010 | Tcheng et al. | |
| 7,826,894 B2 | 11/2010 | Musallam et al. | |
| 7,847,628 B2 | 12/2010 | Denison | |
| 8,121,694 B2 | 2/2012 | Molnar et al. | |
| 8,290,596 B2 | 10/2012 | Wei et al. | |
| 8,380,314 B2 | 2/2013 | Panken et al. | |
| 2002/0002390 A1 | 1/2002 | Fischell et al. | |
| 2002/0038137 A1 | 3/2002 | Stein | |
| 2002/0091332 A1 | 7/2002 | Bombardini | |
| 2002/0103512 A1 | 8/2002 | Echauz et al. | |
| 2002/0177882 A1 | 11/2002 | DiLorenzo | |
| 2003/0046254 A1 | 3/2003 | Ryu et al. | |
| 2003/0105409 A1 | 6/2003 | Donoghue et al. | |
| 2003/0146786 A1 | 8/2003 | Gulati et al. | |
| 2003/0149457 A1 | 8/2003 | Tcheng et al. | |
| 2003/0158587 A1 | 8/2003 | Esteller et al. | |
| 2003/0171791 A1 | 9/2003 | KenKnight et al. | |
| 2004/0015211 A1 | 1/2004 | Nurmikko et al. | |
| 2004/0077967 A1 | 4/2004 | Jordan | |
| 2004/0082875 A1 | 4/2004 | Donoghue et al. | |
| 2004/0122483 A1 | 6/2004 | Nathan et al. | |
| 2004/0141558 A1 | 7/2004 | Plisch et al. | |
| 2004/0176809 A1 | 9/2004 | Cho et al. | |
| 2004/0215286 A1 | 10/2004 | Stypulkowski | |
| 2004/0249302 A1 | 12/2004 | Donoghue et al. | |
| 2004/0249422 A1 | 12/2004 | Gliner et al. | |
| 2005/0007091 A1 | 1/2005 | Makeig et al. | |
| 2005/0043652 A1 | 2/2005 | Lovett et al. | |

(56) References Cited

U.S. PATENT DOCUMENTS

| | | |
|---|---|---|
| 2005/0081847 A1 | 4/2005 | Lee et al. |
| 2005/0113744 A1 | 5/2005 | Donoghue et al. |
| 2005/0118968 A1 | 6/2005 | Cowley |
| 2005/0143589 A1 | 6/2005 | Donoghue et al. |
| 2005/0182447 A1 | 8/2005 | Schecter |
| 2005/0197588 A1 | 9/2005 | Freeberg |
| 2005/0203366 A1 | 9/2005 | Donoghue et al. |
| 2005/0209511 A1 | 9/2005 | Heruth et al. |
| 2005/0209512 A1 | 9/2005 | Heruth et al. |
| 2005/0209644 A1 | 9/2005 | Heruth et al. |
| 2005/0240242 A1 | 10/2005 | DiLorenzo |
| 2005/0282517 A1 | 12/2005 | Cowley |
| 2006/0041221 A1 | 2/2006 | Stypulkowski |
| 2006/0049957 A1 | 3/2006 | Surgenor et al. |
| 2006/0055456 A1 | 3/2006 | Niederkorn |
| 2006/0058627 A1 | 3/2006 | Flaherty et al. |
| 2006/0106275 A1 | 5/2006 | Raniere |
| 2006/0116591 A1 | 6/2006 | Cooper |
| 2006/0133550 A1 | 6/2006 | Bolton et al. |
| 2006/0135877 A1 | 6/2006 | Giftakis et al. |
| 2006/0135879 A1 | 6/2006 | Liley |
| 2006/0139192 A1 | 6/2006 | Morrow et al. |
| 2006/0139193 A1 | 6/2006 | Morrow et al. |
| 2006/0149338 A1 | 7/2006 | Flaherty et al. |
| 2006/0167530 A1 | 7/2006 | Flaherty et al. |
| 2006/0169282 A1 | 8/2006 | Izumi et al. |
| 2006/0173259 A1 | 8/2006 | Flaherty et al. |
| 2006/0173494 A1 | 8/2006 | Armstrong et al. |
| 2006/0173501 A1 | 8/2006 | Stickney et al. |
| 2006/0184060 A1 | 8/2006 | Belalcazar et al. |
| 2006/0189899 A1 | 8/2006 | Flaherty et al. |
| 2006/0206167 A1 | 9/2006 | Flaherty et al. |
| 2006/0206174 A1 | 9/2006 | Honeycutt et al. |
| 2006/0212089 A1 | 9/2006 | Tass |
| 2006/0212090 A1 | 9/2006 | Lozano et al. |
| 2006/0212093 A1 | 9/2006 | Pless et al. |
| 2006/0241357 A1 | 10/2006 | Chirife |
| 2006/0253166 A1 | 11/2006 | Flaherty et al. |
| 2006/0253168 A1 | 11/2006 | Wyler et al. |
| 2006/0258930 A1 | 11/2006 | Wu et al. |
| 2006/0259099 A1 | 11/2006 | Goetz et al. |
| 2006/0265022 A1 | 11/2006 | John et al. |
| 2006/0281427 A1 | 12/2006 | Isaac et al. |
| 2006/0293604 A1 | 12/2006 | Carlson et al. |
| 2006/0293720 A1 | 12/2006 | DiLorenzo |
| 2007/0010755 A1 | 1/2007 | Sarkela et al. |
| 2007/0016095 A1 | 1/2007 | Low et al. |
| 2007/0032737 A1 | 2/2007 | Causevic et al. |
| 2007/0032738 A1 | 2/2007 | Flaherty et al. |
| 2007/0032834 A1 | 2/2007 | Gliner et al. |
| 2007/0038265 A1 | 2/2007 | Tcheng et al. |
| 2007/0046486 A1 | 3/2007 | Donoghue et al. |
| 2007/0073355 A1 | 3/2007 | DiLorenzo |
| 2007/0077907 A1 | 4/2007 | Rector |
| 2007/0123758 A1 | 5/2007 | Miesel et al. |
| 2007/0150025 A1 | 6/2007 | DiLorenzo et al. |
| 2007/0179534 A1 | 8/2007 | Firlik et al. |
| 2007/0213785 A1 | 9/2007 | Osorio et al. |
| 2007/0216477 A1 | 9/2007 | McConnell |
| 2007/0249953 A1 | 10/2007 | Frei et al. |
| 2008/0015659 A1 | 1/2008 | Zhang et al. |
| 2008/0051839 A1 | 2/2008 | Libbus et al. |
| 2008/0071314 A1 | 3/2008 | John |
| 2008/0077191 A1 | 3/2008 | Morrell |
| 2008/0154111 A1 | 6/2008 | Wu et al. |
| 2008/0180278 A1 | 7/2008 | Denison |
| 2008/0195166 A1 | 8/2008 | Sun et al. |
| 2008/0243005 A1 | 10/2008 | Jung et al. |
| 2008/0269630 A1 | 10/2008 | Denison et al. |
| 2008/0269631 A1 | 10/2008 | Denison et al. |
| 2008/0269812 A1 | 10/2008 | Gerber et al. |
| 2008/0269841 A1 | 10/2008 | Grevious et al. |
| 2009/0082691 A1 | 3/2009 | Denison et al. |
| 2009/0105785 A1 | 4/2009 | Wei et al. |
| 2009/0118786 A1 | 5/2009 | Meadows et al. |
| 2009/0118787 A1 | 5/2009 | Moffitt et al. |
| 2009/0131995 A1 | 5/2009 | Sloan et al. |
| 2009/0192556 A1 | 7/2009 | Wu et al. |
| 2009/0264789 A1 | 10/2009 | Molnar et al. |
| 2010/0033240 A1 | 2/2010 | Denison et al. |
| 2010/0113964 A1 | 5/2010 | Wahlstrand et al. |
| 2010/0114223 A1 | 5/2010 | Wahlstrand et al. |
| 2010/0324442 A1 | 12/2010 | Blomqvist |
| 2010/0327887 A1 | 12/2010 | Denison et al. |
| 2011/0004268 A1 | 1/2011 | Tcheng et al. |
| 2011/0068861 A1 | 3/2011 | Denison |

FOREIGN PATENT DOCUMENTS

| | | |
|---|---|---|
| DE | 19649991 A1 | 6/1998 |
| EP | 0354060 A2 | 2/1990 |
| EP | 0438945 A1 | 7/1991 |
| EP | 789449 | 8/1997 |
| EP | 1943944 A1 | 7/2008 |
| GB | 1249395 | 10/1971 |
| GB | 2447640 A | 9/2008 |
| JP | 4717841 | 9/1972 |
| JP | 5615112 | 12/1981 |
| JP | 6224659 | 8/1994 |
| JP | 7120207 | 5/1995 |
| JP | 10504099 | 4/1998 |
| JP | 2006279377 | 10/2006 |
| JP | 2008154681 | 7/2008 |
| KR | 20010096372 | 11/2001 |
| RU | 2144310 C1 | 1/2000 |
| WO | WO 97/10747 | 3/1997 |
| WO | WO 00/10455 A1 | 3/2000 |
| WO | WO 02/01711 | 1/2002 |
| WO | WO 02/03087 | 1/2002 |
| WO | WO 02/49500 A2 | 6/2002 |
| WO | WO 02/058536 A2 | 8/2002 |
| WO | WO 03/101532 A2 | 12/2003 |
| WO | WO 03/101532 A3 | 12/2003 |
| WO | WO 2005/001707 A2 | 1/2005 |
| WO | WO 2005/001707 A3 | 1/2005 |
| WO | WO 2005/046469 A2 | 5/2005 |
| WO | WO 2005/046469 A3 | 5/2005 |
| WO | WO 2005/089646 A1 | 9/2005 |
| WO | WO 2005/092183 A1 | 10/2005 |
| WO | WO 2006/015002 A1 | 2/2006 |
| WO | WO 2006/020794 A2 | 2/2006 |
| WO | WO 2006/020794 A3 | 2/2006 |
| WO | WO 2006/066098 A1 | 6/2006 |
| WO | WO 2006/073915 A2 | 7/2006 |
| WO | WO 2006/073915 A3 | 7/2006 |
| WO | WO 2006/074029 A2 | 7/2006 |
| WO | WO 2006/074029 A3 | 7/2006 |
| WO | WO 2006/076164 A2 | 7/2006 |
| WO | WO 2006/076164 A3 | 7/2006 |
| WO | WO 2006/121455 A1 | 11/2006 |
| WO | WO 2006/126186 A2 | 11/2006 |
| WO | WO 2007/112092 A2 | 10/2007 |
| WO | WO 2008/103078 A1 | 8/2008 |
| WO | WO 2008/105692 A1 | 9/2008 |
| WO | WO 2009/042172 A2 | 4/2009 |
| WO | WO 2009/042313 A2 | 4/2009 |
| WO | WO 2009/059041 A1 | 5/2009 |

OTHER PUBLICATIONS

Abidi, "CMOS wireless transceivers: the new wave," IEEE Communications Magazine 37, 119-124 (1999).

Acuna et al., "Cognitive mechanisms of transitive inference," Exp Brain Res, Sep. 2002, vol. 146, pp. 1-10.

Acuna et al., "Frontal and Parietal Lobe Activation during Transitive Inference in Humans," Cerebral Cortex, vol. 12, No. 12, Dec. 2002, pp. 1312-1321.

Anderson et al., "Recording Advances for Neural Prosthetics," in Engineering in Medicine and Biology Society, Sep. 2004. IEMBS 2004, 26th Annual International Conference of the IEEE, pp. 5352-5355, vol. 7.

Anderson et al., "Selecting the signals for a brain-machine interface," Curr Opin Neurobiol, vol. 14, pp. 720-726, Dec. 2004.

(56) References Cited

OTHER PUBLICATIONS

Avestruz et al., "A 5 uW/Channel Spectral Analysis IC for Chronic Bidirectional Brain-Machine Interfaces," IEEE Journal of Solid-State Circuits, vol. 43, No. 12., Dec. 2008, 19 pp.
Bakker et al., "A CMOS Nested-Chopper Instrumentation Amplifier with 100-nV Offset," IEEE Journal of Solid-State Circuits, vol. 35, No. 12, pp. 1877-1883, Dec. 2000.
Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997, 20 pp.
Brown et al., "Basal ganglia local field potential activity: Character and functional significance in the human," Clinical Neurology, vol. 116, 2005, pp. 2510-2519.
Brown, "Oscillatory Nature of Human Basal Ganglia Activity: Relationship to the Pathophysiology of Parkinson's Disease," Movement Disorders, vol. 18, No. 4, 2003, pp. 357-363.
Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006, 2 pages.
Cohen et al., "The physiology of brain-computer interfaces," Journal of Physiology, vol. 579, No. 3, 2007, p. 570.
Denison et al., "A 2.2 µW 94nV/√Hz, Chopper-Stabilized Instrumentation Amplifier for EEG Detection in Chronic Implants," Soli-State Circuits Conference, Feb. 2007, Digest of Technical Papers, IEEE International, 3 pages.
Denison et al., "A 2 µW 100 nV/rtHz Chopper-Stabilized Instrumentation Amplifier for Chronic Measurement of Neural Field Potentials," Solid-state circuits, IEEE Journal, vol. 42, pp. 2934-2945, Dec. 2007.
Denison et al., "An 8 µW heterodyning chopper amplifier for direct extraction of 2 µVrms Neuronal Brain Biomarkers," ISSCC, Jul. 2008, paper 8.1, 3 pages.
Donoghue et al., "Assistive technology and robotic control using motor cortex ensemble-based neural interface systems in humans with tetraplegia," Journal of Physiology 579.3, Feb. 2007, pp. 603-611.
Donoghue et al., "Development of neuromotor prostheses for humans," Advances in Clinical Neurophysiology, Supplements to Clinical Neurophysiology, vol. 57, 2004, pp. 592-606.
Donoghue et al., "Motor Areas of the Cerebral Cortex," Journal of Clinical Neurophysiology, vol. 11, No. 4, pp. 382-396, 1994.
Donoghue, "Connecting cortex to machines: recent advances in brain interfaces," Nature Neuroscience, supplement, vol. 5, Nov. 2002, pp. 1085-1088.
Dzwonczyk et al., "Myocardial Electrical Impedance Responds to Ischemia and Reperfusion in Humans," IEEE Transactions on Biomedical Engineering, IEEE Service Center, vol. 51, No. 12, Dec. 2004, pp. 2206-2209.
Eden et al., "Reconstruction of Hand Movement Trajectories from a Dynamic Ensemble of Spiking Motor Cortical Neurons," Proceedings of the 26th Annual International Conference of the IEEE EMBS, San Francisco, CA, USA, Sep. 1-5, 2004, pp. 4017-4020.
Enz et al., "Circuit Techniques for Reducing the Effects of Opamp Imperfections," Proc. of the IEEE, vol. 84, No. 11, pp. 1584-1614, Nov. 1996.
Fetz, "Volitional control of neural activity: implications for brain-computer interfaces," Journal of Physiology, vol. 579, No. 3, 2007, pp. 571-579.
Foffani et al., "Analysis of local field potentials from the human subthalamic nucleus," Proceedings of the 25th Annual International Conference of the IEEE EMBS, Sep. 17-21, 2003, 3 pages.
Friehs et al., "Brain-Machine and Brain-Computer Interfaces," Stroke, vol. 35, No. 11, Supplement 1, Nov. 2004, pp. 2702-2705.
Haddad et al., "An ultra low-power dynamic translinear cardiac sense amplifier for pacemakers," Circuits and Systems, Mar. 2003, pp. V-37-V40 vol. 5.
Haddad et al., "Analog wavelet transform employing dynamic translinear circuits for cardiac signal characterization," circuits and systems, 2003, pp. 1-121-1-124, vol. 1.
Hadiashar et al., "A Chopper Stabilized CMOS Analog Multiplier with Ultra Low DC Offsets," Solid-State Circuits Conference, pp. 364-367, Sep. 2006.
Harrison et al., A Low-Power Integrated Circuit for a Wireless 100—Electrode Neural Recording System, Solid state circuits. IEEE Journal of, vol. 42, No. 1, pp. 123-133, Jan. 2007.
Harrison et al., "A Low-Power Low-Noise CMOS Amplifier for Neural Recording Applications," IEEE J. of Solid-State Circuits, vol. 38, No. 6, pp. 958-965, Jun. 2003.
Harrison et al., "Local Field Potential Measurement with Low-Power Analog Integrated Circuit," Sep. 1-5, 2004, 4 pages.
Hatsopoulos et al., "Cortically controlled brain-machine interface," Proceedings of the 2005 IEEE, Engineering in Medicine and Biology 27th Annual Conference, Sep. 1-4, 2005, pp. 7660-7663.
Heldman et al., "Local Field Potential Spectral Tuning in Motor Cortex During Reaching," IEEE Transactions on Neural Systems and Rehabilitation Engineering, vol. 14, No. 2, Jun. 2006, pp. 180-183.
Hess et al., "Long-Term Potentiation of Horizontal Connections Provides a Mechanism to Reorganize Cortical Motor Maps," Journal of Neurophysiology, vol. 71, No. 6, Jun. 1994, pp. 2543-2547.
Hochberg et al., "Neuronal ensemble control of prosthetic devices by a human with tetraplegia," Nature, vol. 442, Jul. 2006, pp. 164-171.
Hochberg et al., "Sensors for Brain-Computer Interfaces: Options for Turning Thought into Action," IEEE Engineering in Medicine and Biology Magazine, Sep./Oct. 2006, pp. 32-38.
Hoshi,"Functional specialization within the dorsolateral prefrontal cortex: A review of anatomical and physiological studies of non-human primates," Neuroscience Research 54, 2006, pp. 73-84.
International Search Report and the Written Opinion of international patent application No. PCT/US2008/011109, dated Jan. 1, 2009, 13 pages.
Krusienski et al.,"µ-Rhythm Matched Filter for Continuous Control of a Brain-Computer Interface," Biomedical Engineering, IEEE Transactions on, vol. 54, pp. 273-280, Feb. 2007.
Kun et al., "Algorithm for Tissue Ischemia Estimation Based on Electrical Impedance Spectroscopy," IEEE Transactions on Biomedical Engineering, IEEE Service Center, vol. 50, No. 12, Dec. 2003, pp. 1352-1359.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, pp. 76-77, Mar. 2008.
Makinwa et al., A CMOS Temperature-to-frequency converter with an Inaccuracy of less than ±0.5° C. (3σ) from -40° C. to 105° C. IEEE Journal of Solid State Circuits, vol. 41, No. 12 , pp. 2992-2997, Dec. 2006.
Makinwa, "Dynamic Offset Cancellation Techniques," Smart Sensor Systems '02, May, 2002, 42 pages.
Martins et al., "A CMOS IC for Portable EEG Acquisition Systems," IEEE Transactions on Instrumentation and Measurement, vol. 47, No. 5, pp. 1191-1196, Oct. 1998.
Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, 2007, 5 pp.
Maynard et al., "Neuronal Interactions Improve Cortical Population Coding of Movement Direction," The Journal of Neuroscience, vol. 19, No. 18, Sep. 15, 1999, pp. 8083-8093.
Min et al., "Electrical Impedance and Cardiac Monitoring—Technology, Potential and Applications," International Journal of Bioelectromagnetism, International Society for Bioelectromagnetism, vol. 5. No. 1, Jan. 2003, pp. 53-56.
Ng et al., "A CMOS Analog Front-End IC for Portable EEG/ECG Monitoring Applications," IEEE Trans. On Circuits and Systems, vol. 52 No. 11, Nov. 2005, 13 pages.
Ojakangas et al, "Decoding movement intent from human premotor cortex neurons for neural prosthetic applications," Journal of Clinical Neurophysiology, vol. 23, No. 6, Dec. 2006, pp. 1-14.

(56) References Cited

OTHER PUBLICATIONS

Paninski et al., "Spatiotemporal Tuning of Motor Cortical Neurons for Hand Position and Velocity," Journal of Neurophysiology, vol. 91, 2004, pp. 515-532.

Paninski et al., "Superlinear Population Encoding of Dynamic Hand Trajectory in Primary Motor Cortex," The Journal of Neuroscience, vol. 24, No. 39, Sep. 29, 2004, pp. 8551-8561.

Patterson et al., "A Microlectrode/Microelectronic Hybrid Device for Brain Implantable Neuroprosthesis Applications," IEEE Transactions on Biomedical Engineering, vol. 51, No. 10, Oct. 2004, pp. 1845-1853.

Rauscher, "Practical Realization of an Analyzer Operating on the Heterodyne Principle," Chapter 4 (partial) of Fundamentals of Spectrum Analysis (Rohde & Schwarz, 2001 ). pp. 34-64. With 2 pages of front matter and 2 pages of diagrams.

Salthouse et al., "A practical micropower programmable bandpass filter for use in bionic ears," Solid-state Circuits, IEEE Journal, vol. 38, pp. 63-70, Jan. 2003.

Sanduleanu et al., "A Low Noise, Low Residual Offset, Chopped Amplifier for Mixed Level Applications," IEEE, 0-7803-5008-1/98, pp. 333-336, Sep. 1998.

Sanes et al., "Plasticity and Primary Motor Cortex," Annual Review of Neuroscience, vol. 23, 2000, pp. 393-415.

Sarpeshkar et al., "An ultra-low-power programmable analog bionic ear processor," Biomedical Engineering, IEEE Transactions, vol. 52, pp. 711-727, Apr. 2005.

Sarpeshkar et al., Low power circuits for brain—machine interfaces, Circuits and Systems, Sep. 2007, pp. 2068-2071.

Sarpeshkar, "Borrowing from biology makes for low-power computing," IEEE Spectrum, pp. 24-29, May 2006.

Schwartz, "Useful signals from motor cortex", Journal of Physiology, vol. 579, No. 3, 2007, pp. 581-601.

Serruya et al., "Instant neural control of a movement signal," Nature, vol. 416, Mar. 2002, pp. 141-142.

Serruya et al., "Robustness of neuroprosthetic decoding algorithms," Biological Cybernetics, vol. 88, 2003, pp. 219-228.

Shoham et al., "Statistical Encoding Model for a Primary Motor Cortical Brain-Machine Interface," IEEE Transactions on Biomedical Engineering, vol. 52, No. 7, Jul. 2005, pp. 1312-1322.

Silberstein et al., "Patterning of globus pallidus local field potentials differs between Parkinson's disease and dystonia," Brain, vol. 126, 2003, pp. 2597-2608.

Smart et al., "Automatic Detection of High Frequency Epileptiform Oscillations from Intracranial EEG Recordings of Patients with Neocortical Epilepsy," in Technical, Professional and Student Development Workshop, 2005 IEEE Region 5 and IEEE Denver Section, Apr. 2005, pp. 53-58.

Song et al., "Development of a Chipscale Integrated Microelectrode/Microelectronic Device for Brain Implantable Neuroengineering Applications," IEEE Transactions on Neural Systems and Rehabilitation Engineering, vol. 13, No. 2, Jun. 2005, pp. 220-226.

Song et al., "Development of an Integrated Microelectrode/Microelectronic Device for Brain Implantable Neuroengineering Applications," Proceedings of the 26th Annual International Conference of the IEEE EMBS, San Francisco, CA, USA, Sep. 1-5, 2004, pp. 4053-4056.

Suner et al., "Reliability of Signals From a Chronically Implanted, Silicon-Based Electrode Array in Non-Human Primate Primary Motor Cortex," IEEE Transactions on Neural Systems and Rehabilitation Engineering, vol. 13, No. 4, Dec. 2005, pp. 524-541.

Tornqvist et al., "Effects of Different Electrical Parameter Settings on the Intelligibility of Speech in Patients with Parkinson's Disease Treated With Subthalamic Deep Brain Stimulation," Movement Disorders, vol. 20, No. 4, 2005, pp. 416-423.

Wattanapanitch et al., "An energy-efficient micropower neural recording amplifier," Biomedical Circuits and Systems, IEEE Transactions, vol. 1, pp. 136-147, Jun. 2007.

Wingeier et al., "Intra-operative STN DBS attenuates the prominent beta rhythm in the STN in Parkinson's disease," Experimental Neurology, 2005, 8 pp.

Wolpaw, "Brain-computer interfaces as new brain output pathways," Journal of Physiology, vol. 579, No. 3, 2007, pp. 613-619.

Wood et al., "Automatic Spike Sorting for Neural Decoding," Proceedings of the 26th Annual International Conference of the IEEE EMBS, San Francisco, CA, USA, Sep. 1-5, 2004, pp. 4009-4012.

Wood et al., "Inferring Attentional State and Kinematics from Motor Cortical Firing Rates," Proceedings of the 2005 IEEE, Engineering in Medicine and Biology 27th Annual Conference, Sep. 1-4, 2005, pp. 149-152.

Wood et al., "On the Variability of Manual Spike Sorting," IEEE Transactions on Biomedical Engineering, vol. 51, No. 6, Jun. 2004, pp. 912-918.

Wu et al., "A 1V 2.3 µW Biomedical Signal Acquisition IC," ISSCC Digest of Technical Papers 2006, paper 2.7, Feb. 2006, 2 pages.

Wu et al., "Bayesian Population Decoding of Motor Cortical Activity Using a Kalman Filter," Neural Computation, vol. 18, No. 1, 2006, pp. 80-118.

Wu et al., "Closed-Loop Neural Control of Cursor Motion using a Kalman Filter," Proceedings of the 26th Annual International Conference of the IEEE EMBS, San Francisco, CA, USA, Sep. 1-5, 2004, pp. 4126-4129.

Wu et al., "Modeling and Decoding Motor Cortical Activity Using a Switching Kalman Filter," IEEE Transactions on Biomedical Engineering, vol. 51, No. 6, Jun. 2004, pp. 933-942.

Yates, "An ultra low power low noise chopper amplifier for wireless EEG". In 49th IEEE International Midwest Symposium on Circuits and Systems, vol. 2, 449-452 (IEEE 2006).

Yazicioglu et al., "A 200 µW Eight-Channel Acquisition ASIC for Ambulatory EEG Systems," Solid-state circuits conference, Jul. 2008, 3 pages.

Yazicioglu et al., "A 60 µW 60nV/√Hz Readout Front-End for Portable Biopotential Acquisition Systems," ISSCC Digest of Technical Papers 2006, paper 2.6, Feb. 2006, 2 pages.

Ying, "Chopper Stabilized Amplifiers," Term Paper, Department of Electrical and Computer Engineering, University of Toronto, 17 pgs., Nov. 12, 2001.

Prosecution history from parent U.S. Appl. No. 11/974,931, dated Sep. 16, 2010, through Jan. 26, 2012, 62 pp.

Prosecution history from U.S. Appl. No. 12/237,799, dated Mar. 10, 2011, through Mar. 18, 2013, 43 pp.

Prosecution history from U.S. Appl. No. 13/345,397, dated Nov. 21, 2012, through Mar. 18, 2013, 43 pp.

Japanese Office Action from Japanese application No. 2009-548232, dated Apr. 20, 2011, 4 pp.

Japanese Office Action from Japanese application No. 2009-548231, dated May 18, 2011, 2 pp.

Response to Final Office Action dated Mar. 18, 2013, from U.S. Appl. No. 13/345,397, filed May 16, 2013, 9 pp.

International Search Report and Written Opinion of international application No. PCT/US2008/075660, dated Jan. 27, 2009, 12 pp.

International Preliminary Report on Patentability from international application No. PCT/US2008/075660, dated Aug. 17, 2009, 9 pp.

English translation of abstract of Jianping et al.,"Study on Feature Extraction of the Sleep-Multigraph", Journal of Biomedical Engineering, Issue 5, vol. 22, Dec. 31, 2005, 2 pp.

PATIENT DIRECTED THERAPY CONTROL

This application is a continuation of U.S. application Ser. No. 11/974,931 by Panken et al., entitled "PATIENT DIRECTED THERAPY CONTROL," and filed Oct. 16, 2007, which claims the benefit of U.S. Provisional Application No. 60/975,372 by Denison et al., entitled "FREQUENCY SELECTIVE MONITORING OF PHYSIOLOGICAL SIGNALS," and filed on Sep. 26, 2007. U.S. application Ser. No. 11/974,931 issued as U.S. Pat. No. 8,380,314 on Feb. 19, 2013. The entire content of application Nos. 11/974,931 and 60/975,372 is incorporated herein by reference.

TECHNICAL FIELD

The invention relates to medical devices and, more particularly, to devices that control therapy delivery.

BACKGROUND

Medical devices may be used to deliver therapy to patients to treat a variety of symptoms or conditions, such as chronic pain, tremor, Parkinson's disease, epilepsy, neuralgia, urinary or fecal incontinence, sexual dysfunction, obesity, or gastroparesis. A medical device may deliver stimulation therapy via leads that include electrodes located proximate to the spinal cord, pelvic nerves, stomach, or within the brain of a patient. In some cases, electrodes may be integrated with an implantable pulse generator, eliminating the need for leads. In some cases, a medical device may deliver a drug or another fluid to a specific tissue site within the patient via a catheter attached to the medical device. Alternatively, a patient with a neurological disease may be treated with external sensory cue. In any case, the medical device is used to provide treatment to the patient as needed in order in increase the quality of life of the patient. The medical device may be implanted or located externally, depending upon the type of therapy and needs of the patient.

A clinician may program the medical device to effectively treat the patient. For example, the clinician may define the therapy to be delivered to a patient by selecting values for one or more programmable therapy parameters. As one example, in the case of electrical stimulation, the clinician may select an amplitude, which may be a current or voltage amplitude, and pulse width for a stimulation waveform to be delivered to the patient, as well as a rate at which the pulses are to be delivered to the patient. Programmable therapy parameters also may include electrode combinations and polarities. The clinician may also create multiple programs having various different therapy parameter combinations that the patient may use as desired in order to find the most effective therapy parameters to treat a condition.

At least in the case of a chronic therapy delivery system, the patient begins to use the medical device for continued treatment during normal daily activities after an initial programming session with the clinician. During treatment, the patient may need to adjust the therapy parameters in order to increase the efficacy of the therapy. Adjustments to therapy may include, for example, turning the therapy on and off, switching between therapy programs, and increasing or decreasing therapy amplitude. The patient uses an external programmer, e.g., a patient programmer, to communicate any desired adjustments to the medical device. As an example, the external programmer may be a hand-held computing device that includes a user interface that allows the user to select certain adjustments to therapy. The patient may select the adjustments and the external programmer communicates the adjustments to the medical device, resulting in an adjusted therapy. The patient may continue to use the external programmer throughout the duration of therapy in order to retrain efficacious therapy.

SUMMARY

A patient may control an aspect of therapy delivery with volitional input, which is detected via biosignals within the brain. The biosignals are generated in response to a volitional patient input and are not generated because of a symptom of the patient's condition. In this way, the patient may control therapy delivery via volitional thoughts. Therapy adjustment actions that may be taken in response to the detection of the biosignal include initiating or deactivating therapy delivery, or increasing or decreasing a therapy parameter, such as amplitude of stimulation signals, pulse rate or frequency, in the case of electrical stimulation. Therapy adjustment actions may also include shifting between stored therapy programs.

The volitional patient input may not require the interaction with an external device. For example, the volitional input may include performing a specific physical or mental activity, such as moving a specific muscle or muscle group or performing a mathematical calculation. In one embodiment, a biosignal detection module detects one or more biosignals resulting from the volitional patient input by monitoring an electroencephalogram (EEG) signal from within one or more regions of the patient's brain, and determines whether the EEG signal includes the biosignal. For example, the biosignal detection module or another processor may analyze one or more predetermined frequency band components of the monitored EEG signal to determine whether the EEG signal includes the biosignal.

Detection of a biosignal within the patient's brain that results from a volitional patient input allows a patient to control therapy without the use of an external programmer. In this manner, therapy control is based on brain signals, rather than interacting with a user interface of an external programmer. Example therapies include electrical stimulation, drug delivery, an externally or internally generated sensory cue, and any combination thereof. In addition, the system may support a learning mode to determine the biosignal. For example, one learning mode correlates a monitored EEG signal with a volitional patient input. A characteristic of the EEG signal may be extracted from the monitored EEG signal to generate the biosignal. In this way, the feedback for the closed loop therapy adjustment may be customized to a particular patient.

In one embodiment, the disclosure provides a method including detecting at least one biosignal from a brain of a patient that results from a volitional patient input, and controlling delivery of therapy to the patient based on the biosignal.

In another embodiment, the disclosure provides a system comprising a therapy module to delivers therapy to a patient, a biosignal detection module to detect at least one biosignal from a brain of a patient that results from a volitional patient input, and a processor to controls the therapy device based on the detection of the biosignal.

In another embodiment, the disclosure is directed to a system that includes a sensing module configured to sense an electroencephalogram (EEG) signal of a patient, and a processor to determine whether the EEG signal includes a biosignal. The biosignal is based on a volitional patient input, wherein the processor generates a control signal to control a therapy module if the EEG signal includes the biosignal.

The disclosure provides one or more advantages. For example, the therapy systems eliminate the need for an external programmer to adjust therapy, which allows the patient to adjust therapy in situations where use of a programmer may not be possible or suggested. Example situations include bathing, swimming, driving, or any situation in which the patient may not be able to carry a programmer or the patient does not have a free hand.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
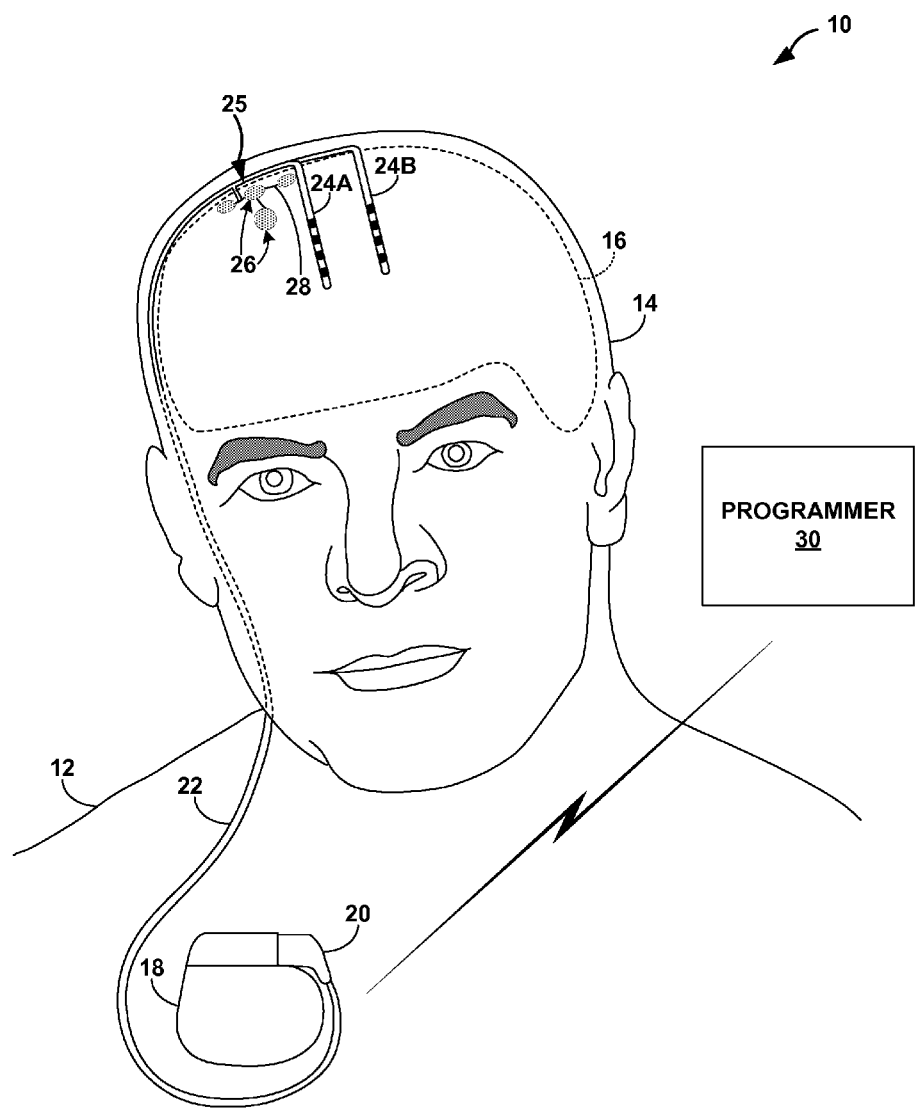
FIG. 1 is a conceptual diagram illustrating an embodiment of a deep brain stimulation system that includes a biosignal detection module to detect a volitional patient input to control therapy.

Medical devices are useful for treating or otherwise control various patient conditions or disorders. In some cases, medical devices may be used to deliver therapy to patients having conditions or disorders that cannot be effectively treated with diet, exercise, lifestyle changes, orally ingested pharmaceuticals, or any other treatment regimen. Medical devices may be configured to deliver therapies such as electrical stimulation, drug delivery or internally or externally generated sensory cues (or "stimuli") that reduce or eliminate the patient condition or disorder. Depending upon the type of therapy delivered by the medical device, the medical device may be implanted in the patient for chronic therapy delivery (e.g., longer than a temporary, trial basis).

In some cases, a medical device may be programmed with different therapy parameters. The therapy parameters may be selected to address a particular patient's condition during the initial stages of therapy implementation, as well as during follow-up visits to a clinician's office. In some cases, the clinician may create multiple programs that each have different therapy parameters selected by the clinician. These programs may also be referred to as therapy "parameter sets." During a trial stage, the patient may evaluate the different therapy programs to identify the therapy programs that provide the most efficacious treatment relative to the other tested programs.

Based on the trial stage or other considerations, the clinician and/or patient may select one or more therapy programs for use by the medical device during chronic therapy delivery. In some cases, the patient may be given the freedom to select one or more therapy programs with which to delivery therapy or to increase or decrease therapy parameters as needed to increase the efficacy of therapy. For example, if an electrical stimulator is implanted within the patient, the patient may increase or decrease a stimulation parameter, such as the current or voltage amplitude of the stimulation, within a predetermined range. The clinician or the manufacturer of the electrical stimulator may select the predetermined range. In the case of electrical stimulation therapy, the range is typically selected such that the electrical stimulation does not harm the patient.

In the therapy systems described herein, a patient may adjust one or more aspects of therapy via a volitional patient input that is detected via a biosignal within the brain. In one embodiment, the biosignal is generated within the brain in response to a volitional thought, such as a thought relating to a particular muscle movement (e.g., facial twitching, moving a finger, etc.). Thus, the patient may provide the input by moving a muscle, performing a particular calculation within his head, or any other volitional thought that produces a detectable electrical signal within the brain. The volitional patient input is associated with a particular therapy adjustment action, such as initiating therapy, deactivating therapy or increasing or decreasing a therapy parameter.

The one or more biosignals that are used to detect the volitional patient input may be selected to be unique, i.e., differentiated from other brain signals that are unrelated to the volitional patient input, in order to minimize the number of false positives. A false positive may be, for example, detecting the biosignal when the patient did actually provide the volitional patient input. In such a case, the biosignal may be incorrectly detected, e.g., because of its similarity to another brain signal unrelated to the volitional patient input.

The therapy systems described herein include a biosignal detection module that detects the biosignal generated within the brain based on the patient input. The biosignal detection module provides feedback to a therapy device (or a "therapy module"), which adjusts therapy accordingly. In this way, the systems described herein eliminate the need for a patient to interact with an external programming device in order to adjust therapy. However, in some embodiments, the biosignal feedback system described herein may be used to control therapy in addition to an external programmer.

The biosignal detection module may employ an algorithm to suppress false positives, i.e., the adjustment of therapy in response to a brain signal that is not the biosignal indicative of the patient input. For example, in addition to selecting a unique biosignal, the biosignal detection module may implement an algorithm that identifies particular attributes of the biosignal (e.g., certain frequency characteristics of the biosignal) that are unique to the patient input. As another example, the biosignal detection module may monitor the characteristics of the biosignal in more than one frequency band, and correlate a particular pattern in the power of the brain signal within two or more frequency bands in order to determine whether the brain signal is indicative of the volitional patient input. As another example, the volitional patient input may include a pattern of volitional actions or thoughts that generate a specific pattern of brain signals or a brain signal including specific attributes that may be identified by the biosignal detection module. The specific attributes may include, for example, a pattern in the amplitude waveform of a bioelectrical brain signal, or a pattern or behavior of the frequency characteristics of the bioelectrical brain signal, and so forth.

In some embodiments, a biosignal detection module acquires a bioelectrical signal from within one or more regions of a patient's brain using implanted or external electrodes. The bioelectrical signal may include an electroencephalogram (EEG) signal, electromyogram (EMG) signal, electrocorticogram (ECoG) signal, field potentials within the motor cortex or other regions of the brain, or combinations thereof.

In one embodiment, the biosignal detection module acquires an EEG signal from within one or more regions of a patient's brain using one or more electrodes placed on the head or implanted within the patient. An EEG signal indicates the electrical activity within a brain of a patient. The biosignal detection module may be implanted within the patient or may be carried external to the patient. A processor within the biosignal sensing module, therapy module or another part of the therapy system determines whether the monitored EEG signal includes the biosignal via many suitable techniques. As described in further detail below, in one embodiment, a processor processes the EEG signal by tuning into, or extracting, a specific frequency band from the EEG signal that contains information pertinent to a volitional patient input. The biosignal may then be a component of the EEG signal within the extracted frequency band.

The therapy systems described herein do not directly alter therapy based upon symptoms of the patient's condition or disease. Rather, the therapy systems implement a biosignal that provides feedback to a therapy module, where the biosignal is nonsymptomatic. That is, the biosignal is unrelated to a condition of the patient's disease. Furthermore, the biosignal results from a volitional patient input, rather than an incidental electrical signal within the patient's brain that the patient did not voluntarily or intentionally generate. Thus, the detection of a volitional patient input that indicates a desired to therapy adjustment action differs from involuntary neuronal activity that may be caused by the patient's condition (e.g., a tremor or a seizure). In some embodiments, symptomatic physiological changes may be detected by the system and used as feedback to increase therapy efficacy. However, these symptomatic changes in the brain are not the biosignals detected by the biosignal detection module that allow the patient direct control over therapy. Instead, the biosignal detection module detects a particular biosignal within the patient's brain that results from a volitional input, thereby allowing the patient to control one or more aspects of therapy by voluntarily causing a detectable physiological change within the brain.

The patient 12 may wish to adjust therapy for many different reasons. For example, if the therapy system is implemented to control pain, patient may initiate therapy delivery or increase/decrease therapy delivery parameters as the patient's pain level changes. As another example, if therapy system 10 is used to treat or control seizures, and patient 12 sees an aura or another indication that a seizure is likely to occur, patient 12 may provide volitional input to initiate or increase therapy delivery in an attempt to stop the onset of the seizure.

In some embodiments, once the therapy system is implemented in the patient, the therapy system may be programmed to link biosignals within the brain to specific volitional patient inputs with specific patient activities, from which the type of therapy adjustment may be determined. In other embodiments, the therapy system may be programmed to link biosignals within the brain to specific therapy adjustment actions. As described in further detail below, the biosignals may be determined during a learning mode, and a clinician or a computing device may associate certain biosignals with respective therapy adjustment actions. In one embodiment, a therapy system may be preprogrammed to perform certain therapy adjustments upon detecting biosignals for certain actions. For example, if the patient wishes to cease therapy delivery, the patient may produce a volitional thought directed to moving his eyes down. In other embodiments, the therapy system may combine the biosignal detection with a secondary input means, such as tapping an accelerometer, or a combination of biosignals prior to implementing the indicated therapy adjustment action.

In some cases, the patient may produce biosignals in a particular pattern generated from a sequence of voluntary thought in order to minimize unwanted changes in therapy from biosignals detected during normal daily activity. Example sequences may involve multiple eye movements, facial expressions, limb movements, and any other thought sequences that are detectable by the biosignal sensing module.

The learning mode is not only useful during the initial programming of the therapy system, but also throughout implementation of the chronic therapy system. For example, after the initial programming of the therapy system, the patient may change certain correlations between a particular biosignal and an associated therapy action, remove a correlated activity that is commonly used by the patient or add a new correlation between a biosignal and a therapy action. In some cases, the clinician may prompt the patient to reenter the learning mode after a change in therapy is produced or because of a progression in the patient's disease.

The patient may realize many advantages when controlling therapy with biosignals that are based on volitional thought. For example, the therapy system described herein eliminates the need for the patient to carry an external programmer throughout the day in order to take therapy actions, such as changing programs, increasing amplitude, and turning the therapy on and off. Carrying the programmer may be burdensome on the patient, and may be an indiscreet mechanism for adjusting therapy, which may cause social discomfort to the patient. In addition, the patient may not be able to use the external programmer during certain activities such as swimming, showering, driving, exercising, or when the patient's hands are occupied. In this manner, a therapy systems in which biosignals within a patient's brain provide input to adjust therapy may provide additional safety and security to the patient by permitting the patient to adjust therapy in many circumstances in which an external programmer may not be practical.

Biosignal detection may also be beneficial for patients unable or unwilling to use an external programmer. For example, the therapy systems described herein may be useful for blind patients, who may find it difficult to manipulate an external programmer. The therapy systems described herein may also be useful for elderly patients, who may find it difficult to master the use of the external programmer due to a relative complicated user interface. In addition, biosignal detection may allow patients with movement disorders, such as Parkinson's disease, to initiate therapy when a motion impairment condition (e.g., tremor) may be too severe to provide an input to an external programmer. Additional advantages are also provided by the biosignal reception therapy system described herein, depending upon the embodiment implemented to the patient.

The therapy system described herein may receive biosignals to control any type of therapy. Example therapies include, but are not limited to, pain therapy, spinal cord stimulation (SCS), deep brain stimulation (DBS), peripheral nerve stimulation (PNS), peripheral nerve field stimulation (PNFS), incontinence therapy, gastric stimulation, and pelvic floor stimulation. These and other therapies may be directed toward treating conditions such as chronic pain, incontinence, sexual dysfunction, obesity, migraine headaches, Parkinson's disease, depression, epilepsy, seizures, or any other neurological disease. Additional conditions and diseases may also be treated by detecting biosignals to control delivery of a therapy. While therapy described herein is preferably directed to human patients, the therapy may be applied to non-human patients as well.

FIG. 1 is a conceptual diagram illustrating an example DBS system 10, which includes implantable medical device (IMD) 18, lead extension 22, leads 24A and 24B, and electrode array 25. IMD 18 includes a therapy module that delivers electrical stimulation therapy to patient 12 via leads 24A and 24B, as well as a biosignal detection module that detects one or more biosignals indicative of one or more volitional patient inputs relating to therapy adjustment actions. As described in further detail below, the biosignal detection module provides feedback to the therapy module to control one or more aspects of therapy delivery.

IMD 18 is implanted in patient 12. Implanted lead extension 22 is coupled to IMD 18 via connector 20. Lead extension 22 traverses from the implant site of IMD 18 within a chest cavity of patient 12, and along the neck of patient 12 to cranium 14 of patient 12 to access brain 16. Leads 24A and 24B (collectively "leads 24") are implanted within the right and left hemispheres, respectively, of patient 12 in order deliver electrical stimulation to one or more regions of brain 16, which may be selected based on the patient condition or disorder controlled by DBS system 10. Electrode array 25 includes a plurality of electrodes 26, which are carried by lead 28, to detect biosignals within brain 16 that result from a volitional patient thought. External programmer 30 wireless communicates with IMD 18 as needed to provide or retrieve therapy information. While patient 12 is generally referred to as a human patient, other mammalian or non-mammalian patients are also contemplated.

Although leads 24 are shown in FIG. 1 as being coupled to a common lead extension 22, in other embodiments, leads 24 may be coupled to IMD 18 via separate lead extensions or directly to the therapy module. Leads 24 may deliver electrical stimulation to treat any number of neurological disorders or diseases. Example neurological disorders may include depression, dementia, obsessive-compulsive disorder, and movement disorders, such as Parkinson's disease, spasticity, and epilepsy. DBS is also useful for treating other patient conditions, such as migraines and obesity.

Leads 24 may be implanted within a desired location of brain 16 through respective holes in cranium 14. Leads 24 may be placed at any location within brain 16 such that the electrodes of the leads are capable of providing electrical stimulation to targeted tissue during treatment. Electrical stimulation generated from the signal generator (not shown) within the therapy module of IMD 18 may be configured to treat a variety of disorders and conditions. Example locations for leads 24 within brain 16 may include the pedunculopontine nucleus (PPN), thalamus, basal ganglia structures (e.g., globus pallidus, substantia nigra, subthalamic nucleus), zona inserta, fiber tracts, lenticular fasciculus (and branches thereof), ansa lenticularis, and/or the Field of Forel (thalamic fasciculus). In the case of migraines, leads 24 may be implanted to provide stimulation to the visual cortex of brain 16 in order to reduce or eliminate migraine headaches afflicting patient 12. In addition, as described in further detail below, electrode array 25 or sensing electrodes of leads 24 may be positioned to monitor an EEG from within the visual cortex of brain. In the case of obesity or compulsive-eating disorders, leads 24 may be placed to provide stimulation to provide negative feedback to patient 12, e.g., stimulating a sensory cortex of brain 16 to cause patient 12 to believe food tastes bad. However, the target therapy delivery site may depend upon the patient condition or disorder being treated.

The electrodes of leads 24 are shown as ring electrodes. Ring electrodes are commonly used in DBS applications because they are simple to program and are capable of delivering an electrical field to any tissue adjacent to leads 24. In other embodiments, the electrodes of leads 24 may have different configurations. For examples, the electrodes of leads 24 may have a complex electrode array geometry that is capable of producing shaped electrical fields. The complex electrode array geometry may include multiple electrodes (e.g., partial ring or segmented electrodes) around the perimeter of each lead 24, rather than one ring electrode. In this manner, electrical stimulation may be directed to a specific direction from leads 24 to enhance therapy efficacy and reduce possible adverse side effects from stimulating a large volume of tissue. In some embodiments, a housing of IMD 18 may include one or more stimulation and/or sensing electrodes. In alternative examples, leads 24 may be have shapes other than elongated cylinders as shown in FIG. 1. For example, leads 24 may be paddle leads, spherical leads, bendable leads, or any other type of shape effective in treating patient 12.

IMD 18 includes a therapy module that generates the electrical stimulation delivered to patient 12 via leads 24. A signal generator (not shown), within IMD 18 produces the stimulation in the manner defined by the therapy parameters selected by the clinician and/or patient 12. Generally the signal generator is configured to produce electrical pulses to treat patient 12. However, the signal generator of IMD 18 may be configured to generate a continuous wave signal, e.g., a sine wave or triangle wave. In either case, IMD 18 generates the electrical stimulation therapy for DBS according to therapy parameters selected at that given time in therapy.

In the embodiment shown in FIG. 1, IMD 18 generates the electrical stimulation according to one or more therapy parameters, which may be arranged in a therapy program (or a parameter set). The therapy program includes a value for a number of parameters that define the stimulation. For example, the therapy parameters may include voltage or current pulse amplitudes, pulse widths, pulse rates, pulse frequencies, electrode combinations, and the like. IMD 18 may store a plurality of programs. During a trial stage in which IMD 18 is evaluated to determine whether IMD 18 provides efficacious therapy to patient 12, the stored programs may be tested and evaluated for efficacy. During chronic therapy in which IMD 18 is implanted within patient 12 for delivery of therapy on a non-temporary basis, patient 12 may select the programs for delivering therapy. For example, the different programs may provide more efficacious therapy during different activities, different times of the day, and so forth. Thus, patient 12 may modify the value of one or more parameters within a single given program or switch between programs in order to alter the efficacy of the therapy as perceived by patient 12.

IMD 18 may include a memory to store one or more therapy programs, instructions defining the extent to which patient 12 may adjust therapy parameters, switch between programs, or undertake other therapy adjustments. Patient 12 may generate additional programs for use by IMD 18 via external programmer 30 at any time during therapy or as designated by the clinician. Patient 12 may also generate additional therapy programs by adjusting the one or more therapy parameters with volitional inputs that are detected via biosignals within brain 16. In particular, a biosignal detection module within IMD 18 detects the biosignals via electrode array 25. If patient 12 modifies a therapy program, patient 12 may provide input to therapy system 10 that causes the therapy module within IMD 18 to save the parameters as a new therapy program for later use.

Generally, IMD 18 is constructed of a biocompatible material that resists corrosion and degradation from bodily fluids. IMD 18 may be implanted within a subcutaneous pocket close to the stimulation site. Although IMD 18 is implanted within a chest cavity of patient 12 in the embodiment shown in FIG. 1, in other embodiments, IMD 18 may be implanted within cranium 14. While IMD 18 is shown as implanted within patient 12 in FIG. 1, in other embodiments, IMD 18 may be located external to the patient. For example, IMD 18 may be a trial stimulator electrically coupled to leads 24 via a percutaneous lead during a trial period. If the trial stimulator indicates therapy system 10 provides effective treatment to patient 12, the clinician may implant a chronic stimulator within patient 12 for long term treatment.

Electrode array 25 is implanted within cranium 14 of patient 12 and positioned to detect an electroencephalogram (EEG) signal within a particular region of patient's brain 16, which may depend upon the type of volitional patient input that generates the biosignal. Electrode array 25 may be surgically implanted under the dura matter of brain 16 or within the cerebral cortex of brain 16 via a burr hole in a skull of patient 12. In some cases, electrodes 26 implanted closer to the target region of brain 16 may help generate an EEG signal that provides more useful information than an EEG generated via a surface electrode array because of the proximity to brain 16. The EEG signal that is generated from implanted electrode array may also be referred to as an ECoG.

Electrode array 25 may be positioned to detect an EEG signal within a motor cortex, a sensory motor strip, the visual cortex (e.g., the occipital cortex), cerebellum or the basal ganglia of brain 16. Volitional patient inputs in the form of muscle movement, e.g., movement of a finger, arm, leg or facial muscle, may generate detectable changes (i.e., detectable biosignal) in the EEG signal from within the motor cortex. Volitional patient input in the form of eye movement, e.g., moving eyes in certain directions, opening eyes or closing eyes, may generate a detectable biosignal in the occipital cortex of brain 16.

Electrode array 25 is coupled to IMD 18 via lead extension 22 or another lead extension. In other embodiments, electrode array 25 may communicate with IMD 18 via wireless telemetry, rather than a wired connection as shown in FIG. 1. For example, electrode array 25 may be integrated into a separate biosignal detection module that includes a housing that includes a processor, memory, telemetry interface, battery, and any other component necessary for the sensing signal to transfer data. Data may be transferred to IMD 18 and/or programmer 30. An embodiment including a separate biosignal detection module is shown and described with reference to FIG. 2.

Electrode array 25 includes lead 28 that is coupled to electrodes 26. Electrodes 26 are shown as implanted under the skin covering cranium 14, but the electrodes may be implanted between cranium 14 and brain 16 (e.g., under the dura), within brain 16 (e.g., "deep brain"), or externally over the skin in alternative embodiments. Electrodes 26 are configured to receive electrical signals produced from neuronal activity within brain 16. These signals may make up EEG, and, accordingly are referred to as "EEG signals." In any case, electrodes 26 are positioned around brain 16 in order to receive signals emanating from targeted locations within the brain. The targeted locations may be those locations in which the patient thought relating to the volitional patient input occurs.

The biosignal detection module within IMD 18 is configured to monitor an EEG from within a region of brain 16 and determine whether the EEG signal includes the biosignal that is generated when patient 12 provides the volitional input relating to the therapy adjustment action. While an EEG signal within the motor cortex is primarily referred to throughout the remainder of the application, in other embodiments, therapy system 10 may detect a biosignal within other regions of brain 16. The motor cortex is defined by regions within the cerebral cortex of brain 16 that are involved in the planning, control, and execution of voluntary motor functions, such as walking and lifting objects. Typically, different regions of the motor cortex control different muscles. For example, different "motor points" within the motor cortex may control the movement of the arms, trunk, and legs of patient. Accordingly, electrodes array 25 may be positioned to sense the EEG signals within particular regions of the motor cortex, e.g., at a motor point that is associated with the movement of the arms, depending on the type of volitional patient input system 10 is configured to recognize as a therapy adjustment input.

EEG is typically a measure of voltage differences between different parts of brain 16, and, accordingly, electrode array 25 may include two or more electrodes. The sensing module within IMD 18 may then measure the voltage across at least two electrodes of array 25. Although four electrodes are shown in FIG. 1, in other embodiments, electrode array 25 may include any suitable number of electrodes. One or more of the electrodes 26 may act as a reference electrode for determining the voltage difference of one or more regions of brain 16. Lead 28 coupling electrodes 26 to IMD 18 may, therefore, include a separate, electrically isolated conductor for each electrode 26.

Electrodes 26 of array 25 may be positioned to detect EEG signals from one or more select regions within brain 16, which may depend upon the type of volitional patient thoughts that are used as an input to control therapy. Electrode array 25 may only include those electrodes 26 necessary to the operation of system 10 to minimize the number of devices placed on or implanted within patient 12. Electrodes 26 may be placed to detect biosignals within more than one region of brain 16 if therapy system 10 is configured to recognize more than one biosignal to control therapy.

In other embodiments, electrode array 25 may be carried by at least one of leads 24A and/or 24B instead of or in addition to electrodes 26 that are separate from leads 24A and 24B. This configuration of electrode array 25 may be useful when the relevant biosignals when are generated near the same region of brain 16 as the target therapy delivery site.

Programmer 30 is an external computing device that the user, i.e., the clinician and/or patient 12, uses to communicate with IMD 18. For example, programmer 30 may be a clinician programmer that the clinician uses to communicate with IMD 18. Alternatively, programmer 30 may be a patient programmer that allows patient 12 to view and modify therapy parameters. The clinician programmer may include more programming feature than the patient programmer. In other words, more complex or sensitive tasks may only be allowed by the clinician programmer to prevent the untrained patient from making undesired changes to IMD 18.

Programmer 30 may be a hand-held computing device with a display viewable by the user and a user input mechanism that can be used to provide input to programmer 30. For example, programmer 30 may include a small display screen (e.g., a liquid crystal display or a light emitting diode display) that provides information to the user. In addition, programmer 30 may include a keypad, buttons, a peripheral pointing device or another input mechanism that allows the user to navigate through the user interface of programmer 30 and provide input. If programmer 18 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 30 may be a touch screen that allows the user to provide input directly to the user interface shown on the display. The user may use a stylus or their finger to provide input to the display. An embodiment of programmer 30 is described below with reference to FIGS. 8 and 12.

In other embodiments, programmer 30 may be a larger workstation or a separate application within another multi-function device. For example, the multi-function device may be a cellular phone or personal digital assistant that can be configured to an application to simulate programmer 30. Alternatively, a notebook computer, tablet computer, or other personal computer may enter an application to become programmer 30 with a wireless adapter connected to the personal computer for communicating with IMD 18.

When programmer 30 is configured for use by the clinician, programmer 30 may be used to transmit initial programming information to IMD 18. This initial information may include system 10 hardware information such as the type of leads 24 and the electrode arrangement, the position of leads 24 within brain 16, the configuration of electrode array 25, initial programs having therapy parameters, and any other information the clinician desires to program into IMD 18. Programmer 30 may also be capable of completing any functional tests (e.g., measuring the impedance of electrodes 26 or the electrodes of leads 24A and 24B) the clinician desires to complete before starting therapy and sending patient 12 home.

The clinician also uses programmer 30 to program IMD 18 with initial stimulation programs, defined as programs that define the therapy delivered by IMD 18. During a programming session, the clinician may determine one or more therapy programs that may provide effective therapy to patient 12. Patient 12 may provide feedback to the clinician as to the efficacy of the specific program being evaluated. Once the clinician has identified one or more programs that may be beneficial to patient 12, patient 12 may continue the evaluation process and determine which program best alleviates the condition of patient 12. Programmer 30 may assist the clinician in the creation/identification of therapy programs by providing a methodical system of identifying potentially beneficial therapy parameters.

As described in further detail below, a clinician may also set or modify the parameters of the biosignal detection module within IMD 18 with the aid of programmer 30 during an initial programming session or at a later time. For example, programmer 30 may help associate a biosignal that is generated within brain 16 with one or more volitional patient inputs (e.g., movement of a particular muscle). Programmer 30 may also help correlate a biosignal with a particular therapy activity (e.g., a pulse amplitude adjustment) or modify the correlation between a particular biosignal and a therapy activity. In addition, programmer 30 may help the clinician identify which electrodes 26 provide the most useful detection of the biosignals, because some electrodes 26 may acquire a better EEG signals than other electrodes 26.

Programmer 30 may also be configured for use by patient 12. When configured as the patient programmer, programmer 30 may have limited functionality in order to prevent patient 12 from altering critical functions or applications that may be detrimental to patient 12. In this manner, programmer 30 may only allow patient 12 to adjust certain therapy parameters or set an available range for a particular therapy parameter. Programmer 30 may also include a learning mode that automatically correlates biosignals detected by the biosignal detection module within IMD 18 to activities of patient 12 or desired therapy adjustments. Programmer 30 may also provide an indication to patient 12 when therapy is being delivered, when biosignals have triggered a change in therapy, or when IMD 18 or when the power source within programmer 30 or IMD 18 need to be replaced or recharged.

Whether programmer 30 is configured for clinician or patient use, programmer 30 may communicate to IMD 18 or any other computing device via wireless communication. Programmer 30, for example, may communicate via wireless communication with IMD 18 using radio frequency (RF) telemetry techniques known in the art. Programmer 30 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 30 may also communicate with another programming or computing device via exchange of removable media, such as magnetic or optical disks, or memory cards or sticks. Further, programmer 30 may communicate with IMD 18 and other another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 have be fitted with an external medical device, rather than IMD 18 that is coupled to percutaneous leads. In addition, electrode array 25 may be placed over the scalp of patient 12 to monitor the relevant EEG signals, and coupled to the external medical device or a separate biosignal detection module.

In some embodiments of the therapy systems described herein, the therapy system may provide feedback to patient 12 to indicate that the volitional input was received. For example, the sensory cortex of brain 16 may be stimulated to provide the sensation of a visible light. Other forms of sensory feedback are also possible, such as an audible sound or a somatosensory cue. In some embodiments, programmer 30 may include a feedback mechanism, such an LED, another display or a sound generator, which indicates that the therapy system received the volitional patient input and that the appropriate therapy adjustment action was taken.

Figure 2A:
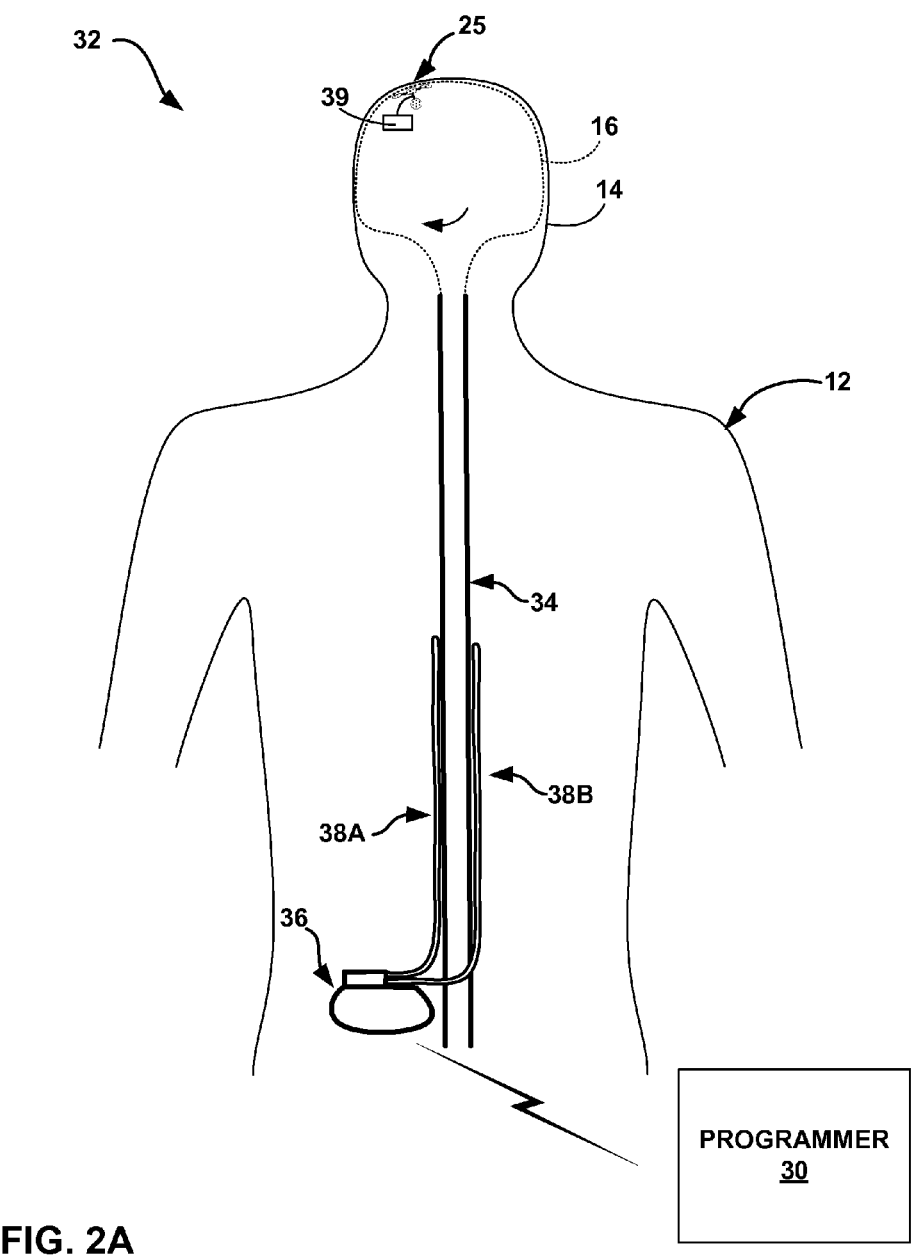
FIG. 2A is a conceptual diagram illustrating an embodiment of a spinal cord stimulation system with a biosignal detection module used by the patient to control therapy.

FIG. 2A is a conceptual diagram illustrating an example spinal cord stimulation (SCS) system 32, which includes IMD 36 configured to deliver stimulation to spinal cord 34, leads 38A and 38B (collectively "leads 38") coupled to IMD 36, electrode array 25 positioned to detect an EEG signal within a motor cortex of brain 16 of patient 12, and biosignal detection module 39. SCS system 32 is substantially similar to therapy system 10 of FIG. 1. However, IMD 36 is configured to deliver electrical stimulation therapy to spinal cord 34 of patient 12 and biosignal detection module 39 is separate from IMD 36 and implanted within cranium 14.

Leads 38 are implanted adjacent to spinal cord 34 such that electrodes (not shown) of each of leads 38 are capable of delivering electrical stimulation to the desired area of spinal cord 34. Although leads 38 are positioned to achieve bilateral stimulation of spinal cord 34, in other embodiments, leads 38 may be positioned to achieve unilateral stimulation.

SCS therapy may be used, for example, to reduce pain experienced by patient 12. Although IMD 36 is described for purposes of illustration, various embodiments of this disclosure also may be applicable to external therapy modules that reside outside the patient's body, and deliver stimulation therapy using one of more implanted leads deployed via a percutaneous port. For example, the functions of IMD 36 may be combined with the functions of programmer 30 and implemented in a single external device that provides stimulation therapy. In other embodiments, leads 38 may be placed to deliver stimulation to other target sites within patient 12, where the target sites depend on the patient condition treated by therapy system 32. Also, in some embodiments, IMD 36 may be a leadless microstimulator in which electrodes are carried on or near an electrical stimulator housing.

Just as with IMD 18 of FIG. 1, IMD 36 delivers electrical stimulation therapy to patient 12 via electrodes of leads 38. IMD 36 may deliver stimulation therapy to patient 12 according to a program group containing plurality of programs for a single symptom area, such as a number of leg pain programs. The plurality of programs for the single area may be a part of a program group for therapy. In addition, multiple groups may target similar areas of patient 12. IMD 36 may have different program parameters for each of the leg pain programs based on a position of patient 12, an activity rate of patient 12, or other patient parameters. Programs in a group may be delivered simultaneously or on a time-interleaved basis, either in an overlapping or non-overlapping manner.

Patient 12 may adjust the SCS therapy delivered by IMD 36 by providing a volitional patient input that results in a biosignal within brain 16 that is detectable by biosignal detection module 39. Just as with therapy system 10 of FIG. 1, the volitional patient input may be a volitional thought, such as thoughts relating to volitional actions. Examples of volitional actions include, but not limited to, eye blinking, facial muscle twitches, finger movements, or any other thought that is manifested in an electrical signal from brain 16. In addition, biosignals detectable by biosignal detection module 39 may be indicative of volitional patient thoughts that do not result in physical movement or even directed to movement. For example, the mere thought of moving a finger may generate a detectable EEG signal within the motor cortex of brain 16. As another example, patient 12 may perform a particular mathematical calculation or perform another focused task that generates a detectable EEG signal within another region of brain 16. In this manner, patient 12 may adjust stimulation therapy without physically interacting with programmer 30.

Biosignal detection module 39 and electrode array 25 are implanted within a cranium 14 of patient 12. Biosignal detection module 39 is described in further detail below with reference to FIG. 7. In general, the embodiment of biosignal detection module 39 shown in FIG. 2A wirelessly communicates with IMD 36 using any suitable wireless communication technique, such as RF communication techniques. In one embodiment, biosignal detection module 39 includes a processor that processes the EEG signals monitored via electrode array 25 and determines when the biosignal is detected. Upon detecting the biosignal that is indicative of the patient input, the processor within biosignal detection module 39 may generate a therapy adjustment indication that is transmitted IMD 36 via wireless telemetry techniques. In response to receiving the therapy adjustment indication, IMD 36 may adjust therapy accordingly. Different therapy adjustment indications may be generated. For example, biosignal detection module 39 may generate a therapy adjustment indication that initiates therapy, another indication that deactivates therapy, and other indications that increment or decrement a therapy parameter (e.g., pulse rate).

In another embodiment, biosignal detection module 39 monitors the EEG signal and transmits the EEG signal to IMD 36, which includes a processor to determine when the biosignal is detected. In other embodiments of SCS system 32, biosignal detection module 39 may be integrated in a common housing with IMD 36, and electrode array 25 may be coupled to IMD 36 via a wired connection, such as a lead or lead extension that tunneled to IMD 36.

System 32 is not limited to the combination of leads 38 shown in FIG. 2A. For example, system 10 may include only a single lead or more than two leads implanted proximate to spinal cord 34. In addition, the disclosure further contemplates the use of one or more leadless microstimulators carrying or integrating electrodes in the stimulator housing. Furthermore, the invention is not limited to the delivery of SCS therapy. For example, one or more leads 38 may extend from IMD 36 to the brain (not shown) of patient 12. As further examples, one or more leads 38 may be implanted proximate to the pelvic nerves (not shown) or stomach (not shown), and IMD 36 may deliver stimulation therapy to treat incontinence, obesity, gastroparesis. IMD 36 may also be used for peripheral nerve stimulation. In some embodiments, IMD 36 is configured to deliver functional electrical stimulation (FES) or transcutaneous electrical stimulation (TENS) of a muscle or muscle group of patient 12 in order to help initiate movement or help patient 12 control movement of a limb or other body part. Alternatively, IMD 36 may take the form of one or more microstimulators implanted within a muscle of patient 12.

Leads 38 may be any type of leads commonly used in SCS therapy. For example, leads 38 may be paddle leads or leads with ring electrodes. Alternatively, leads 38 may have a complex electrode array geometry with multiple electrodes (e.g., partial ring or segmented electrodes) around the perimeter of each lead. In this manner, the clinician may select the specific electrodes necessary for therapy without stimulating unnecessary tissue. The complex electrode array geometry of leads 38 may also be described as partial ring electrodes when IMD 36 is capable of delivering electrical stimulation to specific sides of leads 38. In this manner, therapy parameters may be selected to offset any inaccurate implantation of the leads or lead migration over time.

Figure 2B:
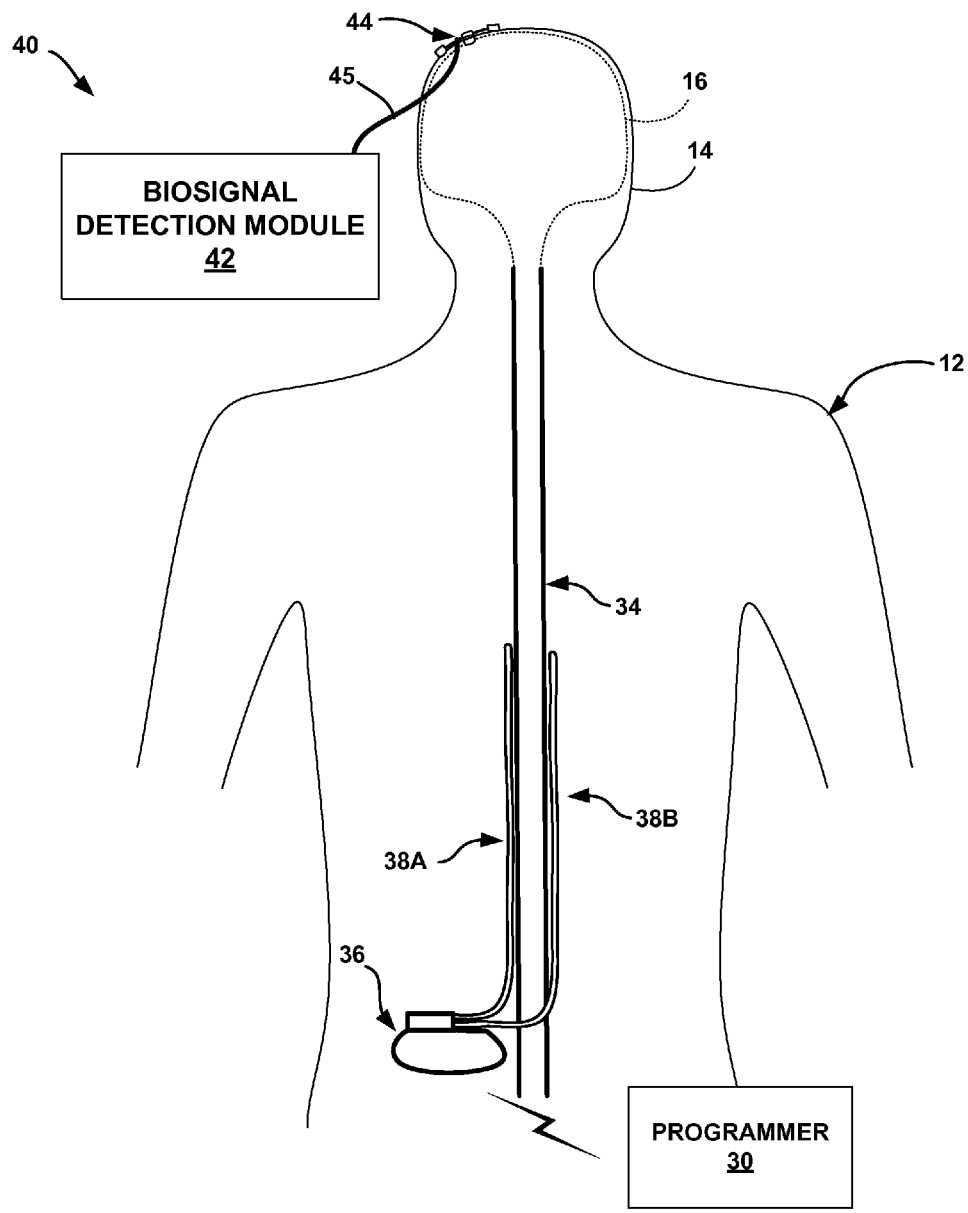
FIG. 2B is a conceptual diagram illustrating another embodiment of a spinal cord stimulation system that includes an external biosignal detection module.

FIG. 2B is a conceptual diagram illustrating another embodiment of an SCS system 40, which includes IMD 36 configured to deliver stimulation to spinal cord 34, leads 38 coupled to IMD 36, and external biosignal detection module 42 coupled to surface electrode array 44. Rather than an implanted biosignal detection module 39 and implanted electrode array 25, as in the SCS system 32 of FIG. 2A, SCS system 40 detects the relevant biosignals indicative of a therapy adjustment command via external biosignal detection module 42 coupled to surface electrode array 44. Biosignal detection module 42 is substantially similar to biosignal detection module 39 of FIG. 1, but is carried externally to patient 12. For example, patient 12 may wear biosignal detection module 42 on a belt.

Electrode array 44 is positioned on a surface of cranium 16 of patient 12 proximate to a motor cortex of brain 16. Electrodes of array 44 are positioned to detect an EEG signal within a motor cortex of brain 16 of patient 12. Electrodes of electrode array 44 are electrically coupled to biosignal detection module 42 via lead 45.

The position of electrodes of array 44 may depend upon the type of volitional patient input that is detected. For example, different muscle movements may produce biosignals within different regions of patient's brain 16. In one embodiment, the clinician may initially place array 44 based on the general location of the target region (e.g., it is known that the motor cortex is a part of the cerebral cortex, which may be near the front of the patient's head) and adjust the location of array 44 as necessary to capture the electrical signals from the target region. In another embodiment, the clinician may rely on the "10-20" system, which provides guidelines for determining the relationship between a location of an electrode and the underlying area of the cerebral cortex.

In addition, the clinician may locate the particular location within the motor cortex for detecting movement of the specific limb (e.g., a finger, arm or leg) via any suitable technique. In one embodiment, the clinician may also utilize an imaging device, such as magnetoencephalography (MEG), positron emission tomography (PET) or functional magnetic resonance imaging (fMRI) to identify the region of the motor cortex of brain 16 associated with movement of the specific limb. In another embodiment, the clinician may map EEG signals from different parts of the motor cortex and associate the EEG signals with movement of the specific limb in order to identify the motor cortex region associated with the limb. For example, the clinician may attach electrode array 44 over the region of the motor cortex that exhibited the greatest detectable change in EEG signal at the time patient 12 actually moved the limb involved in the volitional patient input.

Rather than requiring patient 12 to manually input an indication of a therapy adjustment, e.g., via programmer 30, SCS system 40 automatically provides the indication to IMD 36 upon the detection of a biosignal by biosignal detection module 42. Biosignal detection module 42 detects EEG signals of patient 12 and processes the signal to determine whether the EEG signal is indicative of a volitional patient input, i.e., whether the biosignal is present. Upon detecting the biosignal, transmits a signal to IMD 36 via wireless telemetry techniques.

In other embodiments, a therapy system described herein may include an IMD 36 positioned to deliver therapy to treat migraine headaches. For example, an IMD may include a therapy module that generates and delivers electrical stimulation to appropriate areas of brain 16 (e.g., the occipital nerves) to reduce or eliminate migraine headaches. When patient 12 perceives a migraine headache, the patient may generate a biosignal detectable by biosignal detection module 42 or an implanted biosignal detection module 39 (FIG. 2A) that indicates stimulation therapy should begin. In this manner, the therapy system may provide on-demand therapy to control a migraine without the need for external programmer 30.

Figure 3:
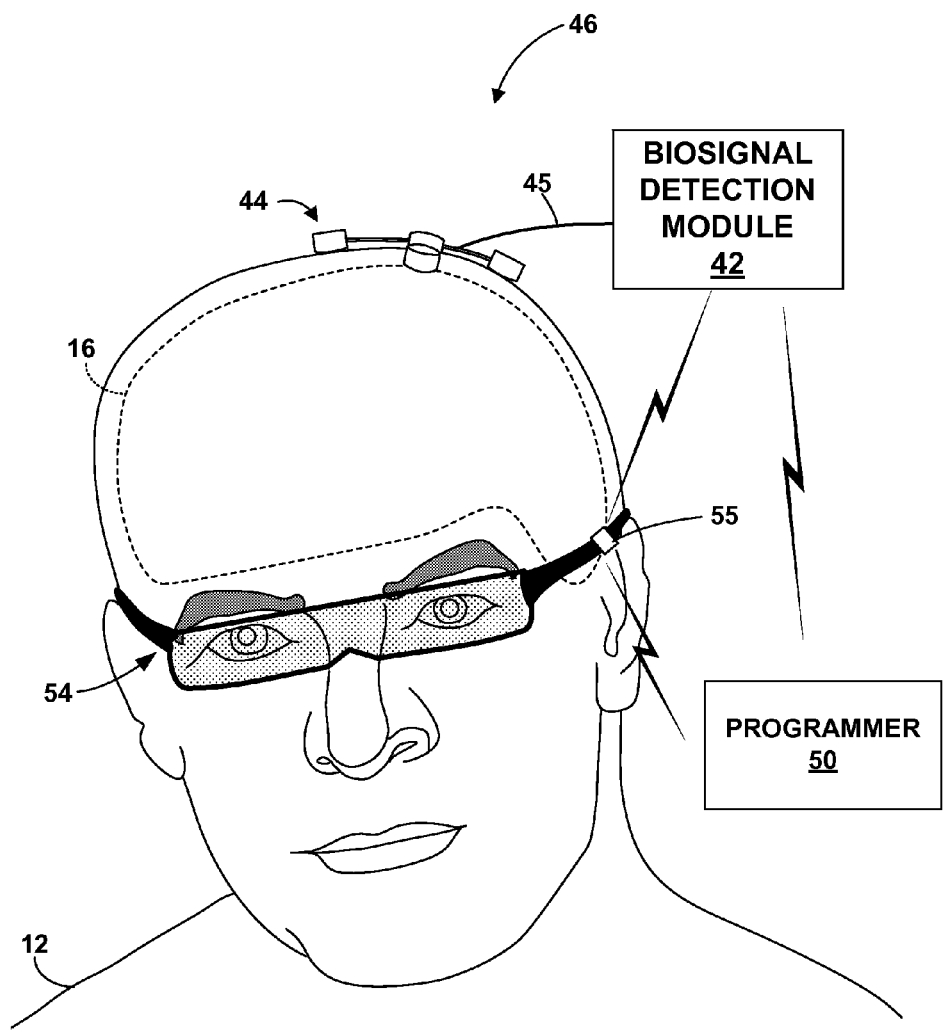
FIG. 3 is a conceptual diagram illustrating an embodiment of a sensory cue system that includes a biosignal detection module.

FIG. 3 is a conceptual diagram illustrating another embodiment of a therapy system 46, which includes biosignal detection module 42 coupled to external surface electrode array 44 via lead 45, external cue device 54, and programmer 30. Therapy system 46 may be useful for controlling a movement disorder or a neurodegenerative impairment of patient 12, such as, but not limited to muscle control, motion impairment or other movement problems, such as rigidity, bradykinesia, rhythmic hyperkinesia, nonrhythmic hyperkinesia, akinesia. In some cases, the movement disorder may be a symptom of Parkinson's disease. However, the movement disorder may be attributable to other patient conditions or diseases.

Therapy system 46 may improve the performance of motor tasks by patient 12 that may otherwise be difficult. These tasks include at least one of initiating movement, maintaining movement, grasping and moving objects, improving gait associated with narrow turns, and so forth. The therapy module of system 46, i.e., external cue device 54, generates and delivers a sensory cue, such as a visual, auditory or somatosensory cue, to patient 12 in order to help control some conditions of a movement disorder. External cues may disrupt certain neural impulses to allow patient 12 to carry on normal activities. For example, visual stimulation may treat gait freeze associated with Parkinson's disease, nausea, motor impairment, or any other neurological disorder. For example, if patient 12 is prone to gait freeze or akinesia, a sensory cue may help patient 12 initiate or maintain movement. In other embodiments, external cues delivered by external cue device 54 may be useful for controlling other movement disorder conditions, such as, but not limited to, rigidity, bradykinesia, rhythmic hyperkinesia, and nonrhythmic hyperkinesia.

Rather than requiring patient 12 to manually activate external cue device 54 by interacting with a handheld device or another external device, therapy system 46 automatically activates external cue device 54 upon the detection of a biosignal by biosignal detection module 42. In some cases, therapy system 42 also automatically deactivates external cue device 54 based on a biosignal. As described with reference to FIG. 2A, biosignal detection module 42 detects a biosignal that is generated within brain 16 after patient 12 provides the volitional input, e.g., upon the generation of a particular volitional thought by patient 12. The volitional input may include, for example, thought of initiating a particular movement by patient 12. In one embodiment, patient 12 may open and close his eyes in a particular pattern that includes a defined interval between each eye opening and closing. The volitional patient input may be customized to patient 12. For example, if patient 12 has a movement disorder, the patient input may be selected such that patient 12 may provide the input despite an impairment in movement. If patient 12 has difficult lifting his arm, for example, the volitional patient input that provides the biosignal for adjusting therapy should avoid patient inputs that require patient 12 to lift his arm.

The biosignal is associated with a therapy adjustment, such as initiating the delivery of an external cue by external cue device 54. Thus, upon detecting the biosignal, biosignal detection module 42 transmits a signal to receiver 55 of external cue device 54, and a controller within external cue device 54 controls the generation and delivery of a sensory cue to patient 12 in order to help control the movement disorder. Accordingly, biosignal detection module 42 includes a telemetry module that is configured to communicate with receiver 55. Examples of local wireless communication techniques that may be employed to facilitate communication between biosignal detection module 42 and receiver 55 of device 54 include RF communication according to the 802.11 or Bluetooth specification sets, infrared communication, e.g., according to the IrDA standard, or other standard or proprietary telemetry protocols. Automatic activation of external cue device 54 upon the detection of the biosignal may help provide patient 12 with better control and timing of external cue device 54 by eliminating the need for patient 12, who exhibits some difficulty with movement, to initiate the device 54.

In the embodiment shown in FIG. 3, external cue device 54 is shown as a pair of glasses configured to deliver visual stimulation therapy to patient 12 when necessary. For example, external cue device 54 may include one or more light-emitting diode (LED) positioned at specific locations around the frame of therapy module 54 but within the peripheral vision of patient 12. Alternatively, external cue device 54 may include a display configured to produce a light, image, or other visual aid over the portion of external cue device 54 that is visible to patient 12. Similar to a head-up-display, patient 12 may see the light pattern in therapy external cue device 54 and the visual therapy from the light pattern may help alleviate symptoms of the movement disorder.

As described in further detail with reference to FIG. 6, external cue device 54 includes the necessary components to generate and deliver an external cue to patient 12. For example, external cue device 54 includes a processor, memory, telemetry circuit to communicate with programmer 30 and biosignal detection module 42, light generating circuit, power source, and any other circuitry necessary for operation. In the embodiment shown in FIG. 3, external cue device 54 is embodied as a pair of glasses, which provides a discreet device for providing therapy to patient 12. In one embodiment, external cue device 54 takes the form of the Parkinson's goggles developed by the University of Cincinnati, which includes a liquid crystal display (LCD) screen that shows a patient a tile pattern on the floor to help a patient walk. Other embodiments of therapy module 54 may include a hat with a brim extending from the brow of patient 12, a hand-held device, a display wearable around a necklace, or any other device that may quickly be used by patient 12. These and other embodiments of therapy module 54 are contemplated.

Visual cues, auditory cues or somatosensory cues may have different effects on patient 12. For example, in some patients with Parkinson's disease, an auditory cue may help the patients grasp moving objects, whereas somatosensory cues may help improve gait and general mobility. Although external cue device 54 is shown as an eyepiece worn by patient 12 in the same manner as glasses, in other embodiments, external cue device 54 may have different configurations. For example, if an auditory cue is desired, an external cue device may take the form of an ear piece (e.g., an ear piece similar to a hearing aid or head phones). As another example, if a somatosensory cue is desired, an external cue device may take the form of a device worn on the patient's arm or legs (e.g., as a bracelet or anklet), around the patient's waist (e.g., as a belt) or otherwise attached to the patient in a way that permits the patient to sense the somatosensory cue. A device coupled to the patient's wrist, for example, may provide pulsed vibrations.

Programmer 30 allows patient 12 or the clinician to program external cue device 54 and/or biosignal detection module 42 at the beginning of therapy or at anytime during therapy. Programmer 30 may be configured to program desired therapy parameters into external cue device 54. Example therapy parameters for external cue device 54 may include light patterns, light color, light pulse width and pulse rate, and any other parameters that govern the visual stimulation therapy delivered by external cue device 54.

In some embodiments, biosignal detection module 42 and external cue device 54 may be incorporated in a common housing. Furthermore, although external biosignal detection module 42 and external electrode array 44 are shown in FIG. 3, in other embodiments, system 46 may include an implanted biosignal detection module 39 and electrode array 25, as shown in FIG. 2A with respect to SCS therapy system 32.

Sensory cues may also be delivered via an IMD. Thus, in other embodiments of system 46, an IMD may deliver electrical stimulation to a sensory location within brain 16 to cause the perception of an external stimulus. For example, an IMD may deliver stimulation to a visual cortex of brain 16 in order to simulate a visual cue. No external therapy module may be necessary and the sensory cue would be imperceptible to any other person near patient 12.

Figure 4:
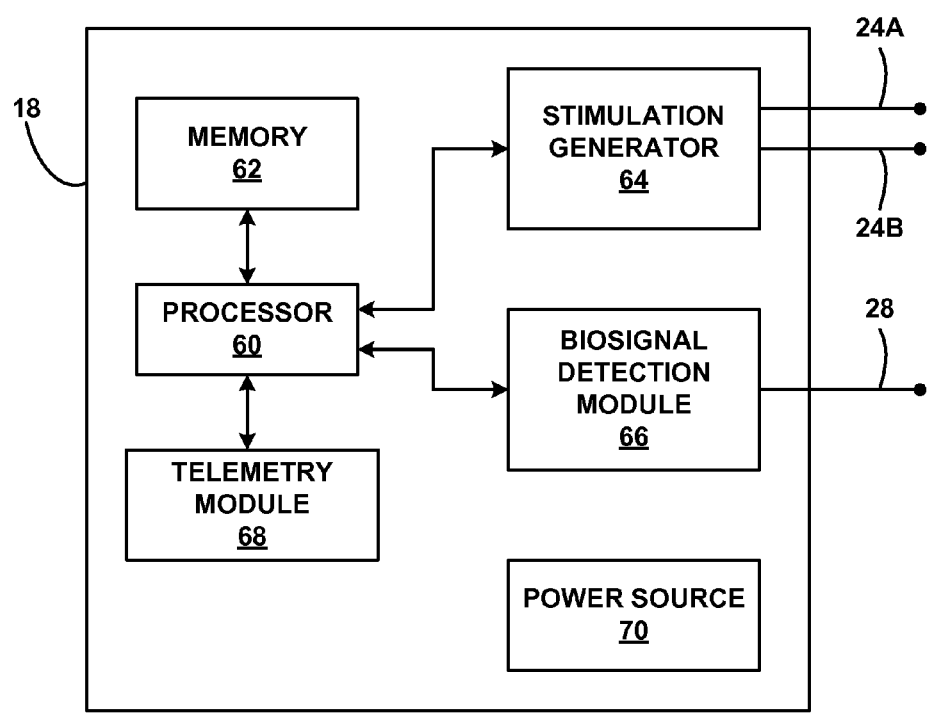
FIG. 4 is functional block diagram illustrating components of an embodiment of an electrical stimulator.

FIG. 4 is functional block diagram illustrating components of an exemplary IMD 18 (FIG. 1). In the example of FIG. 4, IMD 18 generates and delivers electrical stimulation therapy to patient 12. IMD 18 includes processor 60, memory 62, stimulation generator 64, biosignal detection module 66, telemetry circuit 68, and power source 70. Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store instructions for execution by processor 60, such as, but not limited to, therapy programs, information identifying biosignals (e.g., an amplitude of an EEG signal or a template of an EEG signal waveform), and any other information regarding therapy of patient 12. Therapy information may be recorded for long-term storage and retrieval by a user, and adjustment of the therapy parameters, programs, or biosignal correlations. Memory 62 may include separate memories for storing instructions, biosignal information, activities, and therapy parameters. In some embodiments, memory 62 stores program instructions that, when executed by processor 60, cause IMD 18 and processor 60 to perform the functions attributed to them herein.

Processor 60 controls stimulation generator 64 to deliver electrical stimulation therapy via one or more leads 24. An exemplary range of electrical stimulation parameters likely to be effective in deep brain stimulation, for example, are listed below. Other ranges of therapy parameters may be used when the therapy is directed to other tissues. While stimulation pulses are described, stimulation signals may be of any forms such as sine waves or the like.

1. Frequency: between approximately 0.5 Hz and approximately 500 Hz, such as between approximately 5 Hz and 250 Hz, or between approximately 70 Hz and approximately 120 Hz.

2. Amplitude: between approximately 0.1 volts and approximately 50 volts, such as between approximately 0.5 volts and approximately 20 volts, or approximately 5 volts. In other embodiments, a current amplitude may be defined as the biological load in the voltage is delivered.

3. Pulse Width: between approximately 10 microseconds and approximately 5000 microseconds, such as between approximately 100 microseconds and approximately 1000 microseconds, or between approximately 180 microseconds and approximately 450 microseconds.

An exemplary range of electrical stimulation parameters likely to be effective in treating chronic pain, e.g., when applied to spinal cord 34 from IMD 36 as in FIGS. 2A and 2B, are listed below. While stimulation pulses are described, stimulation signals may be of any forms such as sine waves or the like.

1. Frequency: between approximately 0.5 Hz and approximately 500 Hz, such as between approximately 5 Hz and approximately 250 Hz, or between approximately 10 Hz and approximately 50 Hz.

2. Amplitude: between approximately 0.1 volts and approximately 50 volts, such as between approximately 0.5 volts and 20 volts, such as about 5 volts. In other embodiments, a current amplitude may be defined as the biological load in the voltage is delivered.

3. Pulse Width: between approximately 10 microseconds and approximately 5000 microseconds, such as between approximately 100 microseconds and approximately 1000 microseconds, or between approximately 180 microseconds and approximately 450 microseconds.

Processor 60 may include a microprocessor, a controller, a digital signal processor (DSP), an application specific integrated circuit (ASIC), a field-programmable gate array (FPGA), discrete logic circuitry, or the like. Processor 60 controls biosignal detection module 66, which receives EEG signals from brain 16 of patient 12 via electrodes 26 and lead 28. Processor 60 or a separate processor within biosignal detection module 66 analyzes the EEG signals to determine whether the EEG signals include the biosignal indicative of a volitional patient input. That is, processor 60 or a processor within biosignal detection module 66 determines when the EEG signal indicates that patient 12 provided the volitional input because the volitional input produces a detectable change in the EEG signal, i.e., detects the biosignal. While the processing of the EEG signals from biosignal detection module 66 are primarily described with reference to processor 60, in other embodiments, biosignal detection module 66 may independently identify a biosignal from patient 12 and notify processor 60 when such biosignal has been produced.

If processor 60 detects the biosignal, processor 60 may generate a therapy adjustment indication. The therapy adjustment indication may be a value, flag, or signal that is stored or transmitted to indicate patient 12 provided a volitional thought indicative of a desired adjustment to therapy. Processor 60 may transmit the therapy adjustment indication to a medical device via telemetry module 68, which, in response, may adjust therapy accordingly. In this way, the biosignal from an EEG signal may be a control signal for adjusting therapy. In some embodiments, processor 60 may record the therapy adjustment indication in memory 62 for later retrieval and analysis by a clinician. For example, movement indications may be recorded over time, e.g., in a loop recorder, and may be accompanied by the relevant EEG signal.

Processor 60 may compare the EEG signals from biosignal detection module 66 with previously determined biosignal threshold or templates stored in memory 62 in order to determine whether the EEG signal includes the biosignal. In this manner, processor 60 determines when to adjust therapy from the biosignals. Embodiments of signal processing techniques are described below with reference to FIGS. 10A and 10B.

As various examples of signal processing techniques that processor 60 may employ to determine whether the EEG signal includes the biosignal, the EEG signals may be analyzed for voltage, amplitude, temporal correlation or frequency correlation with a template signal, or combinations thereof. For example, the instantaneous or average amplitude of the EEG signal from within the occipital cortex over a period of time may be compared to an amplitude threshold. In one embodiment, when the amplitude of the EEG signal from within the occipital cortex is greater than or equal to the threshold value, processor 60 may control stimulation generator 64 to deliver stimulation to patient 12.

As another example, a slope of the amplitude of the EEG signal over time or timing between inflection points or other critical points in the pattern of the amplitude of the EEG signal over time may be compared to trend information. A correlation between the inflection points in the amplitude waveform of the EEG signal or other critical points and a template may indicate the EEG signal includes the biosignal indicative of patient input. Processor 60 may implement an algorithm that recognizes a trend of the EEG signals that characterize the biosignal. If the trend of the EEG signals matches or substantially matches the trend template, processor 60 may control stimulation generator 64 to deliver stimulation to patient 12.

As another example, processor 60 may perform temporal correlation by sampling the waveform generated by the EEG signal with a sliding window and comparing the waveform with a stored template waveform that is indicative of the biosignal. For example, processor 60 may perform a correlation analysis by moving a window along a digitized plot of the amplitude waveform of EEG signals at regular intervals, such as between about one millisecond to about ten millisecond intervals, to define a sample of the EEG signal. The sample window is slid along the plot until a correlation is detected between the waveform of the template and the waveform of the sample of the EEG signal defined by the window. By moving the window at regular time intervals, multiple sample periods are defined. The correlation may be detected by, for example, matching multiple points between the template waveform and the waveform of the plot of the EEG signal over time, or by applying any suitable mathematical correlation algorithm between the sample in the sampling window and a corresponding set of samples stored in the template waveform.

Different frequency bands are associated with different activity in brain 16. One embodiment of the frequency bands is shown in Table 1:

TABLE 1

Frequency bands

| Frequency (f) Band Hertz (Hz) | Frequency Information |
|---|---|
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

It is believed that some frequency band components of the EEG signal may be more revealing of particular activities than other frequency components. For example, the alpha band from Table 1 may be more revealing of a rest state, in which patient 12 is awake, but not active, than the beta band. EEG signal activity within the alpha band may attenuate with eye opening or an increase or decrease in physical activity. A higher frequency band, such as the beta or gamma bands, may also attenuate with an increase or decrease in physical activity. Accordingly, the type of volitional patient input may affect the frequency band of the EEG signal in which a biosignal associated with the patient input is detected. The relative power levels within the high gamma band (e.g., about 100 Hz to about 200 Hz) of an EEG signal, as well as other bioelectric signals, has been shown to be both an excellent biomarker for motion intent, as well as flexible to human control. That is, a human patient 12 may control activity within the high gamma band with volitional thoughts.

The power level within the selected frequency band may be more revealing of the biosignal than a time domain plot of the EEG signal. Thus, in some embodiments, an analog tune amplifier may tune a monitored EEG signal to a particular frequency band in order to detect the power level (i.e., the signal strength) within a particular frequency band, such as a low frequency band (e.g., the alpha or delta frequency band from Table 1), the power level with a high frequency band (e.g., the beta or gamma frequency bands in Table 1) or both the power within the low and high frequency bands. The biosignal indicative of the volitional patient input may be the strength of the EEG signal within the tuned frequency band, a pattern in the strength of the EEG signal over time, a ratio of power levels within two or more frequency bands, the pattern in the power level within two or more frequency bands (e.g., an increase in power level within the alpha band correlated with a decrease in a power level within the gamma band or high gamma band) or other characteristics of one or more frequency components of the EEG signal. The power level of the EEG signal within the tuned frequency band, the pattern of the power level over time, or the ratio of power levels may be compared to a stored value in order to determine whether the biosignal is detected.

Figure 15:
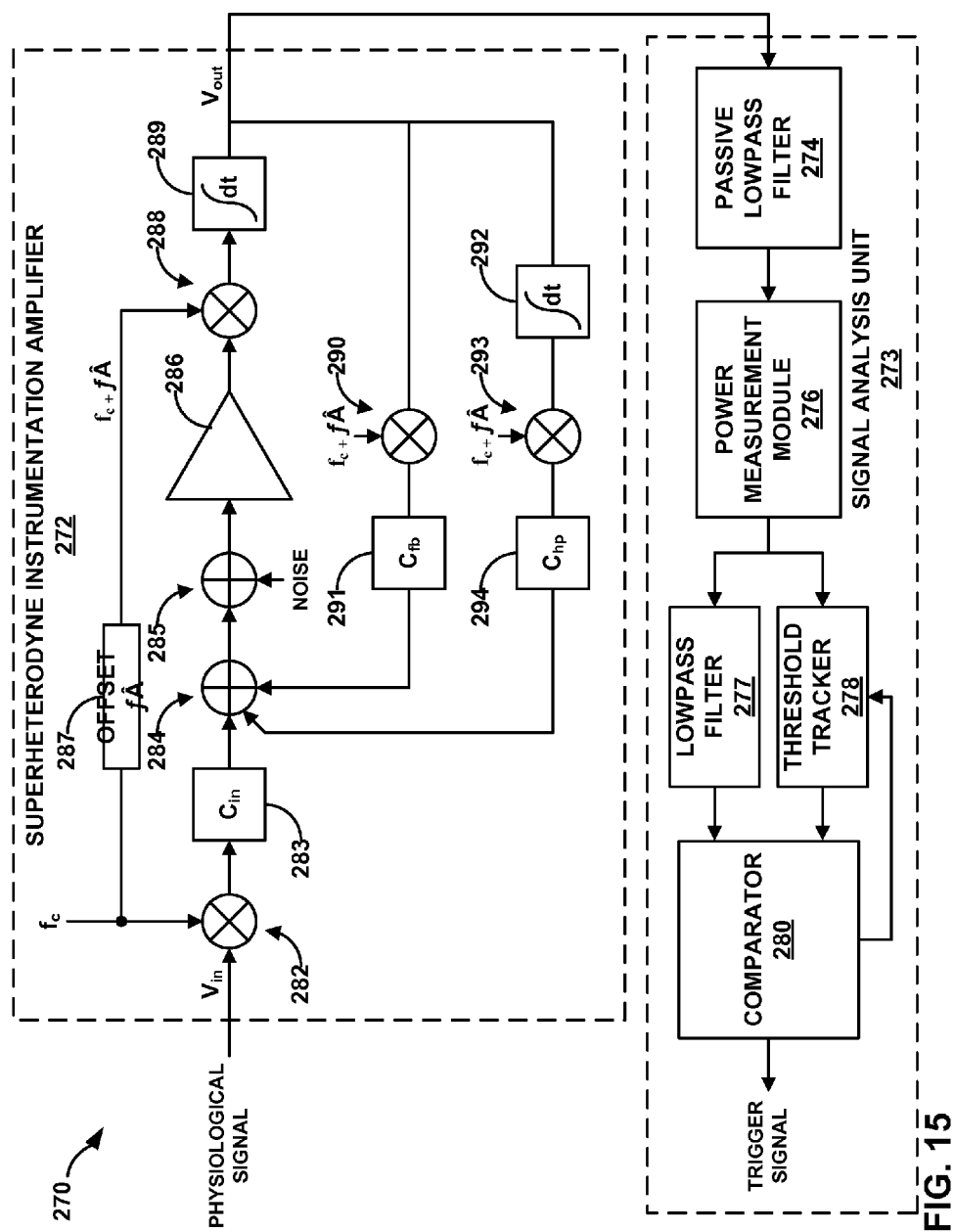
FIG. 15 is a block diagram illustrating an exemplary frequency selective signal monitor that includes a chopper-stabilized superheterodyne amplifier and a signal analysis unit.

The amplifier may be included within processor 60 of IMD 18, a processor of biosignal detection module 66 or another processor used to detect a biosignal from a monitored EEG signal. FIG. 15 illustrates an embodiment of an amplifier circuit that may be used to detect the biosignal, which may be included within biosignal detection module 66 or processor 60. The amplifier circuit shown in FIG. 15 uses limited power to monitor a frequency in which a desired biosignal is generated. If the amplifier is disposed within biosignal detection module 66, processor 60 may control biosignal detection module 66 to tune into the desired frequency band, which may be identified during a learning mode or simply by clinician experience and specific biosignal research information.

In general, the EEG signal may be analyzed in the frequency domain to compare the power level of the EEG signal within one or more frequency bands to a threshold or to compare selected frequency components of an amplitude waveform of the EEG signal to corresponding frequency components of a template signal. The template signal may indicate, for example, a trend in the power level within one or more frequency bands that indicates patient 12 generated a volitional input that resulted in the biosignal indicative of patient input to adjust therapy. Specific examples of techniques for analyzing the frequency components of the EEG signal are described below with reference to FIG. 10B.

Telemetry module 68 in IMD 18, as well as telemetry modules in other devices described herein, such as programmer 30, may accomplish communication by RF communication techniques. In addition, telemetry module 68 may communicate with programmer 30 via proximal inductive interaction of IMD 18 with external programmer 30. Accordingly, telemetry module 68 may send information to external programmer 30 on a continuous basis, at periodic intervals, or upon request from the implantable stimulator or programmer. Processor 60 controls telemetry module 68 to send and receive information. Wireless telemetry may be accomplished by RF communication or proximal inductive interaction of IMD 18 with external programmer 30.

Power source 70 delivers operating power to various components of IMD 18. Power source 70 may include a small rechargeable or non-rechargeable battery and a power generation circuit to produce the operating power. Recharging may be accomplished through proximal inductive interaction between an external charger and an inductive charging coil within IMD 18. In some embodiments, power requirements may be small enough to allow IMD 18 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 18 whenever measurements are needed or desired.

IMD 36 (FIG. 2A) is substantially similar to IMD 18 shown in FIG. 4, but does not include biosignal detection module 66. The telemetry module of IMD 36 is configured to communicate with the separately housed biosignal detection module 39 via wireless telemetry techniques, such as RF communication.

Figure 5:
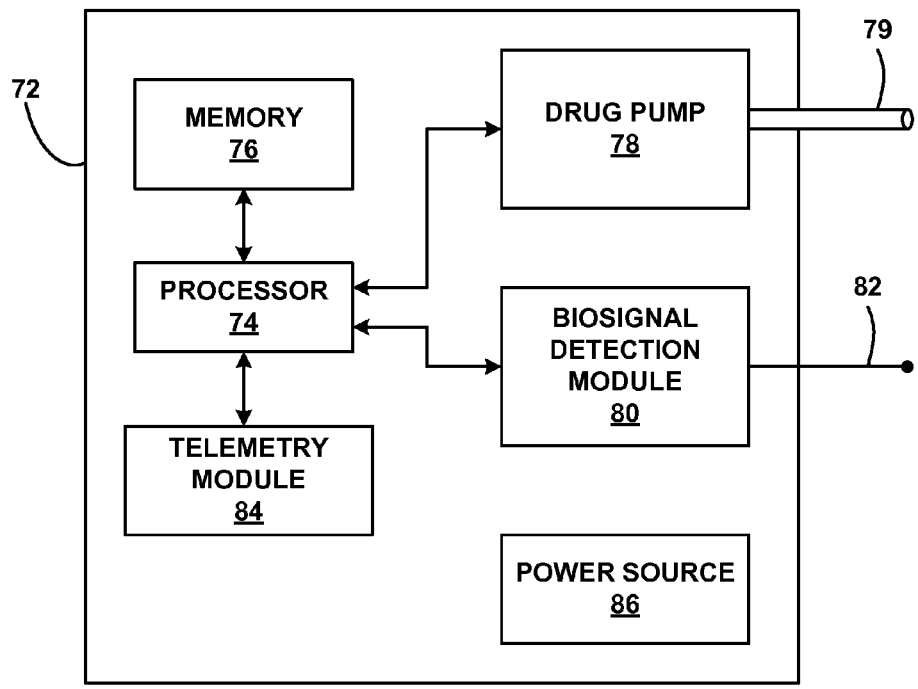
FIG. 5 is functional block diagram illustrating components of an embodiment of a drug pump.

FIG. 5 is functional block diagram illustrating components of an exemplary medical device 72 with drug pump 78. Medical device 72 may be used in therapy system 10 (FIG. 1) or other therapy systems in which volitional patient input generates a biosignal within the patient's brain that is used as feedback to adjust therapy delivered by medical device 72. Medical device 72 may be implanted or carried externally to patient 12. As shown in FIG. 5, medical device 72 includes processor 74, memory 76, drug pump 78, biosignal detection module 80, telemetry module 84, and power source 86. Drug pump 78 delivers a specific quantity of a pharmaceutical agent to a desired tissue within patient 12 via catheter 79 implanted within patient 12. In some embodiments, medical device 72 may include stimulation generator for producing electrical stimulation in addition to delivering drug therapy.

Medical device 72 may be directed towards chronic pain therapy, but medical device 72 may deliver a drug (i.e., a pharmaceutical agent) or another fluid to any location within patient 12. Processor 74, memory 76, biosignal detection module 80, telemetry module 84, and power source 86 may all be similar to processor 60, memory 62, biosignal detection module 66, telemetry module 68, and power source 70, respectively, of FIG. 4. Processor 74 controls the operation of medical device 72 with the aid of instructions that are stored in memory 76, which is similar to the control of IMD 18. For example, the instructions may dictate the bolus size of a drug that is delivered to patient 12 when biosignal detection module 80 detects the biosignal indicative of volitional patient input relating to a therapy adjustment action. When processor 74 receives an indication from biosignal detection module 80 that patient 12 has provided a volitional input that is associated with a drug delivery adjustment action (e.g., initiation of drug delivery, increase or decrease in bolus size or frequency or deactivation of drug delivery), processor 74 controls drug pump 78 to take the action associated with the biosignal. As mentioned above, the biosignal may be indicative of some kind of volitional patient activity, such as eye movement, blinking, facial movements, or other volitional thoughts.

Biosignal detection module 80 is substantially similar to biosignal detection module 66 of FIG. 4. Biosignal detection module 80 may include an analog circuit that amplifies and monitors a specific frequency band of the electrical signal from brain 16. Memory 76 may store the biosignal information that determines which frequency bands of the EEG signal to monitor and what thresholds in signal amplitude indicate a successful biosignal. Biosignal detection module 80 may also be connected to an electrode array, such as implanted array 25 (FIG. 1) or external array 44 (FIG. 2B), via lead 82 or via wireless telemetry.

In alternative embodiments of IMD 18 and medical device 72, the respective biosignal detection modules 66, 80 may be disposed in a separate housing. For example, in FIG. 2A, therapy system 32 includes a separate IMD 36 and biosignal detection module 39. In such embodiments, biosignal detection modules 66, 80 may communicate wirelessly with the medical device, thereby eliminating the lead or other elongated member that couples the biosignal detection module to IMD 18 or medical device 72. In some embodiments, biosignal detection module 66 may include an amplifier circuit (e.g., the circuit shown in FIG. 15) for monitoring and identifying biosignals within brain 16 with a relatively minimal amount of battery power consumption.

Figure 6:
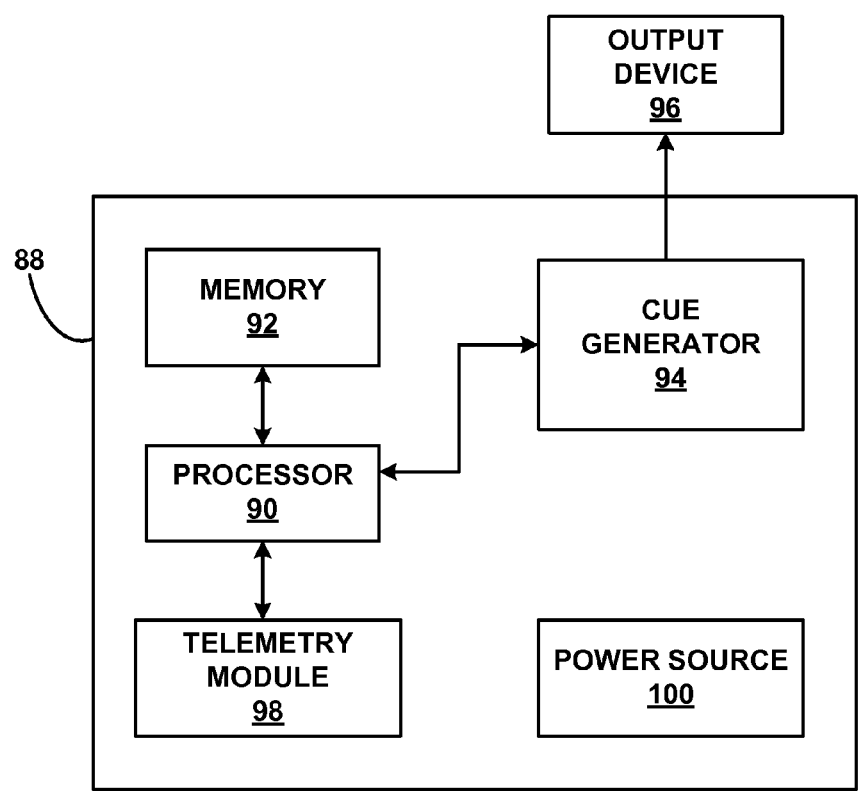
FIG. 6 is functional block diagram illustrating components of an exemplary sensory cue device.

FIG. 6 is a functional block diagram illustrating components of an embodiment of therapy module 88, which may be incorporated into an external cue device, such as device 54 of FIG. 3. In addition, therapy module 88 may have similar components to IMD 18. For example, processor 90, memory 92, telemetry module 98, and power source 100 may be similar to processor 60, memory 62, telemetry module 68, and power source 70 of IMD 18.

As shown in FIG. 6, therapy module 88 includes cue generator 94 coupled to output device 96. Upon receiving a control signal from biosignal detection module 42 that indicates biosignal detection module 42 detected the biosignal indicative of a volitional patient input, processor 90 controls cue generator 94 to generate a sensory cue and deliver the cue to patient via output device 96. As previously described, biosignal detection module 42 detects and identifies biosignals produced by patient 12 when the patient provides an indication that a therapy adjustment is desired. For example, patient 12 may create a volitional thought to generate a biosignal when the patient needs a visual cue from output device 96. Processor 90 acts upon the identification of the biosignal and controls cue generator 94 to generate a sensory cue in accordance with the type of biosignal identified. In this manner, patient 12 may generate multiple types of biosignals through volitional thought in order to elicit multiple types of sensory cues from therapy module 88.

Output device 96 may be any device configured to create a stimulus. As previously described, example stimuli may include light, sound, vibration, any combination thereof or other visual, auditory or somatosensory cues. As described in FIG. 3, output device 96 may be an LED mounted on the inside of the frame of therapy device 18 or an LCD screen. In some embodiments, therapy module 88 may include multiple output devices 96 that each deliver a different stimuli.

As described above, wireless telemetry in therapy module 88 may be needed to communicate with biosignal detection module 42, programmer 30, or another device. Wireless communication may be accomplished by RF communication or proximal inductive interaction of therapy module 88 with the other wireless device. Accordingly, telemetry module 98 may send or receive information from biosignal detection module 42 and external programmer 56 on a continuous basis, at periodic intervals, or upon request from the implantable stimulator or programmer. Processor 90 controls telemetry module 98 to send and receive information.

Cue generator 94 includes the electrical circuitry needed to generate the stimulus delivered by output device 96. For example, cue generator 94 may modulate the color of light emitted by output device 96, the intensity of light emitted by output device 96, the frequency of sound waved delivered by output device 96, or any other therapy parameter of the output device. Processor 90 may interrogate therapy parameter instructions stored in memory 92 before controlling any specific stimulus generated by cue generator 94.

In some embodiments, output device 96 may be a display that is capable of producing patterns of light, images, or other representations on the output device itself or projected onto another surface for patient 12 to see. In this manner, the visual cue, or stimulus, may be more complex than a simple light or sound. For example, output device 96 may deliver a sequence of colored shapes that causes the symptoms of the patient 12 condition to subside. Alternatively, one or more words, numbers, symbols or other graphics may produce a desired affect to treat patient 12. When output device 96 is a display, the output device may be embodied as a LCD, head-up display, LCD projection, or any other display technology available to the manufacturer of therapy module 88.

Figure 7:
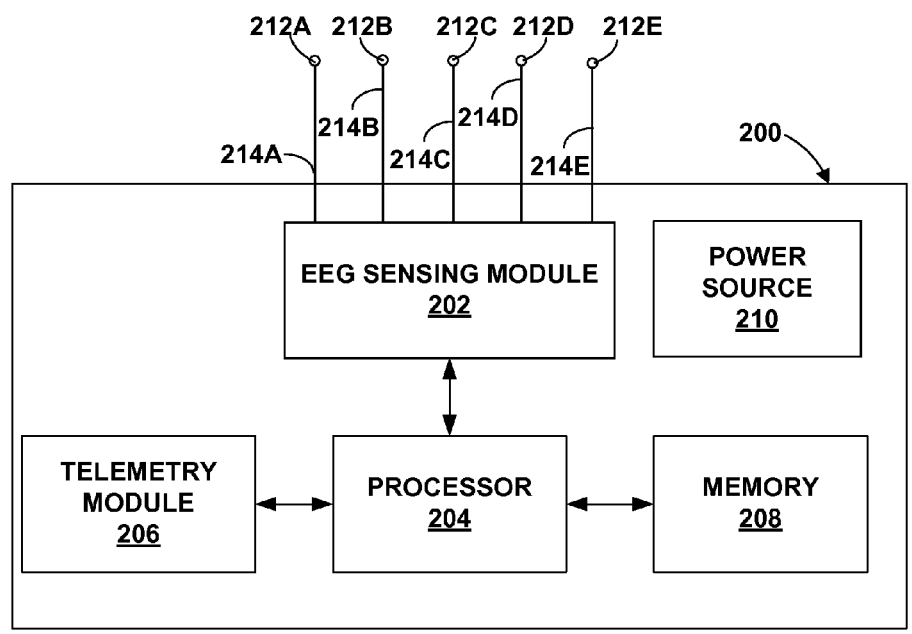
FIG. 7 is a functional block diagram illustrating components of biosignal detection module that is separate from a therapy module.

FIG. 7 is a functional block diagram illustrating components of biosignal detection module 200 that is separate from a therapy module. For example, biosignal detection module 200 may be an implanted biosignal detection module 39 of FIG. 2A or an external biosignal detection module 42 of therapy system 32 of FIGS. 2A and 3. Biosignal detection module 200 provides feedback to control a medical device, such as IMD 36 or external cue device 54. Biosignal detection module 200 includes EEG sensing module 202, processor 204, telemetry module 206, memory 208, and power source 210. Biosignal detection modules 66, 80 of IMD 18 and medical device 72, respectively, may also include some components of biosignal detection module 200 shown in FIG. 7, such as EEG sensing module 202 and processor 204.

EEG sensing module 202, processor 204, as well as other components of biosignal detection module 200 that require power may be coupled to power source 210. Power source 210 may take the form of a rechargeable or non-rechargeable battery. EEG sensing module 202 monitors an EEG signal within brain 16 of patient 12 via electrodes 212A-E, which may be, for example, a part of electrode array 25 (FIG. 2A) or electrode array 44 (FIG. 3). Electrodes 212A-E are coupled to EEG sensing module 202 via leads 214A-E, respectively. Two or more of leads 214A-E may be bundled together (e.g., as separate conductors within a common lead body) or may include separate lead bodies.

Processor 204 may include a microprocessor, a controller, a DSP, an ASIC, a FPGA, discrete logic circuitry or the like. Processor 204 controls telemetry module 206 to exchange information with programmer 30 and/or a medical device, such as IMD 36. Telemetry module 206 may include the circuitry necessary for communicating with programmer 30 or an implanted or external medical device. Examples of wireless communication techniques that telemetry module 206 may employ include RF communication, infrared communication, e.g., according to the IrDA standard, or other standard or proprietary telemetry protocols.

In some embodiments, biosignal detection module 200 may include separate telemetry modules for communicating with programmer 30 and the medical device. Telemetry module 206 may operate as a transceiver that receives telemetry signals from programmer 30 or a medical device, and transmits telemetry signals to the programmer 30 or medical device. For example, processor 204 may control the transmission of the EEG signals from EEG sensing module 202 to a medical device. As another example, processor 204 may determine whether the EEG signal monitored by EEG sensing module 202 includes the biosignal, and upon detecting the presence of the biosignal, processor 204 may transmit a control signal to the medical device via telemetry module 206, where the control signal indicates the type of therapy adjustment indicated by the biosignal.

In some embodiments, processor 204 stores monitored EEG signals in memory 208. Memory 208 may include any volatile or non-volatile media, such as a RAM, ROM, NVRAM, EEPROM, flash memory, and the like. Memory 208 may also store program instructions that, when executed by processor 204, cause EEG sensing module 202 to monitor the EEG signal of brain 16. Accordingly, computer-readable media storing instructions may be provided to cause processor 204 to provide functionality as described herein.

EEG sensing module 202 includes circuitry that measures the electrical activity of a particular region, e.g., motor cortex, within brain 16 via electrodes 212A-E. EEG sensing module 202 may acquire the EEG signal substantially continuously or at regular intervals, such as at a frequency of about 1 Hz to about 100 Hz. EEG sensing module 202 includes circuitry for determining a voltage difference between two electrodes 212A-E, which generally indicates the electrical activity within the particular region of brain 16. One of the electrodes 212A-E may act as a reference electrode. An example circuit that EEG sensing module 40 may include is shown and described below with reference to FIGS. 15-20. The EEG signals measured from via external electrodes 212A-E may generate a voltage in a range of about 5 microvolts ($\mu$V) to about 100 $\mu$V.

The output of EEG sensing module 202 may be received by processor 204. Processor 204 may apply additional processing to the EEG signals, e.g., convert the output to digital values for processing and/or amplify the EEG signal. In some cases, a gain of about 90 decibels (dB) is desirable to amplify the EEG signals. In some embodiments, EEG sensing module 202 or processor 204 may filter the signal from electrodes 212A-E in order to remove undesirable artifacts from the signal, such as noise from electrocardiogram signals, electromyogram signals, and electro-oculogram signals generated within the body of patient 12.

Processor 204 may determine whether the EEG signal from EEG sensing module 202 includes the biosignal indicative of a volitional patient input via any suitable technique, such as the techniques described above with respect to processor 60 (FIG. 4) of IMD 18. If processor 204 detects the biosignal from the EEG signal, processor 204 may generate a therapy adjustment indication. The therapy adjustment indication may be a value, flag, or signal that is stored or transmitted to indicate patient 12 provided a volitional thought indicative of a desired adjustment to therapy. Processor 204 may transmit the therapy adjustment indication to a medical device via telemetry module 206, and the medical device may adjust therapy according to the therapy adjustment action associated with the biosignal or therapy adjustment indication. In this way, the biosignal from an EEG signal may be a control signal for adjusting therapy. In some embodiments, processor 204 may record the therapy adjustment indication in memory 208 for later retrieval and analysis by a clinician. For example, movement indications may be recorded over time, e.g., in a loop recorder, and may be accompanied by the relevant EEG signal.

In other embodiments, rather than generating a therapy adjustment indication, processor 204 may merely control the transmission of the EEG signal from EEG sensing module 202 to a medical device. The medical device may then determine whether the EEG signal includes the biosignal.

Figure 8:
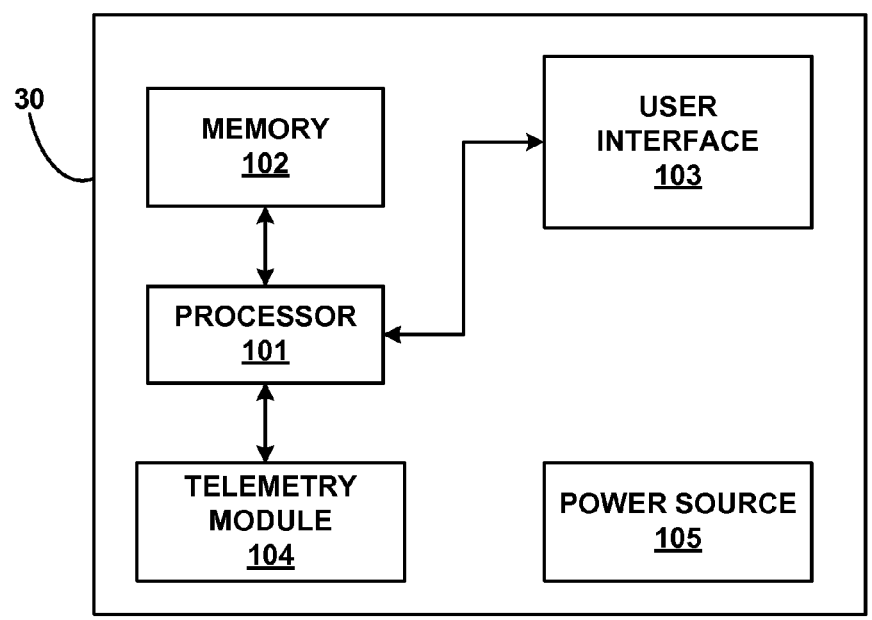
FIG. 8 is functional block diagram illustrating components of an embodiment of an external programmer.

FIG. 8 is functional block diagram illustrating components of an exemplary external programmer 30. External programmer 30 includes processor 101, memory 102, user interface 103, telemetry module 104, and power source 105. Processor 101 controls user interface 103 and telemetry module 104, and stores and retrieves information and instructions to and from memory 102. Programmer 30 may be configured for use as a clinician programmer or a patient programmer.

Programmer 30 may be used to select therapy programs (e.g., sets of stimulation parameters), generate new therapy programs, modify therapy programs through individual or global adjustments, transmit the new programs to a medical device, such as IMD 18 or IMD 36, and correlate biosignals with specific patient 12 activities and/or therapy adjustments. In a learning mode, programmer 30 may allow patient 12 and/or the clinician to create a volitional patient input and instruct IMD 18 to identify the resulting biosignal in brain 16.

Programmer 30 may also be used to correlate biosignals with desired therapy adjustments. Once the correlation between biosignals and volitional patient thoughts, as well as particular biosignals and particular therapy adjustments is completed, the correlated biosignals may be uploaded to a biosignal detection module for incorporation into a closed loop therapy control system. The resulting detection of the biosignal causes a therapy adjustment. Example therapy adjustments that may be correlated to biosignals include turning therapy on and off, increasing therapy amplitude, decreasing therapy amplitude, and changing therapy programs. While programmer 30 may be most useful when initially programming IMD 18, programmer 30 may be continually used throughout therapy to correct any problems with therapy.

The user, either a clinician or patient 12, may interact with programmer 30 through user interface 103. User interface 103 includes a display (not shown), such as an LCD or other screen, to show information related to stimulation therapy and input controls (not shown) to provide input to programmer 30. Input controls may include the buttons described in FIG. 12. Processor 101 monitors activity from the input controls and controls the display or stimulation function accordingly. In some embodiments, the display may be a touch screen that enables the user to select options directly from the display. In other embodiments, user interface 103 also includes audio circuitry for providing audible instructions or sounds to patient 12 and/or receiving voice commands from patient 12.

Memory 102 may include instructions for operating user interface 103, telemetry module 104 and managing power source 105. Memory 102 also includes instructions for managing biosignals and correlated therapy adjustments executable by processor 101. In addition, memory 102 may include instructions for guiding patient 12 through the learning mode when correlating biosignals to therapy adjustments and/or activities. Memory 102 may also store any therapy data retrieved from therapy device 18 during the course of therapy. The clinician may use this therapy data to determine the progression of patient 12 disease in order to predict future treatment.

Memory 102 may include any volatile or nonvolatile memory, such as RAM, ROM, EEPROM or flash memory. Memory 102 may also include a removable memory portion that may be used to provide memory updates or increases in memory capacities. A removable memory may also allow sensitive patient data to be removed before programmer 30 is used by a different patient. Processor 101 may comprise any combination of one or more processors including one or more microprocessors, DSPs, ASICs, FPGAs, or other equivalent integrated or discrete logic circuitry. Accordingly, processor 101 may include any suitable structure, whether in hardware, software, firmware, or any combination thereof, to perform the functions ascribed herein to processor 101.

Wireless telemetry in programmer 30 may be accomplished by RF communication or proximal inductive interaction of external programmer 30 with therapy device 18. This wireless communication is possible through the use of telemetry module 104. Accordingly, telemetry module 104 may be similar to the telemetry module contained within therapy device 18. In alternative embodiments, programmer 30 may be capable of infrared communication or direct communication through a wired connection. In this manner, other external devices may be capable of communicating with programmer 30 without needing to establish a secure wireless connection.

Power source 105 delivers operating power to the components of programmer 30. Power source 105 may include a battery and a power generation circuit to produce the operating power. In some embodiments, the battery may be rechargeable to allow extended operation. Recharging may be accomplished electrically coupling power source 105 to a cradle or plug that is connected to an alternating current (AC) outlet. In addition, recharging may be accomplished through proximal inductive interaction between an external charger and an inductive charging coil within programmer 30. In other embodiments, traditional batteries (e.g., nickel cadmium or lithium ion batteries) may be used. In addition, programmer 30 may be directly coupled to an alternating current outlet to operate. Power source 105 may include circuitry to monitor power remaining within a battery. In this manner, user interface 103 may provide a current battery level indicator or low battery level indicator when the battery needs to be replaced or recharged. In some cases, power source 105 may be capable of estimating the remaining time of operation using the current battery.

Figure 9A:
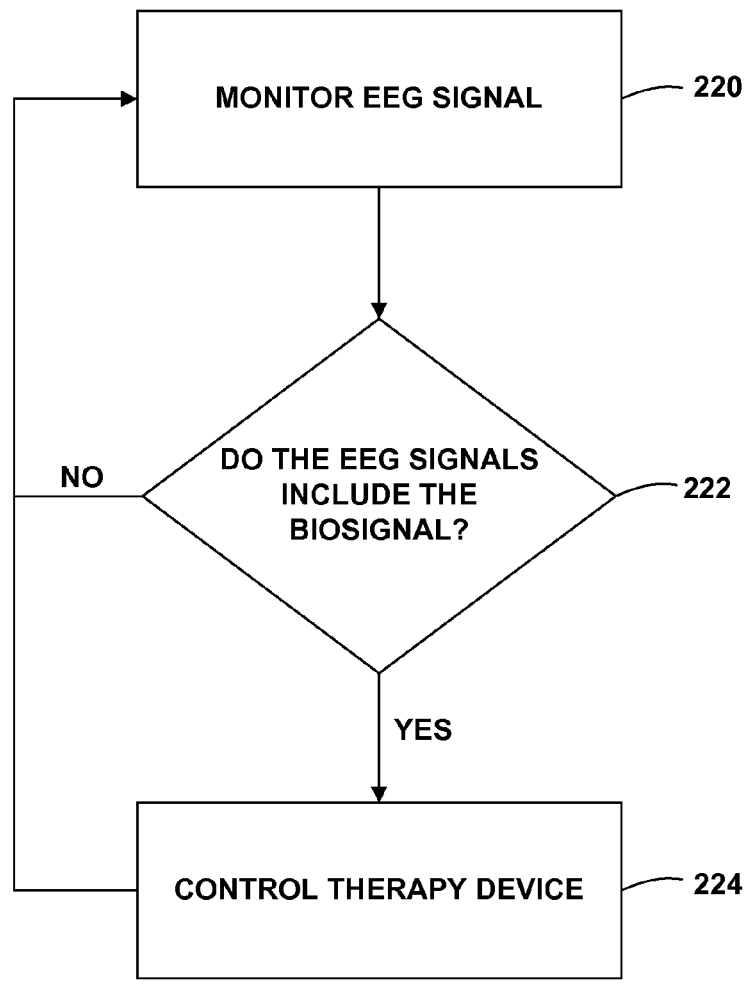
FIGS. 9A and 9B are flow diagrams illustrating embodiments of techniques for adjusting therapy according to detected biosignals from the patient.

FIG. 9A illustrates a flow diagram of a technique for controlling a therapy device, such as IMD 18 (FIG. 1), IMD 36 (FIG. 2A) or external cue device 54 (FIG. 3) based on a biosignal within brain 16 that results from a volitional patient input. While FIGS. 9A and 10A-B and 14 are primarily described with reference to biosignal detection module 200 (FIG. 7) and IMD 36 (FIG. 2), in other embodiments, the technique shown in FIG. 9A may be employed by any therapy system that includes a biosignal detection module and a therapy delivery device, such as IMD 18, which includes both a biosignal detection module 66 and a stimulation generator 64.

EEG sensing module 202 (FIG. 7) of biosignal detection module 200 monitors the EEG signal within the motor cortex of brain 16 via electrodes 212A-E continuously or at regular intervals (220). In other embodiments, EEG sensing module 202 may monitor the EEG signal within another part of brain 16, such as the sensory motor strip or occipital cortex. Processor 204 (FIG. 7) of biosignal detection module 200 receives the EEG signals from EEG sensing module 202 and processes the EEG signals to determine whether the EEG signals indicate patient 12 has generated the volitional patient input indicative of a desired therapy adjustment action, i.e., whether the biosignal is detected (222). A signal processor within processor 202 may determine whether the EEG signals include the biosignal using any suitable technique, such as the techniques described above (e.g., voltage, amplitude, temporal correlation or frequency correlation with a template signal, or combinations thereof).

If the biosignal is not present in the monitored EEG signals, EEG sensing module 202 may continue monitoring the EEG signal under the control of processor 204 (220). If the biosignal is detected, processor 204 may implement control of a therapy device (224). For example, in the case of external cue device 54 (FIG. 3), processor 204 may generate a therapy adjustment indication and transmit the indication to processor 90 (FIG. 6) of external cue device 54 via telemetry module 206, and processor 90 may cause cue generator 94 to deliver a visual cue to patient 12. As another example, in the case of IMD 36 of FIG. 2A, upon detecting the presence of the biosignal in the EEG signals, processor 204 of biosignal detection module 200 may provide a signal to a processor of IMD 36 via the respective telemetry modules. The processor of IMD 36 may then initiate therapy delivery via the stimulation generator or adjust therapy (e.g., increase the amplitude of stimulation in order to help patient 12 initiate muscle movement). After controlling a therapy device, the processor 204 may continue monitoring the EEG signal for a biosignal.

Figure 9B:
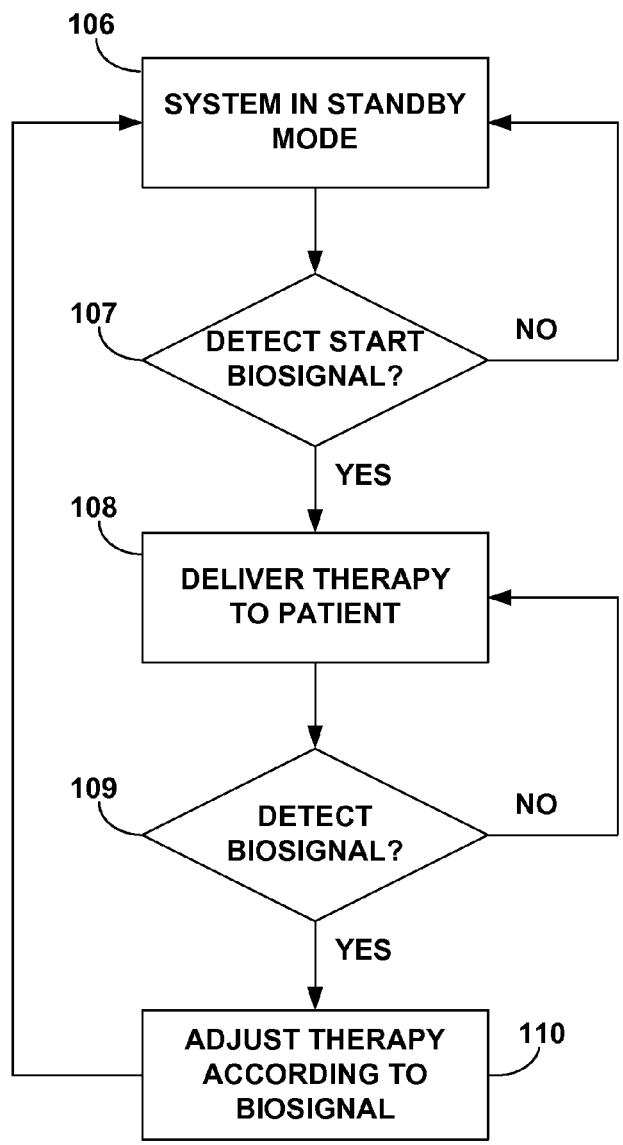

FIG. 9B is a flow diagram illustrating another embodiment of a technique for initiating therapy delivery based on a biosignal indicative of a volitional patient input relating to a desired therapy adjustment action. While FIG. 9B is described primarily with reference to IMD 18, which includes biosignal detection module 66, in other embodiments, other devices or combination of devices, such as IMD 36 and biosignal detection module 42, may implement the technique shown in FIG. 9B. As shown in FIG. 9B, IMD 18 may be in standby mode as patient 12, during which patient 12 is not currently receiving therapy or is receiving a minimal amount of therapy (106). Biosignal detection module 66 monitors an EEG signal to determine whether the EEG signal includes a biosignal that indicates patient 12 provided a volitional input, such as a thought relating to a particular muscle movement, to initiate therapy (107). If biosignal detection module 66 does not detect the biosignal, IMD 18 remains in standby mode. If biosignal detection module 66 detects the biosignal within the monitored EEG, processor 60 may control stimulation generator 64 (FIG. 4) to deliver therapy to patient 12 (108).

Stimulation generator 64 may continue delivering therapy to patient 12 for a predetermined amount of time or until processor 60 detects a signal that indicates therapy should be adjusted (e.g., stopped). The signal may take the form of a patient input (e.g., via programmer 30, an implanted accelerometer or via a biosignal generated in response to a volitional patient though). Using the latter signal as an example, if biosignal detection module 66 does not detect a biosignal that indicates patient 12 provided an input to stop therapy (109), therapy continues (108). However, if detection module 66 detects another "adjust therapy" biosignal (109), processor 60 controls stimulation generator 64 to take the associated therapy adjustment (110). For example, if the biosignal is indicative of a patient input to stop therapy delivery, processor 60 controls stimulation generator 64 to stop delivery of electrical stimulation to patient 12. For example, if IMD 18 determines that the biosignal directs the therapy module to stop therapy (110), IMD 18 stops therapy, and may return to a standby mode.

Figure 10A:
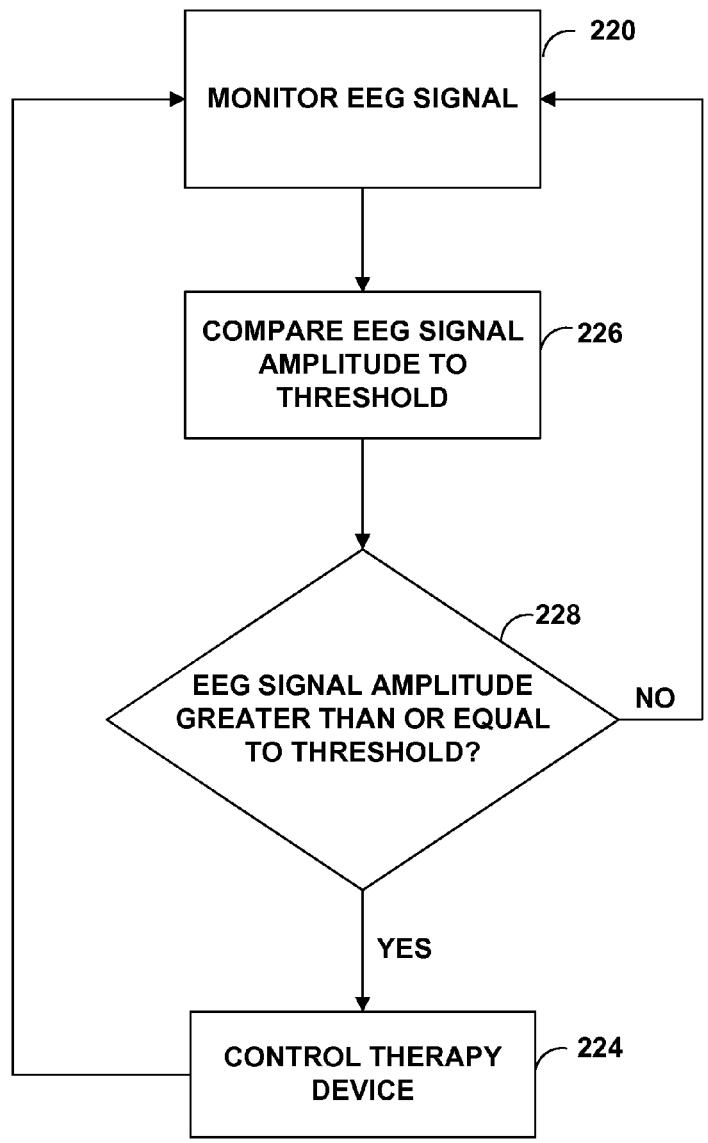
FIGS. 10A and 10B are a flow diagram illustrating embodiments of techniques that may be employed to control a therapy device based on an EEG signal.

FIG. 10A is a flow diagram of an embodiment of a technique for determining whether an EEG signal includes a biosignal indicative of a volitional patient thought relating to a desired therapy adjustment action. EEG sensing module 202 (FIG. 7) of biosignal detection module 200 monitors the EEG signal within the motor cortex of brain 16 via electrodes 212A-E continuously or at regular intervals (220), such as at a measurement frequency of about one hertz (Hz) to about 100 Hz. In other embodiments, EEG sensing module 202 may monitor the EEG signal within another part of brain 16, such as the sensory motor strip or occipital cortex. Processor 204 of biosignal detection module 200 compares the amplitude of the EEG signal waveform to a stored threshold value (226). The relevant amplitude may be, for example, the instantaneous amplitude of an incoming EEG signal or an average amplitude of the EEG signal over period of time. In one embodiment, the threshold value is determined during the trial phase that precedes implantation of a chronic therapy delivery device within patient 12.

In one embodiment, if the monitored EEG signal waveform comprises an amplitude that is less than the threshold value (228), processor 204 does not generate any control signal to adjust therapy delivery. On the other hand, if the monitored EEG signal waveform comprises an amplitude that is greater than or equal to the threshold value (228), the EEG signal includes the biosignal indicative of the volitional patient input, and processor 204 may implement control of a therapy device (224). In other embodiments, depending on the type of volitional patient input as well as the region of brain 16 in which the EEG signals are monitored, processor 204 may implement control of a therapy device if the amplitude of the EEG signal falls below a threshold value. A trial phase may be useful for determining the appropriate relationship between the threshold of the EEG signal and the threshold value.

Figure 10B:
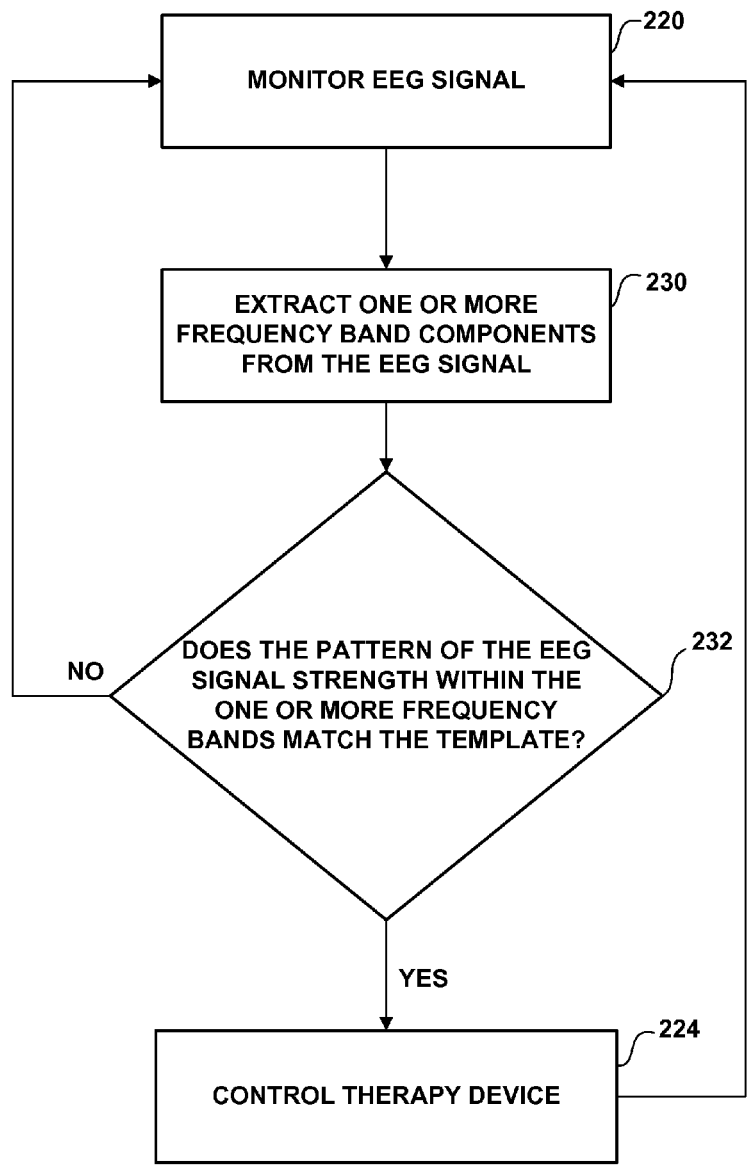

FIG. 10B is a flow diagram of another embodiment of a technique for determining whether an EEG signal includes a biosignal indicative of a volitional patient input associated with a desired therapy adjustment action. EEG sensing module 202 (FIG. 7) of biosignal detection module 200 monitors the EEG signal within the motor cortex of brain 16 via electrodes 212A-E continuously or at regular intervals (220), such as at a measurement frequency of about one hertz (Hz) to about 100 Hz. In other embodiments, EEG sensing module 202 may monitor the EEG signal within another part of brain 16, such as the sensory motor strip or occipital cortex.

A signal processor within processor 204 of biosignal detection module 200 extracts one or more frequency band components of the monitored EEG signal (230) in order to determine whether the biosignal is detected. In the embodiment shown in FIG. 10B, processor 204 compares the pattern in the EEG signal strength (i.e., the power level) within one frequency bands with a template (232). In this way, processor 204 may use signal analysis techniques, such as correlation, to implement a closed-looped system for adjusting therapy.

Figure 14:
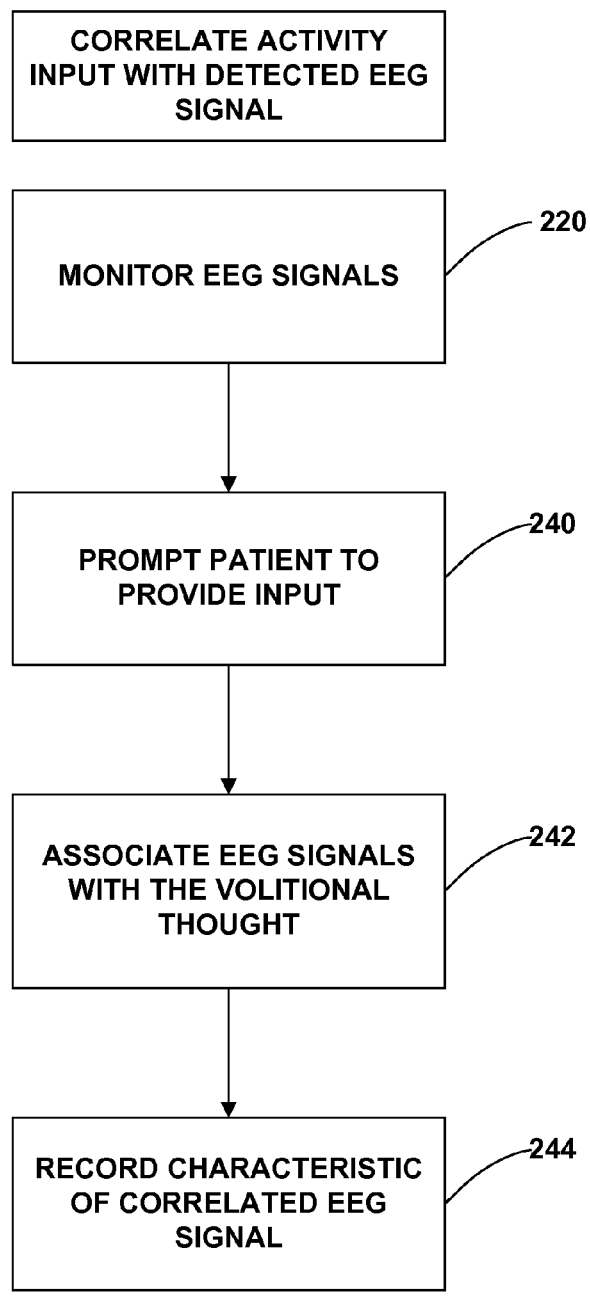
FIG. 14 is a flow diagram illustrating an embodiment of a technique for associating a volitional patient input with an EEG signal characteristic.

If the pattern of the EEG signal correlates well, i.e., matches, with a pattern template (232), processor 204 of biosignal detection module 200 controls a medical device (e.g., initiates therapy, deactivates therapy or increases or decreases a therapy parameter) (224). In some embodiments, the template matching algorithm that is employed to determine whether the pattern in the EEG signal matches the template may not require a one hundred percent (100%) correlation match, but rather may only match some percentage of the pattern. For example, if the monitored EEG signal exhibit a pattern that matches about 75% or more of the template, the algorithm may determine that there is a substantial match between the pattern and the template, and the biosignal is detected. In other embodiments, processor 204 may compare a pattern in the amplitude waveform of the EEG signal (i.e., in the time domain) with a template. The pattern template for either the template matching techniques employed in either the frequency domain or the time domain may be generated in a trial phase, an example of which is shown in FIG. 14 and described below.

Figure 11:
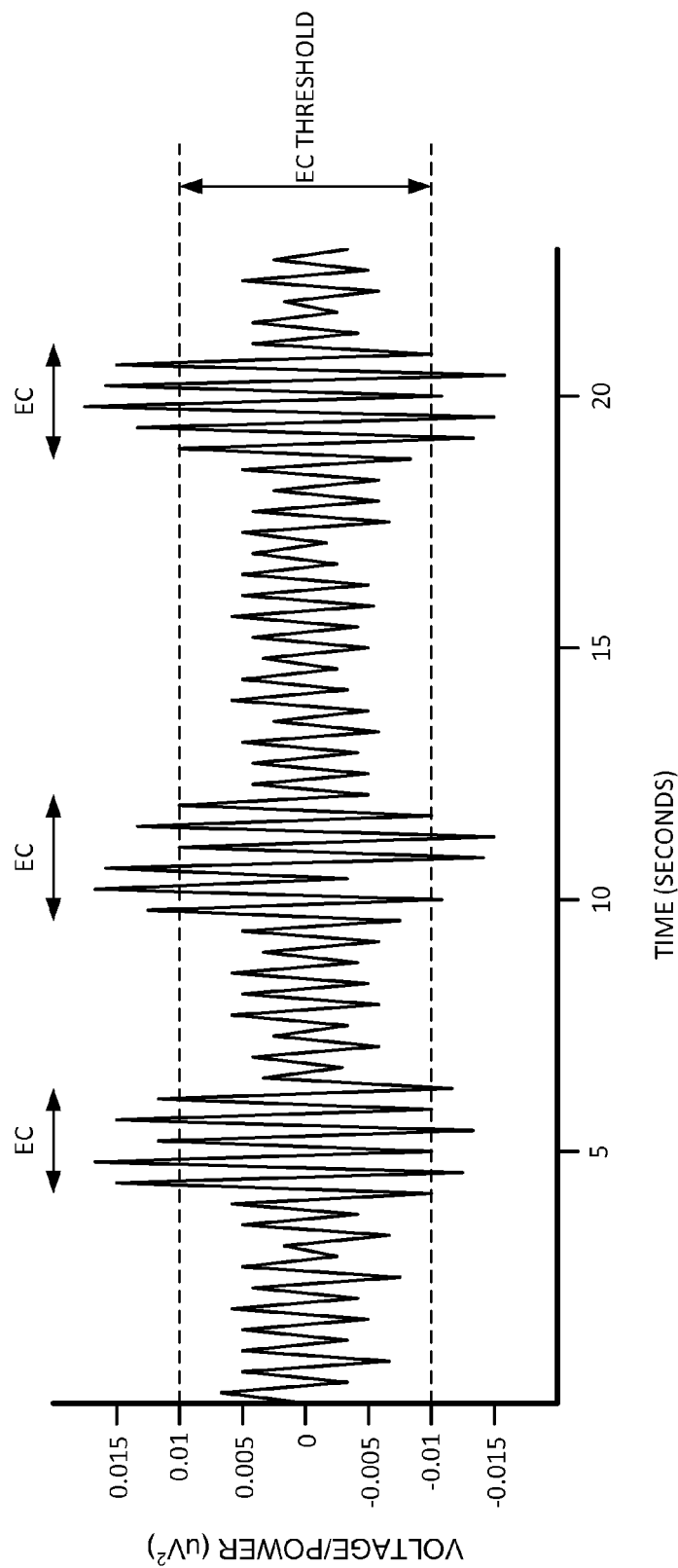
FIG. 11 is an example electrical signal received by the biosignal detection module that indicates when a patient closes and opens his eyes.

FIG. 11 is an example EEG signal within an occipital cortex of brain 16 of patient 12, where the EEG signal is received by biosignal detection module 200 and is indicative of when patient 12 closes and opens the eyelids. Biosignal detection module 200 may be incorporated into any of IMDs 16, 36, biosignal detection module 42, external cue device 54 or other devices that are capable of detecting the EEG signal shown in FIG. 11 when electrodes are positioned over the occipital cortex of brain 16. As shown in FIG. 11, the EEG signal has been tuned to the alpha frequency band, and in particular, approximately 10 Hz. In FIG. 11, the 10 Hz frequency band component of the EEG signal is plotted as voltage/power (uV$^2$) versus time (seconds). The resulting amplitude changes in the EEG signal are identifiable between moments when the eyes of patient 12 are closed and open. Thus, FIG. 11 illustrates an example of a pattern in the EEG signal strength within the alpha frequency band, where the pattern shown indicates the monitored EEG signal included the biosignal.

When the eyes of patient 12 are open, the biosignal oscillates between $(0.005\ uV)^2$ and $-(0.005\ uV)^2$. However, the signal changes in amplitude when the eyes of patient 12 are closed, as indicated by "EC" in FIG. 11. Volitional thought created by patient 12 that resulted in closing the eyes generated a biosignal with amplitudes approaching $(0.015\ uV)^2$ and $-(0.015\ uV)^2$. The increase in the amplitude of the alpha band component of the EEG signal for a certain duration of time, such as two seconds, may be selected as a biosignal for used in a closed loop therapy system. For example, biosignal detection module 42 may monitor the alpha band component of the EEG signal, tuned to about 10 Hz, and upon detecting a power level that exceeds a threshold window of $-(0.01\ uV)^2$ to $(0.01\ uV)^2$ for a duration of two or more seconds, biosignal detection module 42 may generate a control signal for adjusting therapy delivery to patient 12. Thus, the biosignal is indicative of a volitional patient input in the form of the patient closing his eyes for a certain period of time. Alternatively, therapy module may identify absolute amplitude values greater than $(0.02\ uV)^2$.

In order to minimize the possibility that patient 12 may inadvertently activate the therapy adjustment by closing his eyes, biosignal detection module 42 may be configured to identify a particular pattern in the signal strength (measured in voltage/power) in the 10 Hz frequency band. Therefore, patient 12 may set up a pattern in closing eyes that must be detected before therapy changes are performed. For example, patient 12 may program IMD 18 to detect five separate eyes closed events within a 10 second period before therapy is to be delivered. As another example, the pattern in the signal strength shown in FIG. 11 is generated when patient 12 closes his eyes for about two seconds, opens his eyes for about four seconds, closes his eyes for about two seconds, opens his eyes for about ten seconds, and closes his eyes again for about two seconds. Biosignal detection module 42 may use this biosignal to recognize a volitional patient input from patient 12. Other patterns are also contemplated.

Another technique for minimizing the possibility that patient 12 may inadvertently provide a volitional thought that activates the therapy adjustment may be combining the biosignal detection with another input mechanism. In one embodiment, for example, patient 12 may tap an external or implanted accelerometer, which is coupled to biosignal detection module 42 via a wired connection or a wireless connection. Biosignal detection module 42 may recognize the tapping (e.g., tapping in a particular pattern) as a confirmation that patient 12 purposefully generated the biosignal to adjust therapy.

The 10 Hz component of an EEG signal shown in FIG. 11 is an example of one biosignal that biosignal detection module 200 may identify in order to initiate an adjustment to therapy delivery. Biosignal detection module 200 may monitor multiple different biosignals of different frequency bands and/or at different locations within brain 16. Patient 12 may utilize any of these biosignals in creating a pattern of volitional inputs necessary for IMD 18 (or another device) to adjust therapy. Biosignal detection module 200 may be configured to detect more than one type of biosignal indicative of a volitional patient thought. For example, one biosignal may increase an amplitude of stimulation, while another biosignal may turn therapy off or into a safe mode.

Figure 12:
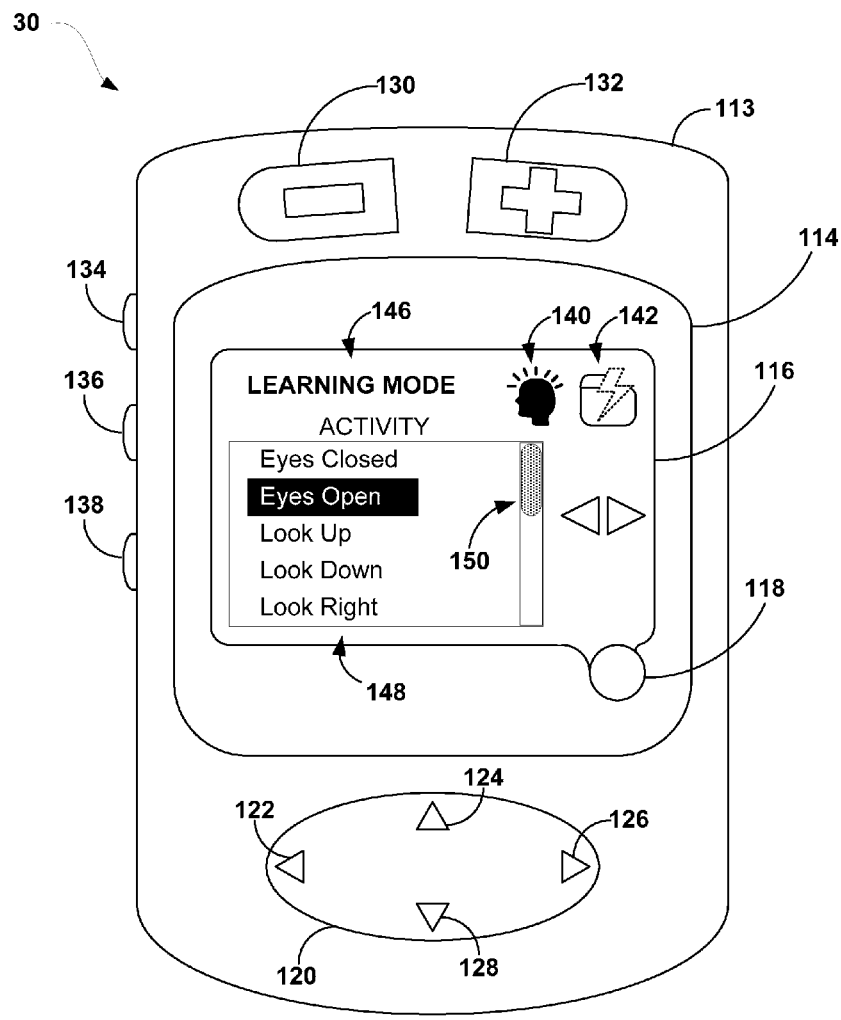
FIG. 12 is an embodiment of a programmer with a user interface that allows the programmer to learn and match biosignals to patient activities.

FIG. 12 illustrates an embodiment of programmer 30, which includes user interface 116 for receiving input from a user, such as patient 12 or a clinician, and displaying information to the user. Programmer 30 is a handheld computing device that is useful for learning and matching EEG signals to volitional patient thoughts in order to define biosignals for implementation into a closed loop therapy system. Programmer 30 includes outer housing 113, which encloses circuitry necessary for programmer 30 to operate. Housing 113 may be constructed of a polymer, metal alloy, composite, or combination material suitable to protect and contain components of programmer 30. In addition, housing 113 may be partially or completely sealed such that fluids, gases, or other elements may not penetrate the housing and affect components therein.

Programmer 30 also includes display 114, select button 118, control pad 120 with directional buttons 122, 124, 126 and 128, increase button 132, decrease button 130, contrast buttons 134 and 136, and power button 138. Power button 138 turns programmer 30 on or off. Programmer 30 may include safety features to prevent programmer 30 from shutting down during a telemetry session with IMD 18 or another device in order to prevent the loss of transmitted data or the stalling of normal operation. Alternatively, programmer 30 and IMD 18 may include instructions which handle possible unplanned telemetry interruption, such as battery failure or inadvertent device shutdown. While IMD 18 is primarily referred to throughout the discussion of FIG. 12, in other embodiments, programmer 30 may be configured to communicate with other medical devices, such as IMD 36 (FIG. 2) or external cue device 54 (FIG. 3). Furthermore, while patient 12 is primarily referred to throughout the discussion of FIG. 12, in other embodiments, other users may use programmer 30.

Display 114 may be an LCD or another type of monochrome or color display capable of presenting information to patient 12. Contrast buttons 134 and 136 may be used to control the contrast of display 114. Display 114 may provide information regarding the current mode, selections for patient 12, and operational status of programmer 30. Control pad 120 allows patient 12 to navigate through items presented on display 114. Patient 12 may press control pad 120 on any of arrows 122, 124, 126 and 128 in order to move between items presented on display 114 or move to another screen not currently shown by display 114. For example, patient 12 may depress or otherwise activate arrows 122 and 126 to navigate between screens of user interface 116. Patient 12 may press select button 118 to select any highlighted element in user interface 116. In some embodiments, the middle portion of control pad 120 may provide a "select" button that enables patient 12 to select a particular item presented on display 114, such as an item that is highlighted on display 114. In other embodiments, scroll bars, a touch pad, scroll wheel, individual buttons, or a joystick may perform the complete or partial function of control pad 120.

Decrease button 130 and increase button 132 provide input mechanisms for patient 12. In general, depressing decrease button 130 one or more times may decrease the value of a highlighted therapy parameter and depressing increase button 132 one or more times may increase the value of a highlighted therapy parameter. While buttons 130 and 132 may be used to control the value of any therapy parameter, patient 12 may also utilize buttons 130 and 132 to select particular programs during a therapy session. Buttons 130 and 132 may alternatively decrease or increase the thresholds required for identifying biosignals. For example, patient 12 may enter learning mode 146 of programmer 30 and decrease the sensitivity of the biosignal detection if therapy adjustments are occurring at a greater frequency than desired. In other embodiments, control pad 120 may be the only input that patient 12 may use to navigate through the screens and menus of programmer 30.

Programmer 30 may take other shapes or sizes not described herein. For example, programmer 30 may take the form of a clam-shell shape, similar to cellular phone designs. When programmer 30 is closed, some or all elements of the user interface may be protected within the programmer. When programmer 30 is open, one side of the programmer may contain a display while the other side may contain input mechanisms. In any shape, programmer 30 may be capable of performing the requirements described herein.

In alternative embodiments, the buttons of programmer 30 may perform different functions than the functions provided in FIG. 12 as an example. In addition, other embodiments of programmer 30 may include different button layouts or number of buttons. For example, display 114 may be a touch screen that incorporates all user interface functionality.

In FIG. 12, learning mode 146 is presented on user interface 116. In the learning mode 146, programmer 30 correlates an EEG signal with the volitional input. For example, patient 12 may move his index finger in a particular pattern, and programmer 30 may correlate the monitored EEG signal at the time the patient 12 moved his index finger with the movement. A clinician, with the aid of a computing device, may extract a biosignal (e.g., a particular frequency component of the EEG signal) from the correlated EEG signal. The frequency band in which the EEG signal exhibits a noticeable change or characteristic may be selected at this stage. Biosignal icon 140 indicates whether biosignal detection module 42 is currently active and monitoring EEG signals, either as a part of learning mode 146 or during implementation of a chronic therapy system. In the embodiment shown in FIG. 12, biosignal icon 140 indicates that biosignal detection module 200 (or another biosignal detection module) is currently active and monitoring EEG signals because icon 140 is darkened with lines extending from the head in icon 140. In contrast, when biosignal icon 140 is merely an outline and not filled in, biosignal icon 140 indicates that biosignal detection module 200 is not monitoring EEG signals.

Stimulation icon 142 indicates whether therapy is being delivered to patient 12. In the embodiment shown in FIG. 12, the lightning bolt of stimulation icon 142 is not highlighted, thereby indicating that that therapy is not currently being delivered. In embodiments in which a therapy system delivers a therapy other than electrical stimulation, stimulation icon 142 may have a different configuration.

Activity field 148 of the learning mode 146 user interface 116 is populated with possible activities for generating the volitional patient input. Scroll bar 150 indicates that more activates are available lower in the field. The activities may include physical activities (e.g., muscle movement) as well as mental activities (e.g., a focused task, such as performing a mathematical calculation, spelling a word, reciting any combination of letters, words, numbers, symbols, sounds, and so forth). Patient 12 may use control pad 120 to select an activity from activity field 148. As shown, "Eyes Open" is highlighted. Patient 12 may voluntarily keep his eyes open while pressing select button 118. In response, programmer 30 may provide a signal to biosignal detection module 200 via telemetry module 104, and biosignal detection module 42 may monitor the EEG signal that corresponds to the patient's volitional thought relating to keeping his eyes open. Biosignal detection module 200 may record the corresponding EEG signal or may transmit the EEG signal to programmer 30, which may store the EEG signal in memory 102 (FIG. 8).

As previously described, programmer 30 or a clinician, with the aid of programmer 30 or another computing device, may extract a biosignal (e.g., a particular frequency component of the EEG signal, the amplitude of the EEG signal, a pattern in the amplitude waveform of the EEG signal, and so forth) from the EEG signal that corresponds to the selected activity from activity field 148. Programmer 30 may store the biosignal within memory 102 and upload the biosignal to biosignal detection module 200, IMD 18 or another medical device for future use. Patient 12 may subsequently select "Eyes Closed" from activity field 148 when closing his eyes to allow biosignal detection module 42 to extract the contrasting biosignal from the EEG signal associated with the "eyes closed" state. If desired, patient 12 may complete each of the activities in the activity field 148 in this manner until all the desired activities have been correlated with detected biosignals.

Programmer 30 may deliver a warning message to patient 12 if the correlation between an EEG signal and activity was unsuccessful. Programmer 30 may then prompt patient 12 to provide the input relating to the selected activity or select another activity to correlate with a biosignal. Additionally, programmer 30 may request that patient 12 repeat the correlation at least one time before the correlation between the activity and biosignal is stored. In some embodiments, programmer 30 may guide patient 12 through the learning mode 146. Programmer 30 may prompt patient 12 for each activity and automate the process to the most common activities used in controlling therapy adjustments with volitional cues.

Patient 12 may also navigate to another screen to review the biosignals that have been identified. Programmer 30 may also allow patient 12 to return to learning mode 146 to repeat certain activities or regenerate certain biosignals if desired. In some cases, patient 12 may be able to enter new activities not populated in activity field 148. For example, patient 12 may desire to use a volitional cue not normally desired by other patients. The clinician may enable or disable any of these custom applications of programmer 30, depending upon the ability of patient 12 to utilize the features without hindering effective therapy.

After determining one or more biosignals indicative of a volitional patient thought, programmer 30 or the clinician with the aid of programmer 30 or another computing device, may associate the one or more biosignals to one or more therapy adjustments. For example, using the "eyes open" and "eyes closed" biosignals, the clinician may associate a particular pattern of the patient's "eyes open" biosignal and "eyes closed" biosignal with turning therapy on (e.g., initiating the delivery of electrical stimulation). As other examples, the clinician may associate a particular pattern of the patient's "eyes open" biosignal and "eyes closed" biosignal with an increase or decrease in amplitude of stimulation or a switch to another stimulation program.

Figure 13:
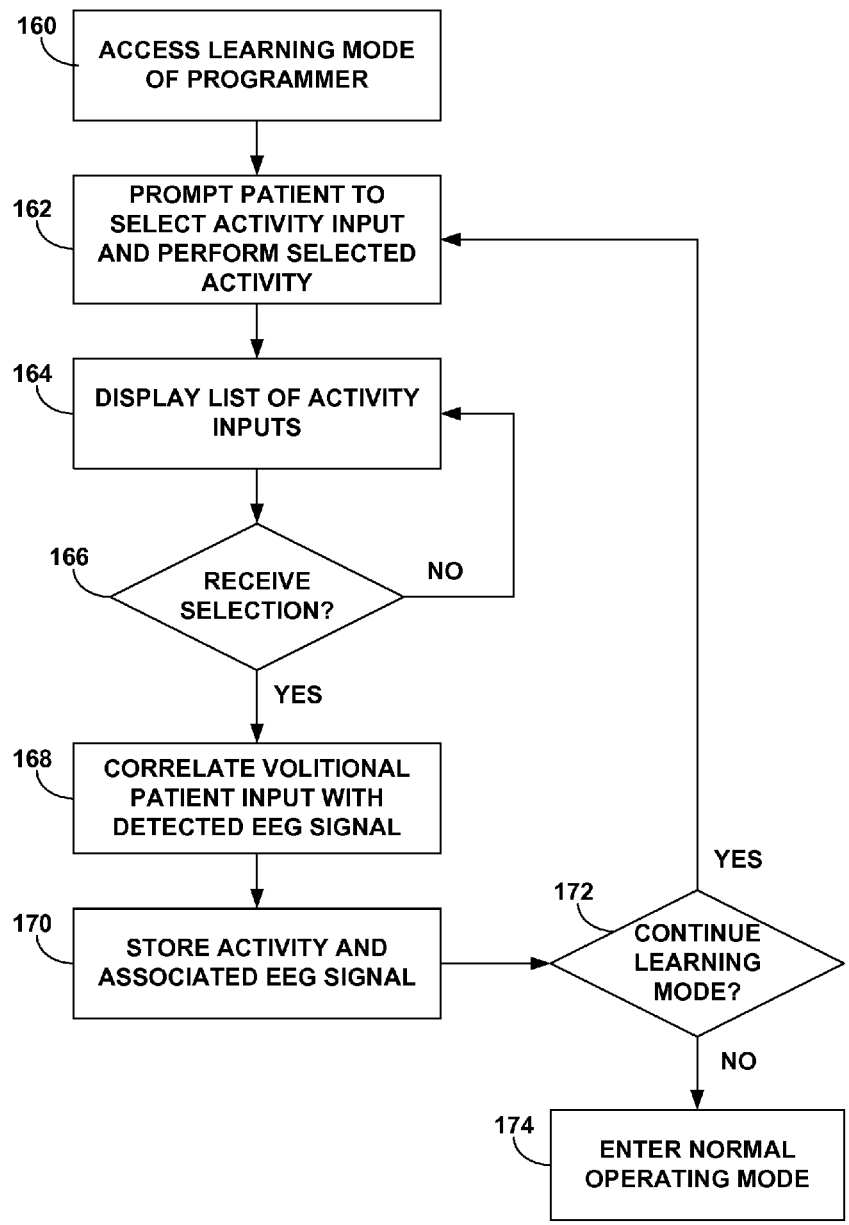
FIG. 13 is a flow diagram illustrating an embodiment of a technique that may be employed by the programmer of FIG. 12 to correlate biosignals with volitional patient activities.

FIG. 13 is a flow diagram illustrating an embodiment of a technique that may be employed by programmer 30 to correlate one or more biosignals with a volitional patient thought related to a patient activity. While the technique shown in FIG. 13 is primarily described with respect to therapy system 10, the technique may be employed with the other therapy systems described herein. Upon implantation of therapy system 10, biosignal detection module 66 of IMD 18 is programmed to detect relevant biosignal and provide a signal to processor 60, which controls the adjustment of therapy indicated by the biosignal. The relevant biosignals are determined via learning mode 146 of programmer 30. Patient 12 or the clinician may utilize the learning mode 146 of programmer 30 at times other than the initial programming of biosignal detection module 66, e.g., during the patient's follow-up visit to the clinician's office.

As shown in FIG. 13, the clinician accesses learning mode 146 of programmer 30 (or another computing device) (160). Programmer 30 prompts patient 12 or the clinician to select an activity input from activity field 148 and perform the selected activity (162). By performing the selected activity, patient 12 generates the volitional thoughts and provides the volitional input that result in the detectable biosignal within brain 16. Biosignal detection module 66 of IMD 18 monitors the EEG signal within brain 16 that results from the volitional patient thought during the undertaking of the action. The clinician may then extract the relevant biosignal from the EEG signal associated with the volitional patient thought with the aid of processor 60 of IMD 18, processor 101 of programmer 30 or a processor of another device.

Programmer 30 may display activity field 148, which includes a plurality of activities that patient 12 may undertake to generate the volitional thought (164) and awaits the selection of another activity from activity field 148 by patient 12 or the clinician (166). If programmer 30 does not receive the selection of activity inputs (166), programmer 30 continues to display the list of activity inputs (164).

Once programmer 30 receives the activity input selection from patient 12 (166), processor 60 of programmer 30 correlates the activity input with the detected EEG signal (168). Processor 60 then stores the activity and associated EEG signal in memory 62 (170). If the clinician desires to continue the learning mode (172), programmer again prompts patient 12 to select another activity input (162). If the clinician does not desire to continue the learning mode (172), programmer 30 exits the learning mode and enters the normal operating mode of IMD 18 (174). In the normal operating mode, IMD 18 may remain in a standby mode or deliver therapy according to a program until patient 12 creates the volitional cue that generates a detectable biosignal for adjusting therapy.

FIG. 14 is a flow diagram of a technique for determining the biosignal that indicates patient 12 generated a volitional thought indicative of a desired therapy adjustment. In the embodiment shown in FIG. 14, the biosignal includes an EEG signal characteristic (in the time domain or frequency domain). However, in other embodiments, the biosignal may include other neural-based signals, such as deep brain electrical signals. Factors that may affect the relevant EEG signal characteristic may include factors such as the age, size, and relative health of the patient. The relevant EEG signal characteristic may even vary for a single patient, depending on fluctuating factors such as the state of hydration, which may affect the fluid levels within the brain of the patient. Accordingly, it may be desirable in some cases to measure the EEG signal of a particular patient over a finite trial period of time that may be anywhere for less than one week to one or more months in order to tune the trending data or threshold values of an EEG signal that is associated with a particular volitional patient input to the particular patient.

It is also believed that it is possible for the relevant EEG signal characteristic for a particular volitional patient input to be the same for two or more patients. In such a case, one or more previously determined EEG signal characteristic may be a starting point for a clinician, who may adapt (or "calibrate" or "tune") the EEG signal characteristic value (e.g., a threshold amplitude or power value) to a particular patient. The previously generated EEG signal characteristic value may be, for example, an average of threshold values for a large number (e.g., hundreds, or even thousands) of patients.

Processor 204 of biosignal detection module 200 monitors the EEG signal acquired by EEG sensing module 202 from the relevant region of brain 16 of patient 12 (220). EEG sensing module 202 may acquire the EEG signal substantially continuously or at regular intervals, such as at a frequency of about 1 Hz to about 100 Hz. In addition, the EEG signal for more than one region of brain 16 may also be generated to determine which region of brain 16 provides the most relevant indication of the volitional patient input. The region of brain 16 that provides the most relevant indication of the movement state may influence where electrodes 212A-E are positioned.

During the same trial period of time, patient 12 is prompted to provide the input that is indicative of the desired therapy adjustment action (240). For example, in one embodiment, the volitional patient thought includes moving an index finger in a particular pattern, and the pattern of the index finger movement may be indicative of desired increase in stimulation amplitude.

An EEG signal is associated with the volitional patient input (242). In one embodiment, programmer 30 may provide an indication to biosignal detection device 200 that patient 12 is generating the volitional patient thought, and processor 204 of biosignal detection device 200 may associate the EEG signal with the patient input. In another embodiment, biosignal detection module 200 may provide the monitored EEG signal to programmer 30, and processor 90 of programmer 30 may associate the EEG signal with the patient input. The EEG signal may be matched to the volitional patient thought any suitable way, e.g., based on the time of occurrence. For example, prior to, during or after the time in which patient 12 provide the volitional thought, patient 12 may depress a button on programmer 30 to cause programmer 30 to record the date and time, or alternatively, cause biosignal detection module 200 to record the date and time the volitional thought was executed.

Processor 204 of biosignal detection device 200, processor 90 of programmer 30 or a processor of another computing device may record a characteristic of the correlated EEG signal i.e., the biosignal, within memory (244). The biosignal may include the amplitude or a pattern in the amplitude waveform of the EEG signal, the signal strength or a pattern in the signal strength of the EEG signal within one or more frequency bands, or other EEG signal characteristics. In one embodiment, a clinician or computing device may review the data relating to the volitional patient input, and associate the EEG signal within a certain time range prior to, e.g., 1 millisecond (ms) to about 3 seconds, and during the volitional patient input. The clinician or computing device may compare the EEG signals for two or more times in which patient 12 generates the volitional thought in order to confirm that the particular EEG signal characteristic, i.e., the biosignal, is indicative of a desired therapy adjustment action.

After correlating the EEG signal with a volitional patient thought indicative of a desired therapy adjustment action, the clinician may record the EEG signal characteristic (244) for later use by processor 204 of biosignal detection module 200, processor 90 of programmer 30 or a processor of a medical device. Alternatively, a computing device may automatically determine the relevant EEG signal characteristic.

FIG. 15 is a block diagram illustrating an exemplary frequency selective signal monitor 270 that includes a chopper-stabilized superheterodyne instrumentation amplifier 272 and a signal analysis unit 273. Signal monitor 270 may utilize a heterodyning, chopper-stabilized amplifier architecture to convert a selected frequency band of a physiological signal to a baseband for analysis. The physiological signal may be analyzed in one or more selected frequency bands to trigger delivery of patient therapy and/or recording of diagnostic information. In some cases, signal monitor 270 may be utilized within a medical device. For example, signal monitor 270 may be utilized within a biosignal detection module included in IMD 18 implanted within patient 12 from FIG. 1. In other cases, signal monitor 270 may be utilized within a separate sensor that communicates with a medical device. For example, signal monitor 270 may be utilized within biosignal detection module 39 implanted within patient 12 and coupled to IMD 36 from FIG. 2A or external cue device 54 from FIG. 3. As another example, signal monitor 270 may be utilized within biosignal detection module 42 positioned external to patient 12 and coupled to IMD 36 from FIG. 2B or external cue device 54 from FIG. 3.

In general, frequency selective signal monitor 270 provides a physiological signal monitoring device comprising a physiological sensing element that receives a physiological signal, an instrumentation amplifier 272 comprising a modulator 282 that modulates the signal at a first frequency, an amplifier that amplifies the modulated signal, and a demodulator 288 that demodulates the amplified signal at a second frequency different from the first frequency. A signal analysis unit 273 that analyzes a characteristic of the signal in the selected frequency band. The second frequency is selected such that the demodulator substantially centers a selected frequency band of the signal at a baseband.

The signal analysis unit 273 may comprise a lowpass filter 274 that filters the demodulated signal to extract the selected frequency band of the signal at the baseband. The second frequency may differ from the first frequency by an offset that is approximately equal to a center frequency of the selected frequency band. In one embodiment, the physiological signal is an electrical signal, such as an EEG signal, ECoG signal, EMG signal, field potential, and the selected frequency band is one of an alpha, beta, gamma or high gamma frequency band of the electrical signal. The characteristic of the demodulated signal is power fluctuation of the signal in the selected frequency band. The signal analysis unit 273 may generate a signal triggering at least one of control of therapy to the patient or recording of diagnostic information when the power fluctuation exceeds a threshold.

In some embodiments, the selected frequency band comprises a first selected frequency band and the characteristic comprises a first power. The demodulator 288 demodulates the amplified signal at a third frequency different from the first and second frequencies. The third frequency being selected such that the demodulator 288 substantially centers a second selected frequency band of the signal at a baseband. The signal analysis unit 273 analyzes a second power of the signal in the second selected frequency band, and calculates a power ratio between the first power and the second power. The signal analysis unit 273 generates a signal triggering at least one of control of therapy to the patient or recording of diagnostic information based on the power ratio.

In the example of FIG. 15, chopper-stabilized, superheterodyne amplifier 272 modulates the physiological signal with a first carrier frequency $f_c$, amplifies the modulated signal, and demodulates the amplified signal to baseband with a second frequency equivalent to the first frequency $f_c$ plus (or minus) an offset δ. Signal analysis unit 273 measures a characteristic of the demodulated signal in a selected frequency band.

The second frequency is different from the first frequency $f_c$ and is selected, via the offset δ, to position the demodulated signal in the selected frequency band at the baseband. In particular, the offset may be selected based on the selected frequency band. For example, the frequency band may be a frequency within the selected frequency band, such as a center frequency of the band.

If the selected frequency band is 5 to 15 Hz, for example, the offset δ may be the center frequency of this band, i.e., 10 Hz. In some embodiments, the offset δ may be a frequency elsewhere in the selected frequency band. However, the center frequency generally will be preferred. The second frequency may be generated by shifting the first frequency by the offset amount. Alternatively, the second frequency may be generated independently of the first frequency such that the difference between the first and second frequencies is the offset.

In either case, the second frequency may be equivalent to the first frequency $f_c$ plus or minus the offset δ. If the first frequency $f_c$ is 4000 Hz, for example, and the selected frequency band is 5 to 15 Hz (the alpha band for EEG signals), the offset δ may be selected as the center frequency of that band, i.e., 10 Hz. In this case, the second frequency is the first frequency of 4000 Hz plus or minus 10 Hz. Using the superheterodyne structure, the signal is modulated at 4000 Hz by modulator 282, amplified by amplifier 286 and then demodulated by demodulator 288 at 3990 or 4010 Hz (the first frequency $f_c$ of 4000 Hz plus or minus the offset δ of 10 Hz) to position the 5 to 15 Hz band centered at 10 Hz at baseband, e.g., DC. In this manner the 5 to 15 Hz band can be directly downconverted such that it is substantially centered at DC.

As illustrated in FIG. 15, superheterodyne instrumentation amplifier 272 receives a physiological signal (e.g., $V_{in}$) from sensing elements positioned at a desired location within a patient or external to a patient to detect the physiological signal. For example, the physiological signal may comprise one of an EEG, EcoG, electromyogram EMG, ECG, pressure, temperature, impedance or motion signal. Again, an EEG signal will be described for purposes of illustration. Superheterodyne instrumentation amplifier 272 may be configured to receive the physiological signal ($V_{in}$) as either a differential or signal-ended input. Superheterodyne instrumentation amplifier 272 includes first modulator 282 for modulating the physiological signal from baseband at the carrier frequency ($f_c$). In the example of FIG. 15, an input capacitance ($C_{in}$) 283 couples the output of first modulator 282 to feedback adder 284. Feedback adder 284 will be described below in conjunction with the feedback paths.

Adder 285 represents the inclusion of a noise signal with the modulated signal. Adder 285 represents the addition of low frequency noise, but does not form an actual component of superheterodyne instrumentation amplifier 272. Adder 285 models the noise that comes into superheterodyne instrumentation amplifier 272 from non-ideal transistor characteristics. At adder 285, the original baseband components of the signal are located at the carrier frequency $f_c$. As an example, the baseband components of the signal may have a frequency within a range of 0 to approximately 1000 Hz and the carrier frequency $f_c$ may be approximately 4 kHz to approximately 10 kHz. The noise signal enters the signal pathway, as represented by adder 285, to produce a noisy modulated signal. The noise signal may include 1/f noise, popcorn noise, offset, and any other external signals that may enter the signal pathway at low (baseband) frequency. At adder 285, however, the original baseband components of the signal have already been chopped to a higher frequency band, e.g., 4000 Hz, by first modulator 282. Thus, the low-frequency noise signal is segregated from the original baseband components of the signal.

Amplifier 286 receives the noisy modulated input signal from adder 285. Amplifier 286 amplifies the noisy modulated signal and outputs the amplified signal to a second modulator 288. Offset (δ) 287 may be tuned such that it is approximately equal to a frequency within the selected frequency band, and preferably the center frequency of the selected frequency band. The resulting modulation frequency ($f_c\pm\delta$) used by demodulator 288 is then different from the first carrier frequency $f_c$ by the offset amount δ. In some cases, offset δ 287 may be manually tuned according to the selected frequency band by a physician, technician, or the patient. In other cases, the offset δ 287 may by dynamically tuned to the selected frequency band in accordance with stored frequency band values. For example, different frequency bands may be scanned by automatically or manually tuning the offset δ according to center frequencies of the desired bands. As an example, when monitoring a patient's intent to move, the selected frequency band may be the alpha frequency band (5 Hz to 15 Hz). In this case, the offset δ may be approximately the center frequency of the alpha band, i.e., 10 Hz. As another example, when monitoring tremor, the selected frequency band may be the beta frequency band (15 Hz-35 Hz). In this case, the offset δ may be approximately the center frequency of the beta band, i.e., 25 Hz. As another example, when monitoring intent in the cortex, the selected frequency band may be the high gamma frequency band (150 Hz-200 Hz). In this case, the offset δ may be approximately the center frequency of the high gamma band, i.e., 175 Hz. When monitoring pre-seizure biomarkers in epilepsy, the selected frequency may be fast ripples (500 Hz), in which case the offset δ may be approximately 500 Hz. As another illustration, the selected frequency band passed by filter 274 may be the gamma band (30 Hz-80 Hz), in which case the offset δ may be tuned to approximately the center frequency of the gamma band, i.e., 55 Hz.

Hence, the signal in the selected frequency band may be produced by selecting the offset (δ) 287 such that the carrier frequency plus or minus the offset frequency ($f_c \pm \delta$) is equal to a frequency within the selected frequency band, such as the center frequency of the selected frequency band. In each case, as explained above, the offset may be selected to correspond to the desired band. For example, an offset of 5 Hz would place the alpha band at the baseband frequency, e.g., DC, upon downconversion by the demodulator. Similarly, an offset of 15 Hz would place the beta band at DC upon downconversion, and an offset of 30 Hz would place the gamma band at DC upon downconversion. In this manner, the pertinent frequency band is centered at the baseband. Then, passive low pass filtering may be applied to select the frequency band. In this manner, the superheterodyne architecture serves to position the desired frequency band at baseband as a function of the selected offset frequency used to produce the second frequency for demodulation. In general, in the example of FIG. 15, powered bandpass filtering is not required. Likewise, the selected frequency band can be obtained without the need for oversampling and digitization of the wideband signal.

With further reference to FIG. 15, second modulator 288 demodulates the amplified signal at the second frequency $f_c \pm \delta$, which is separated from the carrier frequency $f_c$ by the offset δ. That is, second modulator 288 modulates the noise signal up to the $f_c \pm \delta$ frequency and demodulates the components of the signal in the selected frequency band directly to baseband. Integrator 289 operates on the demodulated signal to pass the components of the signal in the selected frequency band positioned at baseband and substantially eliminate the components of the noise signal at higher frequencies. In this manner, integrator 289 provides compensation and filtering to the amplified signal to produce an output signal ($V_{out}$). In other embodiments, compensation and filtering may be provided by other circuitry.

As shown in FIG. 15, superheterodyne instrumentation amplifier 272 may include two negative feedback paths to feedback adder 284 to reduce glitching in the output signal ($V_{out}$). In particular, the first feedback path includes a third modulator 290, which modulates the output signal at the carrier frequency plus or minus the offset δ, and a feedback capacitance ($C_{fb}$) 291 that is selected to produce desired gain given the value of the input capacitance ($C_{in}$) 283. The first feedback path produces a feedback signal that is added to the original modulated signal at feedback adder 284 to produce attenuation and thereby generate gain at the output of amplifier 286.

The second feedback path may be optional, and may include an integrator 292, a fourth modulator 293, which modulates the output signal at the carrier frequency plus or minus the offset δ, and high pass filter capacitance ($C_{hp}$) 294. Integrator 292 integrates the output signal and modulator 293 modulates the output of integrator 292 at the carrier frequency. High pass filter capacitance ($C_{hp}$) 294 is selected to substantially eliminate components of the signal that have a frequency below the corner frequency of the high pass filter. For example, the second feedback path may set a corner frequency of approximately equal to 2.5 Hz, 0.5 Hz, or 0.05 Hz. The second feedback path produces a feedback signal that is added to the original modulated signal at feedback adder 284 to increase input impedance at the output of amplifier 286.

As described above, chopper-stabilized, superheterodyne instrumentation amplifier 272 can be used to achieve direct downconversion of a selected frequency band centered at a frequency that is offset from baseband by an amount δ. Again, if the alpha band is centered at 10 Hz, then the offset amount δ used to produce the demodulation frequency $f_c \pm \delta$ may be 10 Hz. As illustrated in FIG. 15, first modulator 282 is run at the carrier frequency ($f_c$), which is specified by the 1/f corner and other constraints, while second modulator 288 is run at the selected frequency band ($f_c \pm \delta$). Multiplication of the physiological signal by the carrier frequency convolves the signal in the frequency domain. The net effect of upmodulation is to place the signal at the carrier frequency ($f_c$). By then running second modulator 288 at a different frequency ($f_c \pm \delta$), the convolution of the signal sends the signal in the selected frequency band to baseband and 2δ. Integrator 289 may be provided to filter out the 2δ component and passes the baseband component of the signal in the selected frequency band.

As illustrated in FIG. 15, signal analysis unit 273 receives the output signal from instrumentation amplifier. In the example of FIG. 15, signal analysis unit 273 includes a passive lowpass filter 274, a power measurement module 276, a lowpass filter 277, a threshold tracker 278 and a comparator 280. Passive lowpass filter 274 extracts the signal in the selected frequency band positioned at baseband. For example, lowpass filter 274 may be configured to reject frequencies above a desired frequency, thereby preserving the signal in the selected frequency band. Power measurement module 276 then measures power of the extracted signal. In some cases, power measurement module 276 may extract the net power in the desired band by full wave rectification. In other cases, power measurement module 276 may extract the net power in the desired band by a squaring power calculation, which may be provided by a squaring power circuit. As the signal has sine and cosine phases, summing of the squares yields a net of 1 and the total power. The measured power is then filtered by lowpass filter 277 and applied to comparator 280. Threshold tracker 278 tracks fluctuations in power measurements of the selected frequency band over a period of time in order to generate a baseline power threshold of the selected frequency band for the patient. Threshold tracker 278 applies the baseline power threshold to comparator 280 in response to receiving the measured power from power measurement module 276.

Comparator 280 compares the measured power from lowpass filter 277 with the baseline power threshold from threshold tracker 278. If the measured power is greater than the baseline power threshold, comparator 280 may output a trigger signal to a processor of a medical device to control therapy and/or recording of diagnostic information. If the measured power is equal to or less than the baseline power threshold, comparator 280 outputs a power tracking measurement to threshold tracker 278, as indicated by the line from comparator 280 to threshold tracker 278. Threshold tracker 278 may include a median filter that creates the baseline threshold level after filtering the power of the signal in the selected frequency band for several minutes. In this way, the measured power of the signal in the selected frequency band may be used by the threshold tracker 278 to update and generate the baseline power threshold of the selected frequency band for the patient. Hence, the baseline power threshold may be dynamically adjusted as the sensed signal changes over time. A signal above or below the baseline power threshold may signify an event that may support generation of a trigger signal.

In some cases, frequency selective signal monitor 270 may be limited to monitoring a single frequency band of the wide band physiological signal at any specific instant. Alternatively, frequency selective signal monitor 270 may be capable of efficiently hopping frequency bands in order to monitor the signal in a first frequency band, monitor the signal in a second frequency band, and then determine whether to trigger therapy and/or diagnostic recording based on some combination of the monitored signals. For example, different frequency bands may be monitored on an alternating basis to support signal analysis techniques that rely on comparison or processing of characteristics associated with multiple frequency bands.

Figure 16:
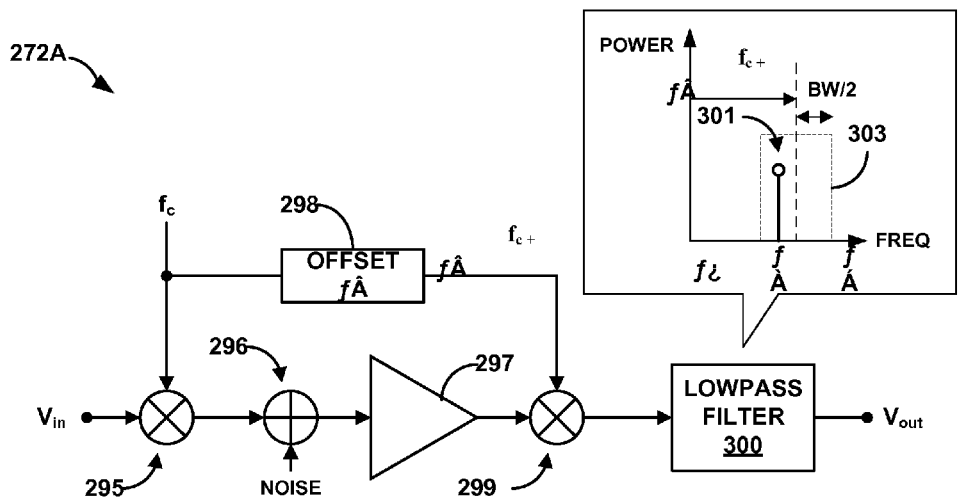
FIG. 16 is a block diagram illustrating a portion of an exemplary chopper-stabilized superheterodyne amplifier for use within the frequency selective signal monitor from FIG. 15.

FIG. 16 is a block diagram illustrating a portion of an exemplary chopper-stabilized superheterodyne instrumentation amplifier 272A for use within frequency selective signal monitor 270 from FIG. 15. Superheterodyne instrumentation amplifier 272A illustrated in FIG. 16 may operate substantially similar to superheterodyne instrumentation amplifier 272 from FIG. 15. Superheterodyne instrumentation amplifier 272A includes a first modulator 295, an amplifier 297, a frequency offset 298, a second modulator 299, and a lowpass filter 300. In some embodiments, lowpass filter 300 may be an integrator, such as integrator 289 of FIG. 15. Adder 296 represents addition of noise to the chopped signal. However, adder 296 does not form an actual component of superheterodyne instrumentation amplifier 272A. Adder 296 models the noise that comes into superheterodyne instrumentation amplifier 272A from non-ideal transistor characteristics.

Superheterodyne instrumentation amplifier 272A receives a physiological signal ($V_{in}$) associated with a patient from sensing elements, such as electrodes, positioned within or external to the patient to detect the physiological signal. First modulator 295 modulates the signal from baseband at the carrier frequency ($f_c$). A noise signal is added to the modulated signal, as represented by adder 296. Amplifier 297 amplifies the noisy modulated signal. Frequency offset 298 is tuned such that the carrier frequency plus or minus frequency offset 298 ($f_c \pm \delta$) is equal to the selected frequency band. Hence, the offset δ may be selected to target a desired frequency band. Second modulator 299 modulates the noisy amplified signal at offset frequency 98 from the carrier frequency $f_c$. In this way, the amplified signal in the selected frequency band is demodulated directly to baseband and the noise signal is modulated to the selected frequency band.

Lowpass filter 300 may filter the majority of the modulated noise signal out of the demodulated signal and set the effective bandwidth of its passband around the center frequency of the selected frequency band. As illustrated in the detail associated with lowpass filter 300 in FIG. 16, a passband 303 of lowpass filter 300 may be positioned at a center frequency of the selected frequency band. In some cases, the offset δ may be equal to this center frequency. Lowpass filter 300 may then set the effective bandwidth (BW/2) of the passband around the center frequency such that the passband encompasses the entire selected frequency band. In this way, lowpass filter 300 passes a signal 301 positioned anywhere within the selected frequency band. For example, if the selected frequency band is 5 to 15 Hz, for example, the offset δ may be the center frequency of this band, i.e., 10 Hz, and the effective bandwidth may be half the full bandwidth of the selected frequency band, i.e., 5 Hz. In this case, lowpass filter 300 rejects or at least attenuates signals above 5 Hz, thereby limiting the passband signal to the alpha band, which is centered at 0 Hz as a result of the superheterodyne process. Hence, the center frequency of the selected frequency band can be specified with the offset δ, and the bandwidth BW of the passband can be obtained independently with the lowpass filter 300, with BW/2 about each side of the center frequency.

Lowpass filter 300 then outputs a low-noise physiological signal ($V_{out}$). The low-noise physiological signal may then be input to signal analysis unit 273 from FIG. 15. As described above, signal analysis unit 273 may extract the signal in the selected frequency band positioned at baseband, measure power of the extracted signal, and compare the measured power to a baseline power threshold of the selected frequency band to determine whether to trigger patient therapy.

Figure 17A:
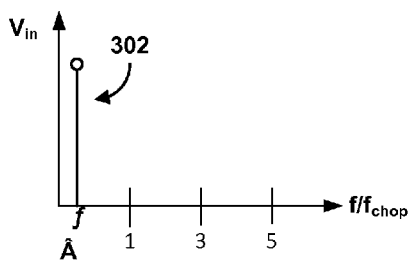
FIGS. 17A-17D are graphs illustrating the frequency components of a signal at various stages within the superheterodyne amplifier of FIG. 16.

FIGS. 17A-17D are graphs illustrating the frequency components of a signal at various stages within superheterodyne instrumentation amplifier 272A of FIG. 16. In particular, FIG. 17A illustrates the frequency components in a selected frequency band within the physiological signal received by frequency selective signal monitor 270. The frequency components of the physiological signal are represented by line 302 and located at offset δ from baseband in FIG. 17A.

Figure 17B:
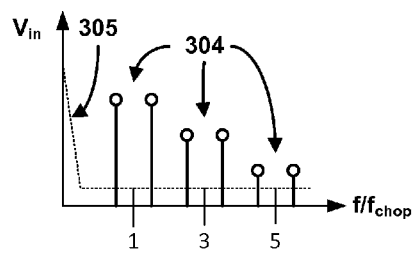

FIG. 17B illustrates the frequency components of the noisy modulated signal produced by modulator 295 and amplifier 297. In FIG. 17B, the original offset frequency components of the physiological signal have been up-modulated at carrier frequency $f_c$ and are represented by lines 304 at the odd harmonics. The frequency components of the noise signal added to the modulated signal are represented by dotted line 305. In FIG. 17B, the energy of the frequency components of the noise signal is located substantially at baseband and energy of the frequency components of the desired signal is located at the carrier frequency ($f_c$) plus and minus frequency offset (δ) 298 and its odd harmonics.

Figure 17C:
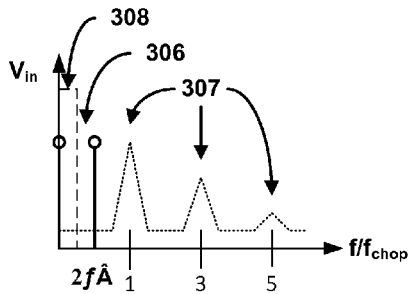

FIG. 17C illustrates the frequency components of the demodulated signal produced by demodulator 299. In particular, the frequency components of the demodulated signal are located at baseband and at twice the frequency offset (2δ), represented by lines 306. The frequency components of the noise signal are modulated and represented by dotted line 307. The frequency components of the noise signal are located at the carrier frequency plus or minus the offset frequency (δ) 298 and its odd harmonics in FIG. 17C. FIG. 17C also illustrates the effect of lowpass filter 300 that may be applied to the demodulated signal. The passband of lowpass filter 300 is represented by dashed line 308.

Figure 17D:
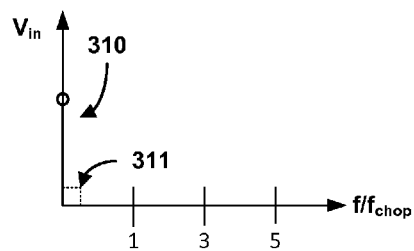

FIG. 17D is a graph that illustrates the frequency components of the output signal. In FIG. 17D, the frequency components of the output signal are represented by line 310 and the frequency components of the noise signal are represented by dotted line 311. FIG. 17D illustrates that lowpass filter 300 removes the frequency components of the demodulated signal located at twice the offset frequency (2δ). In this way, lowpass filter 300 positions the frequency components of the signal at the desired frequency band within the physiological signal at baseband. In addition, lowpass filter 300 removes the frequency components from the noise signal that were located outside of the passband of lowpass filter 300 shown in FIG. 17C. The energy from the noise signal is substantially eliminated from the output signal, or at least substantially reduced relative to the original noise signal that otherwise would be introduced.

Figure 18:
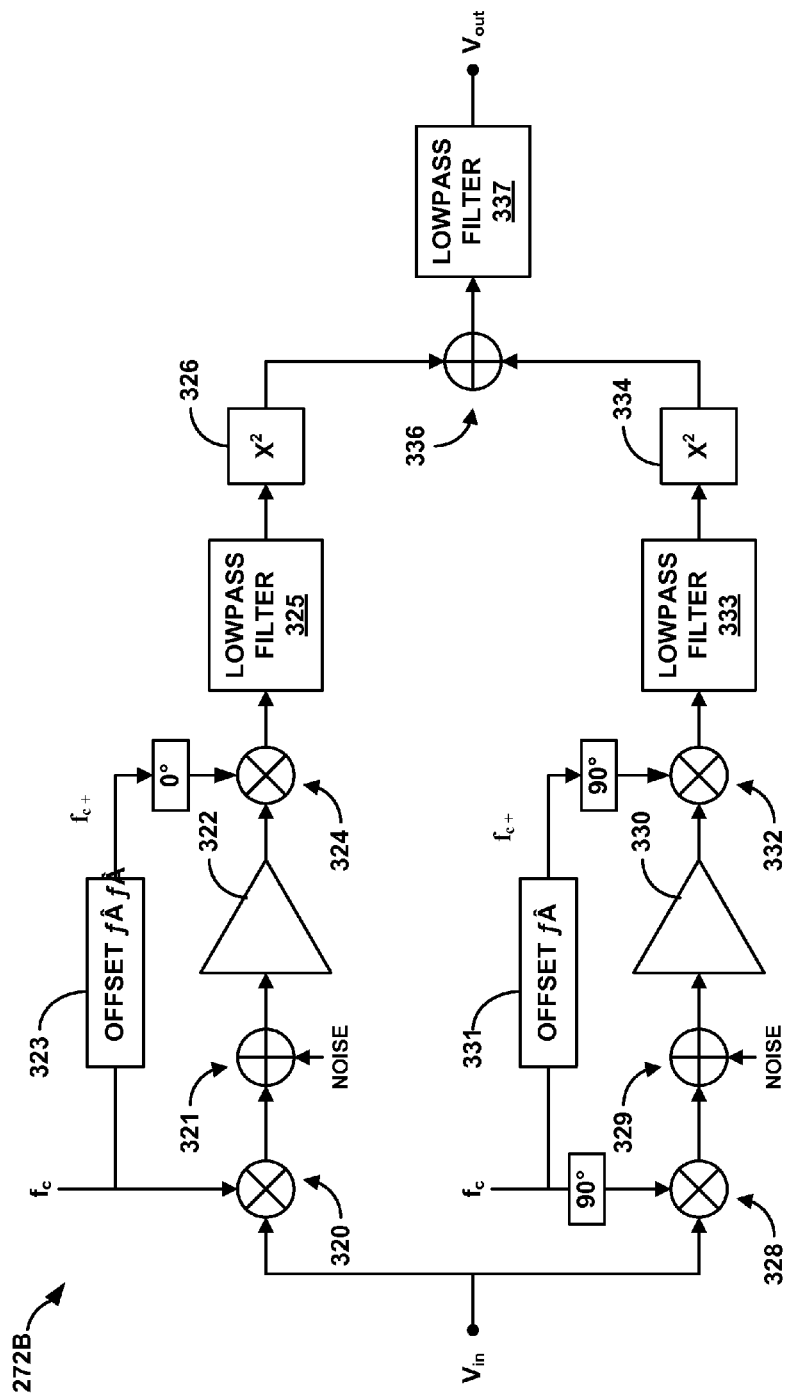
FIG. 18 is a block diagram illustrating a portion of an exemplary chopper-stabilized superheterodyne amplifier with in-phase and quadrature signal paths for use within a frequency selective signal monitor.

FIG. 18 is a block diagram illustrating a portion of an exemplary chopper-stabilized superheterodyne instrumentation amplifier 272B with in-phase and quadrature signal paths for use within frequency selective signal monitor 270 from FIG. 15. The in-phase and quadrature signal paths substantially reduce phase sensitivity within superheterodyne instrumentation amplifier 272B. Because the signal obtained from the patient and the clocks used to produce the modulation frequencies are uncorrelated, the phase of the signal should be taken into account. To address the phasing issue, two parallel heterodyning amplifiers may be driven with in-phase (I) and quadrature (Q) clocks created with on-chip distribution circuits. Net power extraction then can be achieved with superposition of the in-phase and quadrature signals.

An analog implementation may use an on-chip self-cascoded Gilbert mixer to calculate the sum of squares. Alternatively, a digital approach may take advantage of the low bandwidth of the I and Q channels after lowpass filtering, and digitize at that point in the signal chain for digital power computation. Digital computation at the I/Q stage has advantages. For example, power extraction is more linear than a tan h function. In addition, digital computation simplifies offset calibration to suppress distortion, and preserves the phase information for cross-channel coherence analysis. With either technique, a sum of squares in the two channels can eliminate the phase sensitivity between the physiological signal and the modulation clock frequency. The power output signal can lowpass filtered to the order of 1 Hz to track the essential dynamics of a desired biomarker.

Superheterodyne instrumentation amplifier 272B illustrated in FIG. 18 may operate substantially similar to superheterodyne instrumentation amplifier 272 from FIG. 15. Superheterodyne instrumentation amplifier 272B includes an in-phase (I) signal path with a first modulator 320, an amplifier 322, an in-phase frequency offset ($\delta$) 323, a second modulator 324, a lowpass filter 325, and a squaring unit 326. Adder 321 represents addition of noise. Adder 321 models the noise from non-ideal transistor characteristics. Superheterodyne instrumentation amplifier 272B includes a quadrature phase (Q) signal path with a third modulator 328, an adder 329, an amplifier 330, a quadrature frequency offset ($\delta$) 331, a fourth modulator 332, a lowpass filter 333, and a squaring unit 334. Adder 329 represents addition of noise. Adder 329 models the noise from non-ideal transistor characteristics.

Superheterodyne instrumentation amplifier 272B receives a physiological signal ($V_{in}$) associated with a patient from one or more sensing elements. The in-phase (I) signal path modulates the signal from baseband at the carrier frequency ($f_c$), permits addition of a noise signal to the modulated signal, and amplifies the noisy modulated signal. In-phase frequency offset 323 may be tuned such that it is substantially equivalent to a center frequency of a selected frequency band. For the alpha band (5 to 15 Hz), for example, the offset 323 may be approximately 10 Hz. In this example, if the modulation carrier frequency $f_c$ applied by modulator 320 is 4000 Hz, then the demodulation frequency $f_c \pm \delta$ may be 3990 Hz or 4010 Hz.

Second modulator 324 modulates the noisy amplified signal at a frequency ($f_c \pm \delta$) offset from the carrier frequency $f_c$ by the offset amount $\delta$. In this way, the amplified signal in the selected frequency band may be demodulated directly to baseband and the noise signal may be modulated up to the second frequency $f_c \pm \delta$. The selected frequency band of the physiological signal is then substantially centered at baseband, e.g., DC. For the alpha band (5 to 15 Hz), for example, the center frequency of 10 Hz is centered at 0 Hz at baseband. Lowpass filter 325 filters the majority of the modulated noise signal out of the demodulated signal and outputs a low-noise physiological signal. The low-noise physiological signal may then be squared with squaring unit 326 and input to adder 336. In some cases, squaring unit 326 may comprise a self-cascoded Gilbert mixer. The output of squaring unit 126 represents the spectral power of the in-phase signal.

In a similar fashion, the quadrature (Q) signal path modulates the signal from baseband at the carrier frequency ($f_c$). However, the carrier frequency applied by modulator 328 in the Q signal path is 90 degrees out of phase with the carrier frequency applied by modulator 320 in the I signal path. The Q signal path permits addition of a noise signal to the modulated signal, as represented by adder 329, and amplifies the noisy modulated signal via amplifier 330. Again, quadrature offset frequency ($\delta$) 331 may be tuned such it is approximately equal to the center frequency of the selected frequency band. As a result, the demodulation frequency applied to demodulator 332 is ($f_c \pm \delta$). In the quadrature signal path, however, an additional phase shift of 90 degrees is added to the demodulation frequency for demodulator 332. Hence, the demodulation frequency for demodulator 332, like demodulator 324, is $f_c \pm \delta$. However, the demodulation frequency for demodulator 332 is phase shifted by 90 degrees relative to the demodulation frequency for demodulator 324 of the in-phase signal path.

Fourth modulator 332 modulates the noisy amplified signal at the quadrature frequency 331 from the carrier frequency. In this way, the amplified signal in the selected frequency band is demodulated directly to baseband and the noise signal is modulated at the demodulation frequency $f_c \pm \delta$. Lowpass filter 333 filters the majority of the modulated noise signal out of the demodulated signal and outputs a low-noise physiological signal. The low-noise physiological signal may then be squared and input to adder 336. Like squaring unit 326, squaring unit 334 may comprise a self-cascoded Gilbert mixer. The output of squaring unit 334 represents the spectral power of the quadrature signal.

Adder 336 combines the signals output from squaring unit 326 in the in-phase signal path and squaring unit 334 in the quadrature signal path. The output of adder 336 may be input to a lowpass filter 337 that generates a low-noise, phase-insensitive output signal ($V_{out}$). As described above, the signal may be input to signal analysis unit 273 from FIG. 15. As described above, signal analysis unit 273 may extract the signal in the selected frequency band positioned at baseband, measure power of the extracted signal, and compare the measured power to a baseline power threshold of the selected frequency band to determine whether to trigger patient therapy. Alternatively, signal analysis unit 273 may analyze other characteristics of the signal. The signal Vout may be applied to the signal analysis unit 273 as an analog signal. Alternatively, an analog-to-digital converter (ADC) may be provided to convert the signal Vout to a digital signal for application to signal analysis unit 273. Hence, signal analysis unit 273 may include one or more analog components, one or more digital components, or a combination of analog and digital components.

Figure 19:
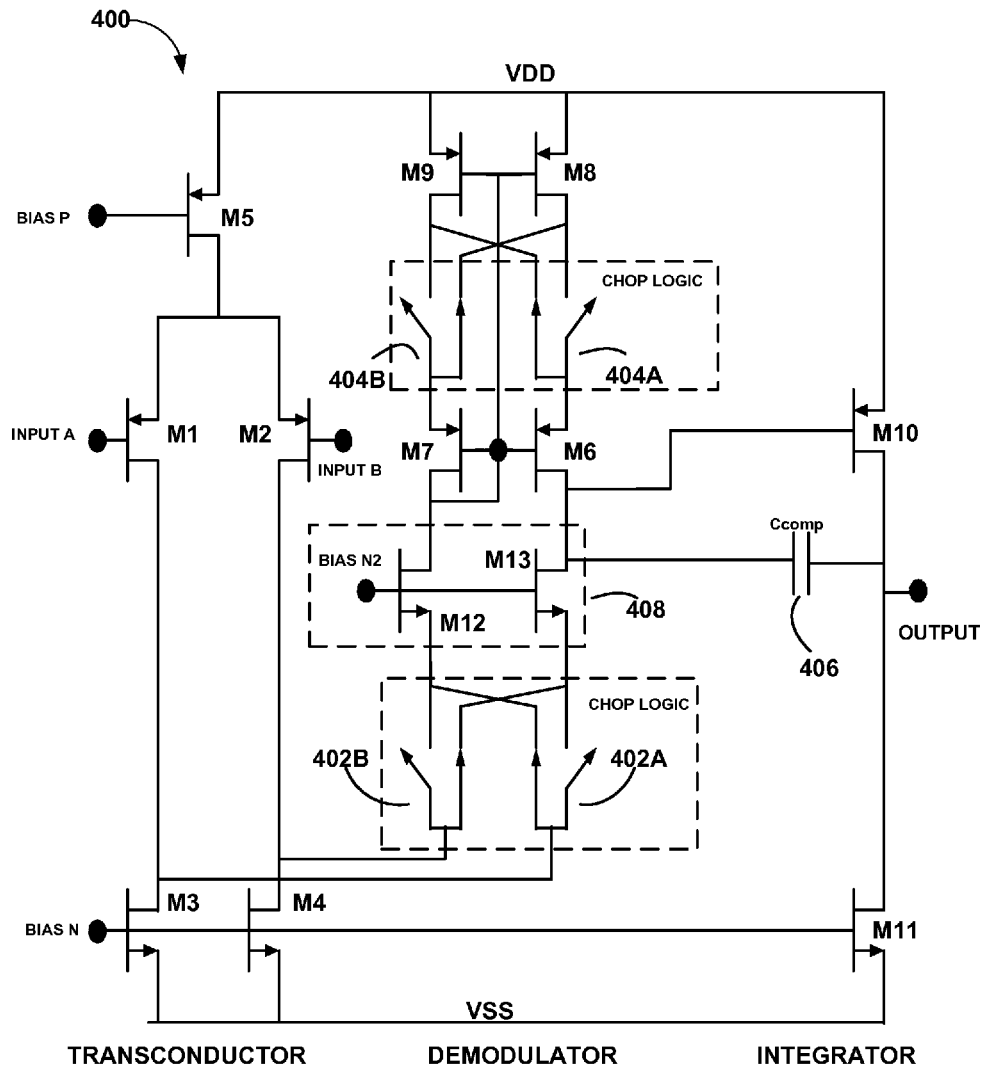
FIG. 19 is a circuit diagram illustrating a chopper-stabilized mixer amplifier suitable for use within the frequency selective signal monitor of FIG. 15.

FIG. 19 is a circuit diagram illustrating an example mixer amplifier circuit 400 for use in superheterodyne instrumentation amplifier 272 of FIG. 15. For example, circuit 400 represents an example of amplifier 286, demodulator 288 and integrator 289 in FIG. 15. Although the example of FIG. 19 illustrates a differential input, circuit 400 may be constructed with a single-ended input. Accordingly, circuit 400 of FIG. 19 is provided for purposes of illustration, without limitation as to other embodiments. In FIG. 19, VDD and VSS indicate power and ground potentials, respectively.

Mixer amplifier circuit 400 amplifies a noisy modulated input signal to produce an amplified signal and demodulates the amplified signal. Mixer amplifier circuit 400 also substantially eliminates noise from the demodulated signal to generate the output signal. In the example of FIG. 19, mixer amplifier circuit 400 is a modified folded-cascode amplifier with switching at low impedance nodes. The modified folded-cascode architecture allows currents to be partitioned to maximize noise efficiency. In general, the folded cascode architecture is modified in FIG. 19 by adding two sets of switches. One set of switches is illustrated in FIG. 19 as switches 402A and 402B (collectively referred to as "switches 402") and the other set of switches includes switches 404A and 404B (collectively referred to as "switches 404").

Switches 402 are driven by chop logic to support the chopping of the amplified signal for demodulation at the chop frequency. In particular, switches 402 demodulate the amplified signal and modulate front-end offsets and 1/f noise. Switches 404 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The output of mixer amplifier circuit 400 is at baseband, allowing an integrator formed by transistor M10 and capacitor 406 (Ccomp) to stabilize a feedback path (not shown in FIG. 19) between the output and input and filter modulated offsets.

In the example of FIG. 19, mixer amplifier circuit 400 has three main blocks: a transconductor, a demodulator, and an integrator. The core is similar to a folded cascode. In the transconductor section, transistor M5 is a current source for the differential pair of input transistors M1 and M2. In some embodiments, transistor M5 may pass approximately 800 nA, which is split between transistors M1 and M2, e.g., 400 nA each. Transistors M1 and M2 are the inputs to amplifier 286. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The AC current at the chop frequency from transistors M1 and M2 also flows through the legs of the demodulator. Switches 402 alternate the current back and forth between the legs of the demodulator to demodulate the measurement signal back to baseband, while the offsets from the transconductor are up-modulated to the chopper frequency. As discussed previously, transistors M6, M7, M8 and M9 form a self-biased cascode mirror, and make the signal single-ended before passing into the output integrator formed by transistor M10 and capacitor 406 (Ccomp). Switches 404 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 408 suppressed. Bias N2 transistors M12 and M13 form a common gate amplifier that presents a low impedance to the chopper switching and passes the signal current to transistors M6 and M7 with immunity to the voltage on the drains.

The output DC signal current and the upmodulated error current pass to the integrator, which is formed by transistor M10, capacitor 406, and the bottom NFET current source transistor M11. Again, this integrator serves to both stabilize the feedback path and filter out the upmodulated error sources. The bias for transistor M10 may be approximately 100 nA, and is scaled compared to transistor M8. The bias for lowside NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 19 may be field effect transistors (FETs), and more particularly CMOS transistors.

Figure 20:
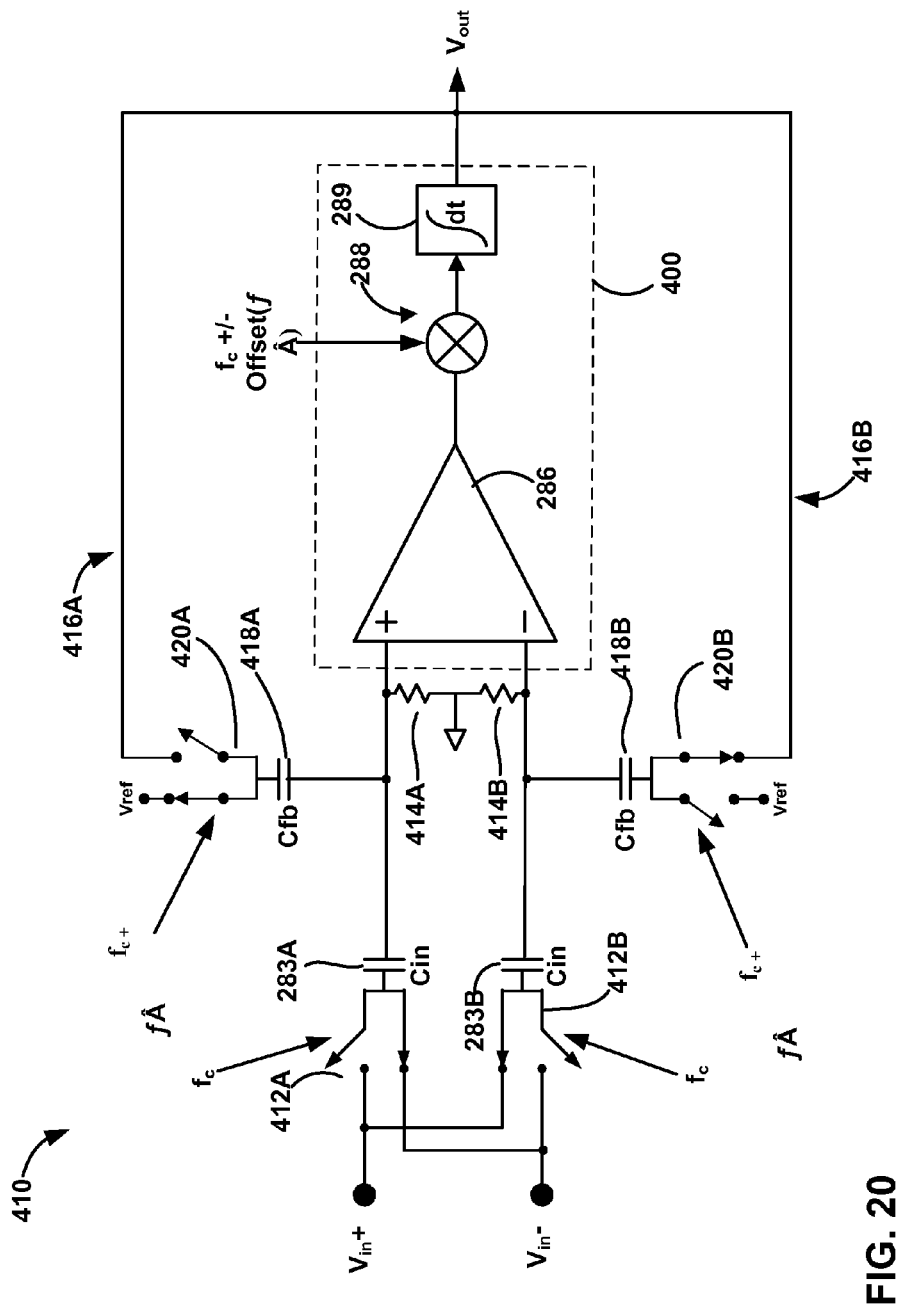
FIG. 20 is a circuit diagram illustrating a chopper-stabilized, superheterodyne instrumentation amplifier with differential inputs.

FIG. 20 is a circuit diagram illustrating an instrumentation amplifier 410 with differential inputs $V_{in}+$ and $V_{in}-$. Instrumentation amplifier 410 is an example embodiment of superheterodyne instrumentation amplifier 272 previously described in this disclosure with reference to FIG. 15. FIG. 20 uses several reference numerals from FIG. 15 to refer to like components. However, the optional high pass filter feedback path comprising components 292, 293 and 294 is omitted from the example of FIG. 20. In general, instrumentation amplifier 410 may be constructed as a single-ended or differentia amplifier. The example of FIG. 20 illustrates example circuitry for implementing a differential amplifier. The circuitry of FIG. 20 may be configured for use in each of the I and Q signal paths of FIG. 18.

In the example of FIG. 20, instrumentation amplifier 410 includes an interface to one or more sensing elements that produce a differential input signal providing voltage signals $V_{in}+$, $V_{in}-$. The differential input signal may be provided by a sensor comprising any of a variety of sensing elements, such as a set of one or more electrodes, an accelerometer, a pressure sensor, a force sensor, a gyroscope, a humidity sensor, a chemical sensor, or the like. For brain sensing, the differential signal $V_{in}+$, $V_{in}-$ may be, for example, an EEG or EcoG signal.

The differential input voltage signals are connected to respective capacitors 283A and 283B (collectively referred to as "capacitors 283") through switches 412A and 412B, respectively. Switches 412A and 412B may collectively form modulator 282 of FIG. 15. Switches 412A, 412B are driven by a clock signal provided by a system clock (not shown) at the carrier frequency $f_c$. Switches 412A, 412B may be cross-coupled to each other, as shown in FIG. 20, to reject common-mode signals. Capacitors 283 are coupled at one end to a corresponding one of switches 412A, 412B and to a corresponding input of amplifier 286 at the other end. In particular, capacitor 283A is coupled to the positive input of amplifier 286, and capacitor 283B is coupled to the negative input of amplifier 286, providing a differential input. Amplifier 286, modulator 288 and integrator 289 together may form a mixer amplifier, which may be constructed similar to mixer amplifier 400 of FIG. 19.

In FIG. 20, switches 412A, 412B and capacitors 283A, 283B form a front end of instrumentation amplifier 410. In particular, the front end may operate as a continuous time switched capacitor network. Switches 412A, 412B toggle between an open state and a closed state in which inputs signals $V_{in}+$, $V_{in}-$ are coupled to capacitors 283A, 283B at a clock frequency $f_c$ to modulate (chop) the input signal to the carrier (clock) frequency. As mentioned previously, the input signal may be a low frequency signal within a range of approximately 0 Hz to approximately 1000 Hz and, more particularly, approximately 0 Hz to 500 Hz, and still more particularly less than or equal to approximately 100 Hz. The carrier frequency may be within a range of approximately 4 kHz to approximately 10 kHz. Hence, the low frequency signal is chopped to the higher chop frequency band.

Switches 412A, 412B toggle in-phase with one another to provide a differential input signal to amplifier 286. During one phase of the clock signal $f_c$, switch 412A connects Vin+ to capacitor 283A and switch 412B connects Vin− to capacitor 283B. During another phase, switches 412A, 412B change state such that switch 412A decouples Vin+ from capacitor 283A and switch 412B decouples Vin− from capacitor 283B. Switches 412A, 412B synchronously alternate between the first and second phases to modulate the differential voltage at the carrier frequency. The resulting chopped differential signal is applied across capacitors 283A, 283B, which couple the differential signal across the positive and negative inputs of amplifier 286.

Resistors 414A and 414B (collectively referred to as "resistors 414") may be included to provide a DC conduction path that controls the voltage bias at the input of amplifier 286. In other words, resistors 414 may be selected to provide an equivalent resistance that is used to keep the bias impedance high. Resistors 414 may, for example, be selected to provide a 5 GΩ equivalent resistor, but the absolute size of the equivalent resistor is not critical to the performance of instrumentation amplifier 410. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance (Cin) of approximately 25 pF. In light of this, a stronger motivation for keeping the impedance high is the rejection of high frequency harmonics which can alias into the signal chain due to settling at the input nodes of amplifier 286 during each half of a clock cycle.

Resistors 414 are merely exemplary and serve to illustrate one of many different biasing schemes for controlling the signal input to amplifier 286. In fact, the biasing scheme is flexible because the absolute value of the resulting equivalent resistance is not critical. In general, the time constant of resistor 414 and input capacitor 283 may be selected to be approximately 100 times longer than the reciprocal of the chopping frequency.

Amplifier 286 may produce noise and offset in the differential signal applied to its inputs. For this reason, the differential input signal is chopped via switches 412A, 412B and capacitors 283A, 283B to place the signal of interest in a different frequency band from the noise and offset. Then, instrumentation amplifier 410 chops the amplified signal at modulator 88 a second time to demodulate the signal of interest down to baseband while modulating the noise and offset up to the chop frequency band. In this manner, instrumentation amplifier 410 maintains substantial separation between the noise and offset and the signal of interest.

Modulator 288 may support direct downconversion of the selected frequency band using a superheterodyne process. In particular, modulator 288 may demodulate the output of amplifier 86 at a frequency equal to the carrier frequency $f_c$ used by switches 412A, 412B plus or minus an offset δ that is substantially equal to the center frequency of the selected frequency band. In other words, modulator 88 demodulates the amplified signal at a frequency of $f_c \pm \delta$. Integrator 289 may be provided to integrate the output of modulator 288 to produce output signal Vout. Amplifier 286 and differential feedback path branches 416A, 416B process the noisy modulated input signal to achieve a stable measurement of the low frequency input signal output while operating at low power.

Operating at low power tends to limit the bandwidth of amplifier 286 and creates distortion (ripple) in the output signal. Amplifier 286, modulator 288, integrator 289 and feedback paths 416A, 416B may substantially eliminate dynamic limitations of chopper stabilization through a combination of chopping at low-impedance nodes and AC feedback, respectively.

In FIG. 20, amplifier 286, modulator 288 and integrator 289 are represented with appropriate circuit symbols in the interest of simplicity. However, it should be understood that such components may be implemented in accordance with the circuit diagram of mixer amplifier circuit 400 provided in FIG. 19. Instrumentation amplifier 410 may provide synchronous demodulation with respect to the input signal and substantially eliminate 1/f noise, popcorn noise, and offset from the signal to output a signal that is an amplified representation of the differential voltage Vin+, Vin−.

Without the negative feedback provided by feedback path 416A, 416B, the output of amplifier 286, modulator 288 and integrator 289 could include spikes superimposed on the desired signal because of the limited bandwidth of the amplifier at low power. However, the negative feedback provided by feedback path 416A, 416B suppresses these spikes so that the output of instrumentation amplifier 410 in steady state is an amplified representation of the differential voltage produced across the inputs of amplifier 286 with very little noise.

Feedback paths 416A, 216B, as shown in FIG. 20, include two feedback path branches that provide a differential-to-single ended interface. Amplifier 286, modulator 288 and integrator 289 may be referred to collectively as a mixer amplifier. The top feedback path branch 416A modulates the output of this mixer amplifier to provide negative feedback to the positive input terminal of amplifier 286. The top feedback path branch 416A includes capacitor 418A and switch 420A. Similarly, the bottom feedback path branch 416B includes capacitor 418B and switch 420B that modulate the output of the mixer amplifier to provide negative feedback to the negative input terminal of the mixer amplifier. Capacitors 418A, 418B are connected at one end to switches 420A, 420B, respectively, and at the other end to the positive and negative input terminals of the mixer amplifier, respectively. Capacitors 418A, 418B may correspond to capacitor 291 in FIG. 15. Likewise, switches 420A, 420B may correspond to modulator 290 of FIG. 15.

Switches 420A and 420B toggle between a reference voltage (Vref) and the output of the mixer amplifier 400 to place a charge on capacitors 418A and 418B, respectively. The reference voltage may be, for example, a mid-rail voltage between a maximum rail voltage of amplifier 286 and ground. For example, if the amplifier circuit is powered with a source of 0 to 2 volts, then the mid-rail Vref voltage may be on the order of 1 volt. Switches 420A and 420B should be 180 degrees out of phase with each other to ensure that a negative feedback path exists during each half of the clock cycle. One of switches 420A, 420B should also be synchronized with the mixer amplifier 400 so that the negative feedback suppresses the amplitude of the input signal to the mixer amplifier to keep the signal change small in steady state. Hence, a first one of the switches 420A, 420B may modulate at a frequency of $f_c \pm \delta$, while a second switch 420A, 420B modulates at a frequency of $f_c \pm \delta$, but 180 degrees out of phase with the first switch. By keeping the signal change small and switching at low impedance nodes of the mixer amplifier, e.g., as shown in the circuit diagram of FIG. 19, the only significant voltage transitions occur at switching nodes. Consequently, glitching (ripples) is substantially eliminated or reduced at the output of the mixer amplifier.

Switches 412 and 420, as well as the switches at low impedance nodes of the mixer amplifier, may be CMOS SPDT switches. CMOS switches provide fast switching dynamics that enables switching to be viewed as a continuous process. The transfer function of instrumentation amplifier 210 may be defined by the transfer function provided in equation (1) below, where Vout is the voltage of the output of mixer amplifier 400, Cin is the capacitance of input capacitors 283, ΔVin is the differential voltage at the inputs to amplifier 286, Cfb is the capacitance of feedback capacitors 418A, 418B, and Vref is the reference voltage that switches 420A, 420B mix with the output of mixer amplifier 400.

$$Vout = Cin(\Delta Vin)/Cfb + Vref \qquad (1)$$

From equation (1), it is clear that the gain of instrumentation amplifier 410 is set by the ratio of input capacitors Cin and feedback capacitors Cfb, i.e., capacitors 283 and capacitors 418. The ratio of Cin/Cfb may be selected to be on the order of 100. Capacitors 418 may be poly-poly, on-chip capacitors or other types of MOS capacitors and should be well matched, i.e., symmetrical.

Although not shown in FIG. 20, instrumentation amplifier 410 may include shunt feedback paths for auto-zeroing amplifier 410. The shunt feedback paths may be used to quickly reset amplifier 410. An emergency recharge switch also may be provided to shunt the biasing node to help reset the amplifier quickly. The function of input capacitors 283 is to up-modulate the low-frequency differential voltage and reject common-mode signals. As discussed above, to achieve up-modulation, the differential inputs are connected to sensing capacitors 283A, 283B through SPDT switches 412A, 412B, respectively. The phasing of the switches provides for a differential input to amplifier 286. These switches 412A, 412B operate at the clock frequency, e.g., 4 kHz. Because capacitors 283A, 283B toggle between the two inputs, the differential voltage is up-modulated to the carrier frequency while the low-frequency common-mode signals are suppressed by a zero in the charge transfer function. The rejection of higher-bandwidth common signals relies on this differential architecture and good matching of the capacitors.

Blanking circuitry may be provided in some embodiments for applications in which measurements are taken in conjunction with stimulation pulses delivered by a cardiac pacemaker, cardiac defibrillator, or neurostimulator. Such blanking circuitry may be added between the inputs of amplifier 286 and coupling capacitors 283A, 283B to ensure that the input signal settles before reconnecting amplifier 86 to the input signal. For example, the blanking circuitry may be a blanking multiplexer (MUX) that selectively couples and de-couples amplifier 286 from the input signal. This blanking circuitry may selectively decouple the amplifier 286 from the differential input signal and selectively disable the first and second modulators, i.e., switches 412, 420, e.g., during delivery of a stimulation pulse.

A blanking MUX is optional but may be desirable. The clocks driving switches 412, 420 to function as modulators cannot be simply shut off because the residual offset voltage on the mixer amplifier would saturate the amplifier in a few milliseconds. For this reason, a blanking MUX may be provided to decouple amplifier 86 from the input signal for a specified period of time during and following application of a stimulation by a cardiac pacemaker or defibrillator, or by a neurostimulator.

To achieve suitable blanking, the input and feedback switches 412, 420 should be disabled while the mixer amplifier continues to demodulate the input signal. This holds the state of integrator 289 within the mixer amplifier because the modulated signal is not present at the inputs of the integrator, while the demodulator continues to chop the DC offsets. Accordingly, a blanking MUX may further include circuitry or be associated with circuitry configured to selectively disable switches 412, 420 during a blanking interval. Post blanking, the mixer amplifier may require additional time to resettle because some perturbations may remain. Thus, the total blanking time includes time for demodulating the input signal while the input switches 412, 420 are disabled and time for settling of any remaining perturbations. An example blanking time following application of a stimulation pulse may be approximately 8 ms with 5 ms for the mixer amplifier and 3 ms for the AC coupling components.

Examples of various additional chopper amplifier circuits that may be suitable for or adapted to the techniques, circuits and devices of this disclosure are described in U.S. Pat. No. 7,385,443 to Timothy J. Denison, which is entitled "Chopper Stabilized Instrumentation Amplifier" and was issued on Jun. 10, 2008. The entire content of U.S. Pat. No. 7,385,443 is incorporated herein by reference.

Various embodiments of the described invention may include processors that are realized by microprocessors, ASICs, FPGA, or other equivalent integrated logic circuitry. The processor may also utilize several different types of storage methods to hold computer-readable instructions for the device operation and data storage. These memory and storage media types may include a type of hard disk, RAM, or flash memory, e.g. CompactFlash, SmartMedia, or Secure Digital (SD). Each storage option may be chosen depending on the embodiment of the invention. While IMD 14 may contain permanent memory, external programmer 20 may contain a more portable removable memory type to enable easy data transfer or offline data analysis.

Many embodiments of the disclosure have been described. Various modifications may be made without departing from the scope of the claims. For example, while an EEG signal is used in many of the examples herein to detect volitional patient input, in other embodiments, other bioelectrical signals may also be useful. As other examples of bioelectrical signals that may be indicative of volitional patient input, an EMG signal may be used to detect specific muscle movement (e.g., eye winks, movement of a limb, etc.) or a specific pattern of muscle movement, or an ECoG signal that measures electrical signals on a surface of brain 16 may also indicate a particular volitional patient input. As another example, electrodes placed within the motor cortex or other regions of brain 16 may detect field potentials within the particular region of the brain, and the field potential may be indicative of a particular patient input. The particular bioelectrical signal that is indicative of the volitional patient input related to the therapy adjustment may be determined during a trial stage, as described above with respect to the EEG signal.

In addition, a processor may employ any suitable signal processing technique to determine whether the bioelectrical signal includes the biosignal. For example, as described above with respect to EEG signals, an EMG, ECoG or field potential signal may be analyzed for a relationship between a voltage or amplitude of the signal and a threshold value, temporal correlation or frequency correlation with a template signal, power levels within one or more frequency bands, ratios of power levels within two or more frequency bands, or combinations thereof.

These and other embodiments are within the scope of the following claims.

What is claimed is:

1. A method comprising:
receiving an electrical signal sensed from a patient, wherein the electrical signal comprises an electromyogram (EMG) signal;
receiving an indication of an input indicative of a patient activity;
associating at least one biosignal with the input indicative of the patient activity, wherein the at least one biosignal is based on the electrical signal;
detecting, from the patient, the at least one biosignal that results from a volitional patient input corresponding to the input indicative of the patient activity; and
controlling, by a processor and based on the detection of the at least one biosignal, adjustment of a parameter that at least partially defines therapy delivery to the patient.

2. The method of claim 1, further comprising controlling a therapy module to deliver therapy to the patient according to at least the adjusted parameter.

3. The method of claim 1, wherein detecting the at least one biosignal comprises detecting the at least one biosignal from a brain of the patient.

4. The method of claim 3, wherein the electrical signal is a first electrical signal and the EMG signal is a first EMG signal, and wherein the biosignal is extracted from a second electrical signal comprising at least one of an electroencephalogram (EEG) signal, second EMG signal, electrocorticogram (ECoG) signal or a field potential within the brain of the patient.

5. The method of claim 1, wherein detecting the at least one biosignal comprises detecting the at least one biosignal from one or more muscles associated with the patient activity.

6. The method of claim 1, wherein the biosignal comprises at least one of a frequency component of the electrical signal, an amplitude of the electrical signal, or a pattern in an amplitude waveform of the electrical signal.

7. The method of claim 1, wherein controlling the adjustment of the parameter comprises adjusting the parameter of therapy by at least one of increasing or decreasing a therapy parameter value, shifting between stored therapy programs, or modifying a sensory cue.

8. The method of claim 1, further comprising controlling a feedback mechanism to indicate that the biosignal was detected.

9. The method of claim 1, wherein:
receiving the indication of the input indicative of the patient activity comprises receiving, by an implantable medical device, the indication of the input indicative of the patient activity; and
associating the at least one biosignal with the input indicative of the patient activity comprises associating, by the implantable medical device, the at least one biosignal with the input indicative of the patient activity.

10. The method of claim 1, wherein:
receiving the indication of the input indicative of the patient activity comprises receiving, by an external programmer for an implantable medical device configured to deliver the therapy to the patient, the indication of the input indicative of the patient activity, the input indicative of the patient activity received via a user interface of the external programmer; and
associating the at least one biosignal with the input indicative of the patient activity comprises associating, by the external programmer, the at least one biosignal with the input indicative of the patient activity.

11. The method of claim 1, wherein the electrical signal is a first electrical signal and the at least one biosignal is an at least one first biosignal, and wherein the method further comprises:
receiving a second electrical signal sensed from the patient; and
associating at least one second biosignal with the input indicative of the patient activity, wherein:
the at least one second biosignal is based on the second electrical signal,
detecting the at least one first biosignal that results from the volitional patient input comprises detecting both of the at least one first biosignal and the at least one second biosignal that each result from the volitional patient input corresponding to the input indicative of the patient activity, and
controlling adjustment of the parameter comprises controlling, based on the detection of both the at least one first biosignal and the at least one second biosignal, adjustment of the parameter that at least partially defines therapy delivery to the patient.

12. A system comprising:
a processor configured to:
receive an electrical signal sensed from a patient, wherein the electrical signal comprises an electromyogram (EMG) signal,
receive an indication of an input indicative of a patient activity, and
associate at least one biosignal with the input indicative of the patient activity,
wherein the at least one biosignal is based on the electrical signal;
a biosignal detection module configured to detect, from the patient, the at least one biosignal that results from a volitional patient input corresponding to the input indicative of the patient activity; and
a therapy module configured to deliver therapy to the patient, wherein the therapy is at least partially defined by a parameter adjusted based on the detection of the at least one biosignal.

13. The system of claim 12, wherein the biosignal detection module is configured to detect the at least one biosignal from a brain of the patient.

14. The system of claim 13, wherein the electrical signal is a first electrical signal and the EMG signal is a first EMG signal, and
wherein the biosignal detection module is configured to extract the biosignal from a second electrical signal comprising at least one of an electroencephalogram (EEG) signal, second EMG signal, electrocorticogram (ECoG) signal or a field potential within the brain of the patient.

15. The system of claim 12, wherein the biosignal detection module is configured to detect the at least one biosignal from one or more muscles associated with the patient activity.

16. The system of claim 12, wherein the biosignal comprises at least one of a frequency component of the electrical signal, an amplitude of the electrical signal, or a pattern in an amplitude waveform of the electrical signal.

17. The system of claim 12, further comprising a feedback mechanism separate from the therapy module, wherein the processor is configured to control the feedback mechanism to indicate that the biosignal was detected.

18. The system of claim 12, further comprising an implantable medical device that comprises the processor, and wherein the processor is configured to control, based on the detection of the at least one biosignal, adjustment of the parameter that at least partially defines therapy delivered by the therapy module.

19. The system of claim 12, wherein the processor is a first processor, and wherein the system further comprises:
an external programmer that comprises the first processor; and
an implantable medical device comprising a second processor configured to control, based on the detection of the at least one biosignal, adjustment of the parameter that at least partially defines therapy delivered by the therapy module.

20. A non-transitory computer-readable storage medium comprising one or more instructions that, when executed, cause one or more processors to:
receive an electrical signal sensed from a patient, wherein the electrical signal comprises an electromyogram (EMG) signal;
receive an indication of an input indicative of a patient activity;

associate at least one biosignal with the input indicative of the patient activity, wherein the at least one biosignal is based on the electrical signal;

detect, from the patient, the at least one biosignal that results from a volitional patient input corresponding to the input indicative of the patient activity; and control, based on the detection of the at least one biosignal, adjustment of a parameter that at least partially defines therapy delivered to the patient.

21. The non-transitory computer-readable storage medium of claim 20, further comprising instructions that cause the one or more processors to control a feedback mechanism to indicate that the biosignal was detected.

22. A system comprising:
means for receiving an electrical signal sensed from a patient, wherein the electrical signal comprises an electromyogram (EMG) signal;
means for receiving an indication of an input indicative of a patient activity;
means for associating at least one biosignal with the input indicative of the patient activity, wherein the at least one biosignal is based on the electrical signal;
means for detecting, from the patient, the at least one biosignal that results from a volitional patient input corresponding to the input indicative of the patient activity; and
means for controlling, based on the detection of the at least one biosignal, adjustment of a parameter that at least partially defines therapy delivery to the patient.

23. The system of claim 22, wherein the means for detecting the at least one biosignal comprises means for detecting the at least one biosignal from a brain of the patient.

24. The system of claim 22, wherein the means for detecting the at least one biosignal comprises means for detecting the at least one biosignal from one or more muscles associated with the patent activity.

25. A method comprising:
receiving, by an external programmer, an electrical signal sensed from a patient, the external programmer including a user interface and a telemetry module;
receiving, by the external programmer and via the user interface, an input indicative of patient activity;
associating, by the external programmer, at least one biosignal with the input indicative of the patient activity, wherein the at least one biosignal is based on the electrical signal;
detecting, from the patient, the at least one biosignal that results from a volitional patient input corresponding to the input indicative of the patient activity; and
controlling, by a processor and based on the detection of the at least one biosignal, adjustment of a parameter that at least partially defines therapy delivery to the patient.

26. A system comprising:
an external programmer comprising a user interface and a telemetry module, the external programmer configured to:
receive an electrical signal sensed from a patient,
receive, via the user interface, an input indicative of a patient activity, and
associate at least one biosignal with the input indicative of the patient activity,
wherein the at least one biosignal is based on the electrical signal;
a biosignal detection module configured to detect, from the patient, the at least one biosignal that results from a volitional patient input corresponding to the input indicative of the patient activity; and
a therapy module configured to deliver therapy to the patient, wherein the therapy is at least partially defined by a parameter adjusted based on the detection of the at least one biosignal.

* * * * *